US008236307B2

(12) United States Patent
Dennis et al.

(10) Patent No.: US 8,236,307 B2
(45) Date of Patent: Aug. 7, 2012

(54) HUMANIZED ANTI-FGF19 ANTAGONISTS AND METHODS USING SAME

(75) Inventors: Mark Dennis, San Carlos, CA (US); Luc Desnoyers, San Francisco, CA (US); Dorothy French, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 70 days.

(21) Appl. No.: 12/671,974

(22) PCT Filed: Aug. 1, 2008

(86) PCT No.: PCT/US2008/071955
§ 371 (c)(1),
(2), (4) Date: Jul. 28, 2010

(87) PCT Pub. No.: WO2009/035786
PCT Pub. Date: Mar. 19, 2009

(65) Prior Publication Data
US 2011/0076262 A1   Mar. 31, 2011

Related U.S. Application Data

(60) Provisional application No. 60/953,908, filed on Aug. 3, 2007.

(51) Int. Cl.
*A61K 39/395* (2006.01)
*C07K 16/22* (2006.01)
*C12P 21/08* (2006.01)
*C12N 5/07* (2010.01)
*C07H 21/04* (2006.01)

(52) U.S. Cl. ............... 424/133.1; 424/145.1; 530/387.3; 530/388.24; 435/69.6; 435/326; 536/23.53

(58) Field of Classification Search .................. None
See application file for complete search history.

(56) References Cited

U.S. PATENT DOCUMENTS

| | | | |
|---|---|---|---|
| 6,632,927 | B2 | 10/2003 | Adair et al. |
| 7,678,373 | B2 | 3/2010 | Desnoyers et al. |
| 2002/0012961 | A1 | 1/2002 | Bostein et al. |
| 2002/0042367 | A1 | 4/2002 | Stewart et al. |
| 2002/0155543 | A1 | 10/2002 | Adams et al. |
| 2004/0126852 | A1 | 7/2004 | Stewart et al. |
| 2004/0146908 | A1 | 7/2004 | Adams et al. |
| 2005/0026243 | A1 | 2/2005 | Stewart et al. |
| 2005/0026832 | A1 | 2/2005 | Adams et al. |
| 2005/0196842 | A1 | 9/2005 | Botstein et al. |
| 2007/0042395 | A1 | 2/2007 | Botstein et al. |
| 2007/0077626 | A1 | 4/2007 | Botstein et al. |

FOREIGN PATENT DOCUMENTS

| | | |
|---|---|---|
| WO | 99/27100 | 6/1999 |
| WO | 01/18210 A1 | 3/2001 |
| WO | 02/46467 A2 | 6/2002 |
| WO | 03/025138 A2 | 3/2003 |
| WO | 03/065006 A2 | 8/2003 |
| WO | 03/103725 A1 | 12/2003 |
| WO | 2007/136893 A2 | 11/2007 |

OTHER PUBLICATIONS

"International Search Report for PCT/US2007/061936" (4 pages).
Abbass et al., "Altered expression of fibroblast growth factor receptors in human pituitary adenomas" *J. Clin Endocrinol Metab.* 82(4):1160-1166 (Apr. 1997).
Amit et al., "Three-Dimensional Structure of an Antigen-Antibody Complex at 2.8 A Resolution" *Science* 233:747-753 (Aug. 1986).
Auguste et al., "Regulation of vascular development by fibroblast growth factors" *Cell Tissue Res.* 314(1):157-166 (Oct. 2003).
Cappellen et al., "Frequent activating mutations of FGFR3 in human bladder and cervix carcinomas" *Nature Genetics* 23:18-20 (Sep. 1999).
Desnoyers et al., "Targeting FGF19 inhibits tumor growth in colon cancer xenograft and FGF19 transgenic hepatocellular carcinoma models." *Oncogene* 27(1):85-97 (Jan. 2008).
Eswarakumar et al., "Cellular signaling by fibroblast growth factor receptors" *Cytokine Growth Factor Rev.* 16(2):139-149 (Apr. 2005).
Fu et al., "Fibroblast Growth Factor 19 Increases Metabolic Rate and Reverses Dietry and Leptin-Deficient Diabetes" *Endocrinology* 145(6):2594-2603 (Jun. 2004).
Gowardhan et al., "Evaluation of the fibloblast growth factor system as a potential target for therapy in human prostate cancer" *Br J Cancer* 92:320-327 (2005).
Gutierrez et al., "Bile acids decrease hepatic paraoxonase 1 expression and plasma high-density lipoprotein levels via FXR-mediated signaling of FGFR4" *Arteriosclerosis, Thrombosis, and Vascular Biology* 26:301-306 (2006).
Hakimi et al., "Reduced immunogenicity and improved pharmacokinetics of humanized anti-Tac in cynomolgus monkeys" *J Immunol.* 147(4):1352-1359 (Aug. 15, 1991).
Harmer et al., "The Crystal Structure of Fibroblast Growth Factor (FGF) 19 Reveals Novel Features of the FGF Family and Offers a Structural Basis for its Unusual Receptor Affinity" *Biochemistry* 43(3):629-640 (Jan. 27, 2004).
Holt et al., "Definition of a novel growth factor-dependent signal cascade for the suppression of bile acid biosynthesis" *Genes Dev.* 17(13):1581-1591 (Jul. 1, 2003).
Holzel et al., "Targeting FGF19 as a therapeutic for hepatocellular carcinoma (Abstract No. 328)" *EJC Supplements* (Poster presented at 14th European Cancer Conference (ECCO 14), Barcelona, Spain, Sep. 23-27, 2007) 5(4):65.
Jaakkola et al., "Amplification of fgfr4 gene in human breast and gynecological cancers" *Int J Cacer.* 54(3):378-382 (May 28, 1993).
Jaffers et al., "Monoclonal Antibody Therapy, Anti-Idiotypic and Non-Anti-Idiotypic Antibodies to OKT3 Arising Despite Intense Immunosuppression" *Transplantation* 41(5):572-578 (May 1986).
Jang et al., "Mutations in fibroblast growth factor receptor 2 and fibroblast growth factor receptor 3 genes associated with human gastric and colorectal cancers" *Cancer Research* 61:3541-3543 (May 1, 2001).
Jeffers et al., "Fibroblast growth factors in cancer: therapeutic possibilities" *Expert Opin. Ther. Targets* 6(4):469-482 (2002).

(Continued)

*Primary Examiner* — David Romeo
(74) *Attorney, Agent, or Firm* — Stephanie Yonker

(57) ABSTRACT

The present invention concerns antagonists of the FGF19/FGFR4 pathways, and the uses of same.

14 Claims, 13 Drawing Sheets

OTHER PUBLICATIONS

Junghans et al., "Anti-Tac-H, a Humanized Antibody to the Interleukin 2 Receptor with New Features for Immunotherapy in Malignant and Immune Disorders" *Cancer Research* 50(5):1495-1502 (Mar. 1, 1990).

Kan et al., "Specificity for fibroblast growth factors determined by heparan sulfate in a binary complex with the receptor kinase" *J Biol Chem.* 274(22):15947-15952 (May 28, 1999).

Khazaeli et al., "Phase I trial of multiple large doses of murine monoclonal antibody CO17-1A. II. Pharmacokinetics and immune response" *J Natl Cancer Inst.* 80(12):937-942 (Aug. 17, 1988).

Kiuri-Kuhlefelt et al., "FGF4 and INT2 oncogenes are amplified and expressed in Kaposi's sarcoma" *Mod. Pathol.* 13(4):433-437 (Apr. 2007).

Lin et al., "Liver-specific activities of FGF19 require Klotho beta" *J Biol Chem.* 282(37):27277-84 (Sep. 2007).

Marsh et al., "Increased expression of fibroblast growth factor 8 in human breast cancer" *Oncogene* 18:1053-1060 (1999).

Mattila et al., "FGF-8b increases angiogenic capacity and tumor growth of androgen-regulated S115 breast cancer cells" *Oncogene* 20:2791-2804 (2001).

Miller et al., "Monoclonal antibody therapeutic trials in seven patients with T-cell lymphoma" *Blood* 62:988-995. (1983).

Morimoto et al., "Single nucleotide polymorphism in fibroblast growth factor receptor 4 at codon 388 is associated with prognosis in high-grade soft tissue sarcoma" *Cancer* 98(10):2245-50 (Nov. 15, 2003).

Nicholes et al., "Animal Model: A mouse model of hepatocellular carcinoma ectopic expression of fibroblast growth factor 19 in skeletal muscle of transgenic mice" *American Journal of Pathology* 160(6):2295-2307 (Jun. 2002).

Nishimura et al., "Structure and expression of a novel human FGF, FGF-19, expressed in the fetal brain" *Biochimica et Biophysica Acta* 1444(1):148-151 (Jan. 18, 1999).

Ornitz et al., "Fibroblast growth factors" *Genome Biol.* (REVIEWS3005) 2(3):1-12 (2001).

Ozawa et al., "Expression of the fibroblast growth factor family and their receptor family genes during mouse brain development" *Brain Res Mol Brain Res.* 41(1-2):279-288 (Sep. 5, 1966).

Pai et al., "Inhibition of fibroblast growth factor 19 reduces tumor growth by modulating beta-catenin signaling" *Cancer Research* 68(13):5086-95 (Jul. 2008).

Panka et al., "Variable region framework differences result in decreased or increased affinity of variant anti-digoxin antibodies" *Proc. Natl. Acad. Sci. USA* 85:3080-3084 (May 1988).

Partanen et al., "FGFR-4, a novel acidic fibroblast growth factor receptor with a distinct expression pattern" *EMBO Journal* 10(6):1347-1354 (Jun. 1991).

Penault-Llorca et al., "Expression of FGF and FGF receptor genes in human breast cancer" *Int J Cancer.* 61(2):170-176 (Apr. 10, 1995).

Qian et al., "Cytoplasmic expression of fibroblast growth factor receptor-4 in human pituitary adenomas: relation to tumor type, size, proliferation, and invasiveness" *J Clin Endocrinol Metab.* 89(4):1904-1911 (Apr. 2004).

Reichmann et al., "Reshaping human antibodies for therapy" *Nature* 332:323-327 (Mar. 24, 1988).

Ron et al., "Fibroblast growth factor receptor 4 is a high affinity receptor for both acidic and basic fibroblast growth factor but not for keratinocyte growth factor" *Journal of Biological Chemistry* 268(8):5388-5394 (Mar. 15, 1993).

Rudikoff et al., "Single amino acid substitution altering antigen-binding specificity" *Proc. Natl. Acad. Sci. USA* 79:1979-1983 (Mar. 1982).

Ruohola et al., "Enhanced invasion and tumor growth of fibroblast growth factor 8b-overexpressing MCF-7 human breast cancer cells" *Cancer Research* 61(10):4229-37 (May 2001).

Schlessinger, "Common and distinct elements in cellular signaling via EGF and FGF receptors" *Science* 306(5701):1506-1507 (Nov. 26, 2004).

Sears et al., "Effects of monoclonal antibody immunotherapy on patients with gastrointestinal adenocarcinoma" *J Biol Response Mod.* 3(2):138-150 (1984).

Shawler et al., "Human immune response to multiple injections of murine monoclonal IgG" *J Immunol.* 135(2):1530-1535 (1985).

Shimokawa et al., "Involvement of the FGF18 gene in colorectal carcinogenesis, as a novel downstream target of the beta-catenin/T-cell factor complex" *Cancer Research* 63(19):6116-20 (Oct. 2003).

Spinola et al., "Functional FGFR4 Gly388Arg polymorphism predicts prognosis in lung adenocarcinoma patients" *J Clin Oncol.* 23(29):7307-7311 (Oct. 10, 2005).

Stark et al., "FGFR-4, a new member of the fibroblast growth factor receptor family, expressed in the definitive endoderm and skeletal muscle lineages of the mouse" *Development* 113(2):641-651 (Oct. 1991).

Steiling and Werner, "Fibroblast growth factors: key players in epithelial morphogenesis, repair and cytoprotection" *Curr. Opin. Biotechnol.* 14:533-537 (2003).

Streit et al., "Involvement of the FGFR4 Arg388 allele in head and neck squamous cell carcinoma" *Int J Cancer* 111(2):213-217 (Aug. 20, 2004).

Tomlinson et al., "Transgenic Mice Expressing Human Fibroblast Growth Factor-19 Display Increased Metabolic Rate and Decreased Adiposity" *Endocrinology* 143(5):1741-1747 (May 2002).

Wang et al., "Fibroblast growth factor receptors have different signaling and mitogenic potentials" *Molecular & Cellular Biology* 14(1):181-188 (Jan. 1994).

Xie et al., "FGF-19, a novel fibroblast growth factor with unique specificity for FGFR4" *Cytokine* 11(10):729-735 (Oct. 1999).

Yamada et al., "Fibroblast growth factor receptor (FGFR) 4 correlated with the malignancy of human astrocytomas" *Neurol Res.* 24(3):244-248 (Apr. 2002).

Yu et al., "Elevated cholesterol metabolism and bile acid synthesis in mice lacking membrane tyrosine kinase receptor FGFR4" *J Biol Chem.* 275(20):15482-15489 (May 19, 2000).

| Seq. ID | 93 | | 95 | | 97 | | 98 | | 100 | 100a | 100b | 100c | 101 |
|---|---|---|---|---|---|---|---|---|---|---|---|---|---|
| | V | R | K | E | Y | A | N | L | Y | A | M | D | Y |
| 230 | V | R | K | E | Y | A | N | L | Y | R | M | D | Y |
| 231 | V | R | K | E | Y | A | N | L | Y | K | M | D | Y |
| 232 | V | R | K | E | Y | A | N | L | Y | Q | M | D | Y |
| 233 | V | R | K | E | Y | A | N | L | Y | A | L | D | Y |
| 234 | V | R | K | E | Y | A | N | L | Y | A | M | T | Y |
| 235 | V | R | K | E | Y | A | N | L | Y | A | M | D | H |
| 236 | V | R | K | A | Y | A | N | L | Y | A | M | D | Y |
| 237 | V | R | K | G | Y | A | N | L | Y | A | M | D | Y |
| 238 | V | R | K | E | Y | A | N | L | Y | A | F | H | F |
| 239 | V | R | K | E | Y | A | N | V | Y | A | L | E | Y |
| 240 | V | R | K | E | Y | G | N | L | Y | A | L | N | Y |
| 241 | V | R | K | G | Y | A | S | L | Y | A | M | D | Y |
| 242 | V | R | K | E | Y | A | N | L | Y | A | M | D | Y |
| 243 | V | R | K | E | Y | A | N | L | F | A | M | V | Y |
| 244 | V | R | K | E | Y | A | N | L | Y | E | L | N | H |
| 245 | V | R | K | E | Y | A | K | L | Y | L | M | D | Y |
| 246 | V | R | K | E | Y | A | N | V | Y | M | M | H | Y |
| 247 | V | R | K | E | Y | A | T | L | Y | P | S | A | Y |
| 248 | V | R | K | E | Y | A | N | L | Y | P | S | D | Y |
| 249 | V | R | K | K | Y | A | N | L | Y | P | S | D | Y |
| 250 | V | R | K | E | Y | A | N | V | Y | P | S | D | Y |
| 251 | V | R | K | Q | Y | A | N | L | Y | P | S | D | Y |
| 252 | V | R | K | G | Y | A | F | L | Y | P | S | D | N |
| 253 | V | R | K | G | Y | A | T | L | Y | P | S | Q | F |
| 254 | V | R | K | G | Y | A | S | L | Y | P | S | Q | Y |
| 255 | V | R | K | E | Y | A | N | L | Y | Q | M | D | Y |
| 256 | V | R | K | E | Y | A | N | L | S | Q | M | V | Y |
| 257 | V | R | K | E | Y | A | N | L | Y | R | L | D | F |
| 258 | V | R | K | E | Y | A | N | V | Y | R | M | D | Y |
| 259 | V | R | K | E | Y | A | N | I | Y | T | M | D | Y |
| 260 | V | R | K | E | Y | A | N | V | G | V | M | D | S |

*FIG. 3D*

```
I    A  RVTITADTSTSTAYMELSSLRSEDTAVYYCAR  ┌─────────┐  WGQGTLVTVSS
     B  RVTITADTSTSTAYMELSSLRSEDTAVYYCAR  │ --H3--  │  WGQGTLVTVSS
     C  RVTITADTSTSTAYMELSSLRSEDTAVYYCAR  │ --H3--  │  WGQGTLVTVSS
     D  RVTITADTSTSTAYMELSSLRSEDTAVYYC    │ --H3--  │  WGQGTLVTVSS
                                          └─────────┘

II   A  RVTISVDTSKNQFSLKLSSVTAADTAVYYCAR  ┌─────────┐  WGQGTLVTVSS
     B  RVTISVDTSKNQFSLKLSSVTAADTAVYYCAR  │ --H3--  │  WGQGTLVTVSS
     C  RVTISVDTSKNQFSLKLSSVTAADTAVYYCAR  │ --H3--  │  WGQGTLVTVSS
     D  RVTISVDTSKNQFSLKLSSVTAADTAVYYC    │ --H3--  │  WGQGTLVTVSS
                                          └─────────┘

III  A  RFTISRDNSKNTLYLQMNSLRAEDTAVYYCAR  ┌─────────┐  WGQGTLVTVSS
     B  RFTISRDNSKNTLYLQMNSLRAEDTAVYYCAR  │ --H3--  │  WGQGTLVTVSS
     C  RFTISRDNSKNTLYLQMNSLRAEDTAVYYCAR  │ --H3--  │  WGQGTLVTVSS
     D  RFTISRDNSKNTLYLQMNSLRAEDTAVYYC    │ --H3--  │  WGQGTLVTVSS
                                          └─────────┘

Acceptor
     A  RFTISADTSKNTAYLQMNSLRAEDTAVYYCAR  ┌─────────┐  WGQGTLVTVSS
     B  RFTISADTSKNTAYLQMNSLRAEDTAVYYCAR  │ --H3--  │  WGQGTLVTVSS
     C  RFTISADTSKNTAYLQMNSLRAEDTAVYYCSR  │ --H3--  │  WGQGTLVTVSS
     D  RFTISADTSKNTAYLQMNSLRAEDTAVYYCS   │ --H3--  │  WGQGTLVTVSS
                                          └─────────┘
Second Acceptor
     A  RFTISADTSKNTAYLQMNSLRAEDTAVYYCAR  ┌─────────┐  WGQGTLVTVSS
     B  RFTISADTSKNTAYLQMNSLRAEDTAVYYCAR  │ --H3--  │  WGQGTLVTVSS
     C  RFTISADTSKNTAYLQMNSLRAEDTAVYYCAR  │ --H3--  │  WGQGTLVTVSS
     D  RFTISADTSKNTAYLQMNSLRAEDTAVYYC    │ --H3--  │  WGQGTLVTVSS
                                          └─────────┘
```

FIG. 4B

Framework Sequences of huMAb4D5-8 Light Chain

LC-FR1 $^{1}$Asp Ile Gln Met Thr Gln Ser Pro Ser Ser Leu Ser Ala Ser Val Gly Asp Arg Val Thr Ile Thr Cys$^{23}$ (SEQ ID NO: 42)

LC-FR2 $^{35}$Trp Tyr Gln Gln Lys Pro Gly Lys Ala Pro Lys Leu Leu Ile Tyr$^{49}$ (SEQ ID NO: 43)

LC-FR3 $^{57}$Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys$^{88}$ (SEQ ID NO: 271)

LC-FR4 $^{98}$Phe Gly Gln Gly Thr Lys Val Glu Ile Lys$^{107}$ (SEQ ID NO: 45)

Framework Sequences of huMAb4D5-8 Heavy Chain

HC-FR1 $^{1}$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 46)

HC-FR2 $^{36}$Trp Val Arg Gln Ala Pro Gly Lys Gly Leu Glu Trp Val$^{48}$ (SEQ ID NO: 47)

HC-FR3 $^{66}$Arg Phe Thr Ile Ser Ala Asp Thr Ser Lys Asn Thr Ala Tyr Leu Gln Met Asn$^{83}$ Ser$^{83a}$ Leu$^{83b}$ Arg$^{83c}$ Ala Glu Asp Thr Ala Val Tyr Tyr Cys$^{92}$ (SEQ ID NO: 270)

HC-FR4 $^{103}$Trp Gly Gln Gly Thr Leu Val Thr Val Ser Ser$^{113}$ (SEQ ID NO: 49)

*FIG. 6*

Framework Sequences of huMAb4D5-8 Light Chain Modified at Position 66 (Underlined)

LC-FR1 $^{1}$Asp Ile Gln Met Thr Gln Ser Pro Ser Ser Leu Ser Ala Ser Val Gly Asp Arg Val Thr Ile Thr Cys$^{23}$ (SEQ ID NO: 42)

LC-FR2 $^{35}$Trp Tyr Gln Gln Lys Pro Gly Lys Ala Pro Lys Leu Leu Ile Tyr$^{49}$ (SEQ ID NO: 43)

LC-FR3 $^{57}$Gly Val Pro Ser Arg Phe Ser Gly Ser <u>Gly</u> Ser Gly Thr Asp Phe Thr Leu Thr Ile Ser Ser Leu Gln Pro Glu Asp Phe Ala Thr Tyr Tyr Cys$^{88}$ (SEQ ID NO: 44)

LC-FR4 $^{98}$Phe Gly Gln Gly Thr Lys Val Glu Ile Lys$^{107}$ (SEQ ID NO: 45)

Framework Sequences of huMAb4D5-8 Heavy Chain Modified at Positions 71, 73 and 78 (Underlined)

HC-FR1 $^{1}$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 46)

HC-FR2 $^{36}$Trp Val Arg Gln Ala Pro Gly Lys Gly Leu Glu Trp Val$^{48}$ (SEQ ID NO: 47)

HC-FR3 $^{66}$Arg Phe Thr Ile Ser <u>Arg</u> Asp <u>Asn</u> Ser Lys Asn Thr <u>Leu</u> Tyr Leu Gln Met Asn83 Ser83a Leu83b Arg83c Ala Glu Asp Thr Ala Val Tyr Tyr Cys$^{92}$ (SEQ ID NO: 48)

HC-FR4 $^{103}$Trp Gly Gln Gly Thr Leu Val Thr Val Ser Ser$^{113}$ (SEQ ID NO: 49)

*FIG. 7*

VH
QVQLKQSGPGLVQPSQSLSITCTVSGFSLTTYGVHWVRQSPGKGLEWLGVIWPGGGTDYNAAFI
SRLSITKDNSKSQVFFKMNSLLANDTAIYFCVRKEYANLYAMDYWGQGTLLTVSA
(SEQ ID NO:16)

VL
DIKMTQSPSSMYASLGERVTIPCKASQDINSFLSWFQQKPGKSPKTLIYRANRLVDGVPSRFSG
SGSGQDYSLTISSLEYEDMGIYYCLQYDEFPLTFGAGTKVEIKR
(SEQ ID NO:17)

HUMANIZED ANTI-FGF19 ANTAGONISTS AND METHODS USING SAME

CROSS-REFERENCE TO RELATED APPLICATIONS

This application is a National Stage of International Patent Application No. PCT/US2008/071955, filed Aug. 1, 2008, and claims priority under 35 USC §119 to U.S. Provisional Patent Application No. 60/953,908, filed Aug. 3, 2007, the entire contents of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Sep. 29, 2010, is named P4012R1.txt and is 59,682 bytes in size.

FIELD OF THE INVENTION

The present invention relates generally to the fields of molecular biology. More specifically, the invention concerns antagonists of the FGF19/FGFR4 pathways, and the uses of same.

BACKGROUND OF THE INVENTION

The fibroblast growth factor (FGF) family is composed of 22 structurally related polypeptides that bind to 4 receptor tyrosine kinases (FGFR1-4) and one kinase deficient receptor (FGFR5) (Eswarakumar et al (2005) Cytokine Growth Factor Rev 16, 139-149; Ornitz et al (2001) Genome Biol 2, REVIEWS3005; Sleeman et al (2001) Gene 271, 171-182). FGFs' interaction with FGFR1-4 results in receptor homodimerization and autophosphorylation, recruitment of cytosolic adaptors such as FRS2 and initiation of multiple signaling pathways (Powers et al (2000) Endocr Relat Cancer 7, 165-197; Schlessinger, J. (2004) Science 306, 1506-1507).

FGFs and FGFRs play important roles in development and tissue repair by regulating cell proliferation, migration, chemotaxis, differentiation, morphogenesis and angiogenesis (Ornitz et al (2001) Genome Biol 2, REVIEWS3005; Auguste et al (2003) Cell Tissue Res 314, 157-166; Steiling et al (2003) Curr Opin Biotechnol 14, 533-537). Several FGFs and FGFRs are associated with the pathogenesis of breast, prostate, cervix, stomach and colon cancers (Jeffers et al (2002) Expert Opin Ther Targets 6, 469-482; Mattila et al. (2001) Oncogene 20, 2791-2804; Ruohola et al. (2001) Cancer Res 61, 4229-4237; Marsh et al (1999) Oncogene 18, 1053-1060; Shimokawa et al (2003) Cancer Res 63, 6116-6120; Jang (2001) Cancer Res 61, 3541-3543; Cappellen (1999) Nat Genet. 23, 18-20; Gowardhan (2005) Br J Cancer 92, 320-327).

FGF19 is a member of the most distant of the seven subfamilies of the FGFs. FGF19 is a high affinity ligand of FGFR4 (Xie et al (1999) Cytokine 11:729-735). FGF19 is normally secreted by the biliary and intestinal epithelium. FGF19 plays a role in cholesterol homeostasis by repressing hepatic expression of cholesterol-7-α-hydroxylase 1 (Cyp7α1), the rate-limiting enzyme for cholesterol and bile acid synthesis (Gutierrez et al (2006) Arterioscler Thromb Vasc Biol 26, 301-306; Yu et al (2000) JBiol Chem 275, 15482-15489; Holt, JA, et al. (2003) Genes Dev 17(130): 158). FGF19 ectopic expression in a transgenic mouse model increases hepatocytes proliferation, promotes hepatocellular dysplasia and results in neoplasia by 10 months of age (Nicholes et al. (2002). Am J Pathol 160, 2295-2307). The mechanism of FGF19 induced hepatocellular carcinoma is thought to involve FGFR4 interaction. Treatment with FGF-19 increases metabolic rate and reverses dietary and leptin-deficient diabetes. Fu et al (2004) Endocrinology 145:2594-2603. FGF-19 is also described in, for example, Xie et al. (1999) Cytokine 11:729-735; Harmer et al (2004) Biochemistry 43:629-640; Desnoyer, LR et al, Oncogene (2008) 27(1): 85-97; and Lin, BC et al. (2007) J Biol Chem 282(37):27277-84; Pai, R et al. Cancer Res (2008) 68(13):5086-95.

FGFR4 expression is widely distributed and was reported in developing skeletal muscles, liver, lung, pancreas, adrenal, kidney and brain (Kan et al. (1999) J Biol Chem 274, 15947-15952; Nicholes et al. (2002) Am J Pathol 160, 2295-2307; Ozawa et al. (1996) Brain Res Mol Brain Res 41, 279-288; Stark et al (1991) Development 113, 641-651). FGFR4 amplification was reported in mammary and ovarian adenocarcinomas (Jaakkola et al (1993) Int J Cancer 54, 378-382). FGFR4 mutation and truncation were correlated with the malignancy and in some cases the prognosis of prostate and lung adenocarcinomas, head and neck squamous cell carcinoma, soft tissue sarcoma, astrocytoma and pituitary adenomas (Jaakkola et al (1993) Int J Cancer 54, 378-382; Morimoto (2003) Cancer 98, 2245-2250; Qian (2004) J Clin Endocrinol Metab 89, 1904-1911; Spinola et al. (2005) J Clin Oncol 23, 7307-7311; Streit et al (2004) Int J Cancer 111, 213-217; Wang (1994) Mol Cell Biol 14, 181-188; Yamada (2002) Neurol Res 24, 244-248).

It is clear that there continues to be a need for agents that have clinical attributes that are optimal for development as therapeutic agents. The invention described herein meets this need and provides other benefits.

All references cited herein, including patent applications and publications, are incorporated by reference in their entirety.

SUMMARY OF THE INVENTION

The invention is in part based on the identification of a variety of antagonists of the FGF19/FGFR4 pathway. FGF19 presents as an important and advantageous therapeutic target, and the invention provides compositions and methods based on interfering with FGF19/FGFR4 activation, including but not limited to interfering with FGF19 binding to FGFR4 extracellular domain. Antagonists of the invention, as described herein, provide important therapeutic and diagnostic agents for use in targeting pathological conditions associated with expression and/or activity of the FGF19-FGFR4 pathway. Accordingly, the invention provides methods, compositions, kits and articles of manufacture related to modulating the FGF19/FGFR4 pathway, including modulation of FGF19 receptor binding, activation, and other biological/physiological activities associated with FGF19/FGFR4 signaling.

For example, in one embodiment, the invention provides a humanized anti-FGF19 antibody wherein the monovalent affinity of the antibody to human FGF19 (e.g., affinity of the antibody as a Fab fragment to human FGF19) is substantially the same as the monovalent affinity of a murine antibody (e.g., affinity of the murine antibody as a Fab fragment to human FGF19) or a chimeric antibody (e.g., affinity of the chimeric antibody as a Fab fragment to human FGF19) comprising, consisting or consisting essentially of a light chain and heavy chain variable domain sequence as depicted in FIG. 8. In another embodiment, the invention provides a humanized anti-FGF19 antibody wherein the monovalent affinity of the antibody to human FGF19 (e.g., affinity of the antibody as a Fab fragment to human FGF19) is lower, for example at least 3, 5, 7 or 10-fold lower, than the monovalent affinity of a murine antibody (e.g., affinity of the murine antibody as a Fab fragment to human FGF19) or a chimeric antibody (e.g., affinity of the chimeric antibody as a Fab fragment to human FGF19) comprising, consisting or consisting essentially of a light chain and heavy chain variable domain sequence as depicted in FIG. 8. In another embodiment, the invention provides an anti-FGF19 humanized antibody wherein the monovalent affinity of the antibody to human FGF19 (e.g., affinity of the antibody as a Fab fragment to human FGF19) is greater, for example at least 3, 5, 7, 10 or 13-fold greater, than the monovalent affinity of a murine antibody (e.g., affinity of the murine antibody as a Fab fragment to human FGF19) or a chimeric antibody (e.g., affinity of the chimeric antibody as a Fab fragment to human FGF19) comprising, consisting or consisting essentially of a light chain and heavy chain variable domain sequence as depicted in FIG. 8. As is well-established in the art, binding affinity of a ligand to its receptor can be determined using any of a variety of assays, and expressed in terms of a variety of quantitative values. Accordingly, in one embodiment, the binding affinity is expressed as Kd values and reflects intrinsic binding affinity (e.g., with minimized avidity effects). Generally and preferably, binding affinity is measured in vitro, whether in a cell-free or cell-associated setting. As described in greater detail herein, fold difference in binding affinity can be quantified in terms of the ratio of the monovalent binding affinity value of a humanized antibody (e.g., in Fab form) and the monovalent binding affinity value of a reference/comparator antibody (e.g., in Fab form) (e.g., a murine antibody having donor hypervariable region sequences), wherein the binding affinity values are determined under similar assay conditions. Thus, in one embodiment, the fold difference in binding affinity is determined as the ratio of the Kd values of the humanized antibody in Fab form and said reference/comparator Fab antibody. For example, in one embodiment, if an antibody of the invention (A) has an affinity that is "3-fold lower" than the affinity of a reference antibody (M), then if the Kd value for A is 3×, the Kd value of M would be 1×, and the ratio of Kd of A to Kd of M would be 3:1. Conversely, in one embodiment, if an antibody of the invention (C) has an affinity that is "3-fold greater" than the affinity of a reference antibody (R), then if the Kd value for C is 1×, the Kd value of R would be 3×, and the ratio of Kd of C to Kd of R would be 1:3. Any of a number of assays known in the art, including those described herein, can be used to obtain binding affinity measurements, including, for example, Biacore, radioimmunoassay (RIA) and ELISA.

In one aspect, a FGF19 antagonist of the invention comprises an anti-FGF19 antibody comprising:

(a) at least one, two, three, four or five hypervariable region (HVR) sequences selected from the group consisting of:

(i) HVR-L1 comprising sequence A1-A11, wherein A1-A11 is KASQDINSFLS (SEQ ID NO:1)

(ii) HVR-L2 comprising sequence B1-B7, wherein B1-B7 is RANRLVD (SEQ ID NO:2)

(iii) HVR-L3 comprising sequence C1-C9, wherein C1-C9 is LQYDEFPLT (SEQ ID NO:3)

(iv) HVR-H1 comprising sequence D1-D10, wherein D1-D10 is GFSLTTYGVH (SEQ ID NO:4)

(v) HVR-H2 comprising sequence E1-E17, wherein E1-E17 is XVIWPGGGTDYNAAFIS (SEQ ID NO:5) and X is not G, and (vi) HVR-H3 comprising sequence F1-F13, wherein F1-F13 is XXKEYANLYAMDY (SEQ ID NO:6) and X at position F1 is not V and X at position F2 is not R;

and (b) at least one (such as 1, 2, 3, 4, 5, 6, 7, 8, 9, 10 or more) variant HVR, wherein the variant HVR sequence comprises modification of at least one residue of the sequence depicted in SEQ ID NOs:1, 2, 3, 4, 5 or 6. In one embodiment, HVR-L1 of an antibody of the invention comprises the sequence of SEQ ID NO:1. In one embodiment, HVR-L2 of an antibody of the invention comprises the sequence of SEQ ID NO:2. In one embodiment, HVR-L3 of an antibody of the invention comprises the sequence of SEQ ID NO:3. In one embodiment, HVR-H1 of an antibody of the invention comprises the sequence of SEQ ID NO:4. In one embodiment, HVR-H2 of an antibody of the invention comprises the sequence of SEQ ID NO:5. In one embodiment, HVR-H3 of an antibody of the invention comprises the sequence of SEQ ID NO:6. In one embodiment, HVR-H2 comprises GVIWPGGGTDYNAAFIS (SEQ ID NO: 7). In one embodiment, HVR-H3 comprises VRKEYANLYAMDY (SEQ ID NO: 8). In one embodiment, HVR-H3 comprises VXKEYANLYAMDY (SEQ ID NO: 9), wherein X is not R. In one embodiment, HVR-H3 comprises XRKEYANLYAMDY (SEQ ID NO: 10), wherein X is not V. In one embodiment, HVR-L1 comprises KASQDINSFLA (SEQ ID NO: 11). In one embodiment, HVR-L1 comprises KASQDINSFLG (SEQ ID NO: 12). In one embodiment, HVR-L2 comprises RANRLVS (SEQ ID NO: 13). In one embodiment, HVR-L2 comprises RANRLVE (SEQ ID NO: 14). In one embodiment, an antibody of the invention comprising these sequences (in combination as described herein) is humanized or human. These antibodies are distinct from (i.e. they are not) an antibody described in U.S. patent application Ser. No. 11/673,411, filed Feb. 9, 2007.

In one aspect, the invention provides an antibody comprising one, two, three, four, five or six HVRs, wherein each HVR comprises, consists or consists essentially of a sequence selected from the group consisting of SEQ ID NOs: 1, 2, 3, 4, 5, 6, 7, 8, 9, 10, 11, 12, and 14 and wherein SEQ ID NO:1, 11 and 12 correspond to an HVR-L1, SEQ ID NO:2, 13, and 14 correspond to an HVR-L2, SEQ ID NO:3 corresponds to an HVR-L3, SEQ ID NO:4 corresponds to an HVR-H1, SEQ ID NO:5 or 7 correspond to an HVR-H2, and SEQ ID NOs:6, 8, 9 or 10 correspond to an HVR-H3. In one embodiment, an antibody of the invention comprises HVR-L1, HVR-L2, HVR-L3, HVR-H1, HVR-H2, and HVR-H3, wherein each, in order, comprises SEQ ID NO:1, 2, 3, 4, 7 and 8. In one embodiment, an antibody of the invention comprises HVR-L1, HVR-L2, HVR-L3, HVR-H1, HVR-H2, and HVR-H3, wherein each, in order, comprises SEQ ID NO:1, 2, 3, 4, 7 and 9. In one embodiment, an antibody of the invention comprises HVR-L1, HVR-L2, HVR-L3, HVR-H1, HVR-H2, and HVR-H3, wherein each, in order, comprises SEQ ID NO:1, 2, 3, 4, 7 and 10. In one embodiment, an antibody of the invention comprises HVR-L1, HVR-L2, HVR-L3, HVR-H1, HVR-H2, and HVR-H3, wherein each, in order, comprises SEQ ID NO:1, 11, 3, 4, 7 and 8. In one embodiment, an antibody of the invention comprises HVR-L1, HVR-L2, HVR-L3, HVR-H1, HVR-H2, and HVR-H3, wherein each, in order, comprises SEQ ID NO:1, 12, 3, 4, 7 and 8. In one embodiment, an antibody of the invention comprises HVR-L1, HVR-L2, HVR-L3, HVR-H1, HVR-H2, and HVR-H3, wherein each, in order, comprises SEQ ID NO:1, 11, 13, 4, 7 and 8. In one embodiment, an antibody of the invention comprises HVR-L1, HVR-L2, HVR-L3, HVR-H1, HVR-H2, and HVR-H3, wherein each, in order, comprises SEQ ID NO:1, 12, 13, 4, 7 and 8. In one embodiment, an antibody of the invention comprises HVR-L1, HVR-L2, HVR-L3, HVR-H1, HVR-H2, and HVR-H3, wherein each, in order, comprises SEQ ID NO:1, 11, 14, 4, 7 and 8. In one embodiment, an antibody of the invention comprises HVR-L1, HVR-L2, HVR-L3, HVR-H1, HVR-H2, and HVR-H3, wherein each, in order, comprises SEQ ID NO:1, 12, 14, 4, 7 and 8. In one embodiment, an antibody of the invention comprises HVR-L1, HVR-L2, HVR-L3, HVR-H1, HVR-H2, and HVR-H3, wherein each, in order, comprises SEQ ID NO:1, 11, 13, 4, 7 and 9. In one embodiment, an antibody of the invention comprises HVR-L1, HVR-L2, HVR-L3, HVR-H1, HVR-H2, and HVR-H3, wherein each, in order, comprises SEQ ID NO:1, 11, 13, 4, 7 and 10. In some embodiments, these antibodies further comprise a human subgroup III heavy chain framework consensus sequence. In some embodiment of these antibodies, these antibodies further comprise a human κI light chain framework consensus sequence.

Variant HVRs in an antibody of the invention can have modifications of one or more residues within the HVR.

In one embodiment, a HVR-L1 variant comprises 1-11 (1, 2, 3, 4, 5, 6, 7, 8, 9, 10 or 11) substitutions in any combination of the following positions: A1 (T, S, Q or N), A2 (V, S, L or P), A3 (V, Y, I, R, N, K or Q), A4 (E, L, H, K, R or S), A5 (H, N, G, R, E or Y), A6 (F, L, A, V, K, S or M), A7 (M, K, D, Y or I), A8 (N, A, K, R, Y or I), A9 (S, Y or L), A10 (M, V or I), and A11 (A, G or T).

In one embodiment, a HVR-L2 variant comprises 1-7 (1, 2, 3, 4, 5, 6 or 7) substitutions in any combination of the following positions: B1 (K, G, T, S, Q or H), B2 (T, G or S), B3 (K, S, G, Y, R, E or I), B4 (M, G, Y, H or L), B5 (Q, M, V, I or H), B6 (E, R, M, A, G or P), and B7 (E, A, V, N or G).

In one embodiment, a HVR-L3 variant comprises 1-8 (1, 2, 3, 4, 5, 6, 7 or 8) substitutions in any combination of the following positions: C1 (M or Q), C2 (S, T, N, K, H, E, D or A), C3 (D or F), C4 (S, A, E, G, H, Y, N or V), C5 (G, K, T, D, N, V, Y, A or I), C6 (M), C7 (A), and C9 (S, I or V).

In one embodiment, a HVR-H1 variant comprises 1-8 (1, 2, 3, 4, 5, 6, 7 or 8) substitutions in any combination of the following positions: D2 (Y), D3 (R, G, N or D), D4 (I, V, F or M), D5 (A, I, K, N, R or S), D6 (S or R), D7 (F), D9 (A or G) and D10 (Q or Y).

In one embodiment, a HVR-H2 variant comprises 1-14 (1, 2, 3, 4, 5, 6, 7, 8, 9, 10, 11, 12, 13 or 14) substitutions in any combination of the following positions: E1 (S), E2 (I, L or M), E3 (S, M, V, L, F, Y or T), E6 (A), E8 (A, T, S, Y or R), E9 (I, L, S, V or Y), E10 (E, N, A or H), E11 (E, S, L, F, I, V or W), E12 (G, K, A, T or S), E13 (E, K, S, G, P or T), E14 (R, E, L, G, F, D, T, S or K), E15 (L, V or S), E16 (T, E, N, L, S, V, M, A, T, H, G, D or F), and E17 (T, R, N, G, K, P, A, D or E).

In one embodiment, a HVR-H3 variant comprises 1-9 (1, 2, 3, 4, 5, 6, 7, 8 or 9) substitutions in any combination of the following positions: F4 (A, G, K or Q), F6 (G), F7 (S, K, T or F), F8 (V or I), F9 F, S or G), F10 (R, K, Q, E, L, M, P, T or V), F11 (L, F, A or S), F12 (T, H, E, N, V, A, Q or Y) and F13 (H, F, N or S).

Letter(s) in parenthesis following each position indicates an illustrative substitution (i.e., replacement) amino acid; as would be evident to one skilled in the art, suitability of other amino acids as substitution amino acids in the context described herein can be routinely assessed using techniques known in the art and/or described herein. In one embodiment, A11 in a variant HVR-L1 is T. In one embodiment, A11 in a variant HVR-L1 is A. In one embodiment, B7 in a variant HVR-L2 is S. In one embodiment, B7 in a variant HVR-L2 is G. In one embodiment, A11 in a variant HVR-L1 is T and B7 in a variant HVR-L2 is S. In one embodiment, A11 in a variant HVR-L1 is T and B7 in a variant HVR-L2 is G. In one embodiment, A11 in a variant HVR-L1 is A and B7 in a variant HVR-L2 is S. In one embodiment, A11 in a variant HVR-L1 is T and B7 in a variant HVR-L2 is G. In one embodiment, D9 in a variant HVR-H1 is A. In one embodiment, D10 in a variant HVR-H1 is Q. In one embodiment, E2 in a variant HVR-H2 is L. In one embodiment, F10 in a variant HVR-H3 is R. In one embodiment, F10 in a variant HVR-H3 is R and F11 in the variant HVR-H3 is S.

In some embodiments, these antibodies further comprise a human subgroup III heavy chain framework consensus sequence. In some embodiment of these antibodies, these antibodies further comprise a human KI light chain framework consensus sequence.

In one aspect, the invention provides an antibody comprising one, two, three, four, five or all of the HVR sequences depicted in FIG. 3 (SEQ ID NOs:18 and 52-260).

A therapeutic agent for use in a host subject preferably elicits little to no immunogenic response against the agent in said subject. In one embodiment, the invention provides such an agent. For example, in one embodiment, the invention provides a humanized antibody that elicits and/or is expected to elicit a human anti-mouse antibody response (HAMA) at a substantially reduced level compared to an antibody comprising the heavy and light chain variable regions shown in FIG. 8 in a host subject. In another example, the invention provides a humanized antibody that elicits and/or is expected to elicit minimal or no human anti-mouse antibody response (HAMA). In one example, an antibody of the invention elicits anti-mouse antibody response that is at or less than a clinically-acceptable level.

As is known in the art, and as described in greater detail hereinbelow, the amino acid position/boundary delineating a hypervariable region of an antibody can vary, depending on the context and the various definitions known in the art (as described below). Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions (as further defined below). The invention provides antibodies comprising modifications in these hybrid hypervariable positions.

An antibody of the invention can comprise any suitable human or human consensus light chain framework sequences, provided the antibody exhibits the desired biological characteristics (e.g., a desired binding affinity). In some embodiments, one or more (such as 2, 3, 4, 5, 6, 7, 8, 9, or more) additional modifications are present within the human and/or human consensus non-hypervariable region sequences. In one embodiment, an antibody of the invention comprises at least a portion (or all) of the framework sequence of human κ light chain. In one embodiment, an antibody of the invention comprises at least a portion (or all) of human κ subgroup I framework consensus sequence. In some embodiments, antibodies of the invention comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment, an antibody of the invention comprises a heavy and/or light chain variable domain comprising framework sequence depicted in FIG. 1 and/or FIG. 2, provided position 49 in the heavy chain is not G and/or position 93 in the heavy chain is not V and/or position 94 in the heavy chain is not R.

Some embodiments of antibodies of the invention comprise a light chain variable domain of humanized 4D5 antibody (huMAb4D5-8) (HERCEPTIN®, Genentech, Inc., South San Francisco, CA, USA) (also referred to in U.S. Pat. No. 6,407,213 and Lee et al., J. Mol. Biol. (2004), 340(5): 1073-93) as depicted in SEQ ID NO:269 below.

```
                                          (SEQ ID NO: 269)
1 Asp Ile Gln Met Thr Gln Ser Pro Ser Ser

Leu Ser Ala Ser Val Gly Asp Arg Val Thr Ile

Thr Cys Arg Ala Ser Gln Asp Val Asn Thr Ala

Val Ala Trp Tyr Gln Gln Lys Pro Gly Lys Ala

Pro Lys Leu Leu Ile Tyr Ser Ala Ser Phe Leu

Tyr Ser Gly Val Pro Ser Arg Phe Ser Gly Ser

Arg Ser Gly Thr Asp Phe Thr Leu Thr Ile Ser

Ser Leu Gln Pro Glu Asp Phe Ala Thr Tyr Tyr

Cys Gln Gln His Tyr Thr Thr Pro Pro Thr Phe

Gly Gln Gly Thr Lys Val Glu Ile Lys 107

(HVR residues are underlined)
```

In one embodiment, the huMAb4D5-8 light chain variable domain sequence is modified at one or more of positions 30, 66 and 91 (Asn, Arg and His as indicated in bold/italics above, respectively). In one embodiment, the modified huMAb4D5-8 sequence comprises Ser in position 30, Gly in position 66 and/or Ser in position 91. Accordingly, in one embodiment, an antibody of the invention comprises a light chain variable domain comprising the sequence depicted in SEQ ID NO:15 below:

```
                                           (SEQ ID NO: 15)
1 Asp Ile Gln Met Thr Gln Ser Pro Ser Ser

Leu Ser Ala Ser Val Gly Asp Arg Val Thr Ile

Thr Cys Arg Ala Ser Gln Asp Val Ser Thr Ala

Val Ala Trp Tyr Gln Gln Lys Pro Gly Lys Ala

Pro Lys Leu Leu Ile Tyr Ser Ala Ser Phe Leu

Tyr Ser Gly Val Pro Ser Arg Phe Ser Gly Ser

Gly Ser Gly Thr Asp Phe Thr Leu Thr Ile Ser

Ser Leu Gln Pro Glu Asp Phe Ala Thr Tyr Tyr

Cys Gln Gln Ser Tyr Thr Thr Pro Pro Thr Phe

Gly Gln Gly Thr Lys Val Glu Ile Lys 107

(HVR residues are underlined)
```

Substituted residues with respect to huMAb4D5-8 are indicated in bold/italics above.

In one aspect, an antibody of the invention is a humanized anti-FGF19 antibody that inhibits binding of human FGF19 to FGFR4 substantially the same as a reference antibody (such as a chimeric anti-FGF19 antibody or a murine anti-FGF19 antibody) comprising a light chain and heavy chain variable sequence as depicted in FIG. 8. Comparison of abilities to inhibit FGF19 binding to its receptor can be performed according to various methods known in the art, including as described in the Examples below. In one embodiment, IC50 values are determined across an antibody concentration range from about 0.01 nM to around 1000 nM.

In one aspect, an antibody of the invention is a humanized anti-FGF19 antibody that inhibits human FGFR4 receptor activation substantially the same as a reference antibody (such as a chimeric anti-FGF19 antibody or a murine anti-FGF19 antibody) comprising a light chain and heavy chain variable sequence as depicted in FIG. 7 (SEQ ID NO: 9 and 10). Comparison of abilities to inhibit receptor activation can be performed according to various methods known in the art, including as described in the Examples below. In one embodiment, IC50 values are determined across an antibody concentration range from about 0.1 nM to about 100 nM.

In one embodiment, both the humanized antibody and chimeric antibody are monovalent. In one embodiment, the reference chimeric antibody comprises variable domain sequences depicted in FIG. 8 linked to a human Fc region. In one embodiment, the human Fc region is that of an IgG (e.g., IgG1, 2, 3 or 4).

In one aspect, the invention provides an anti-FGF19 antibody comprising: at least one, two, three, four, five, and/or six hypervariable region (HVR) sequences selected from the group consisting of: (a) HVR-L1 comprising the sequence depicted in SEQ ID NO:1; (b) HVR-L2 comprising the sequence depicted in SEQ ID NO:11; (c) HVR-L3 comprising the sequence depicted in SEQ ID NO:13; (d) HVR-H1 comprising the sequence depicted in SEQ ID NO:4; (e) HVR-H2 comprising the sequence depicted in SEQ ID NO:7; and (f) HVR-H3 comprising the sequence depicted in SEQ ID NO:8.

In one aspect, the invention provides an anti-FGF19 antibody comprising a light chain comprising (a) HVR-L1 comprising the sequence depicted in SEQ ID NO: 1; (b) HVR-L2 comprising the sequence depicted in SEQ ID NO:11; and (c) HVR-L3 comprising the sequence depicted in SEQ ID NO:13.

In one aspect, the invention provides an anti-FGF19 antibody comprising a heavy chain comprising (a) HVR-H1 comprising the sequence depicted in SEQ ID NO:4; (b) HVR-H2 comprising the sequence depicted in SEQ ID NO:7; and (c) HVR-H3 comprising the sequence depicted in SEQ ID NO:8.

In one aspect, the invention provides an anti-FGF19 antibody comprising (a) a light chain comprising (i) HVR-L1 comprising the sequence depicted in SEQ ID NO:1; (ii) HVR-L2 comprising the sequence depicted in SEQ ID NO:11; and (iii) HVR-L3 comprising the sequence depicted in SEQ ID NO:13, and (b) a heavy chain comprising (i) HVR-H1 comprising the sequence depicted in SEQ ID NO:4; (ii) HVR-H2 comprising the sequence depicted in SEQ ID NO:7; and (iii) HVR-H3 comprising the sequence depicted in SEQ ID NO:8.

In some embodiments, these antibodies further comprise a human subgroup III heavy chain framework consensus sequence. In some embodiment of these antibodies, these antibodies further comprise a human KI light chain framework consensus sequence.

The antibodies of the invention may modulate one or more aspects of FGF19- and FGFR4-associated effects, including but not limited to FGF19 binding, FGFR4 activation, FGFR4 downstream molecular signaling, disruption of FGFR4 binding to FGF19, FGFR4 multimerization, expression of a CYP7α1 gene, phosphorylation of FGFR4, MAPK, FRS2 and/or ERK2, activation of β-catenin, FGF19-promoted cell migration, and/or disruption of any biologically relevant FGF19 and/or FGFR4 biological pathway, and/or treatment and/or prevention of a tumor, cell proliferative disorder or a cancer; and/or treatment or prevention of a disorder associated with FGF19 expression and/or activity (such as increased FGF19 expression and/or activity).

In some embodiments, the antibody of the invention specifically binds to FGF19. In some embodiments, the antibody specifically binds FGF19 with a Kd of about 120 μM or stronger. In some embodiments, the antibody specifically binds FGF19 with a Kd of about 140 pM or stronger. In some embodiments, the antibody blocks FGF19 binding to FGFR4 with an IC50 of about 4 nM.

In one aspect, the invention provides an isolated antibody that binds an FGFR4 binding region of FGF19.

In one aspect, the invention provides an isolated anti-FGF19 antibody that inhibits, reduces, and/or blocks FGF19-induced repression of expression of a CYP7α1 gene in a cell exposed to FGF19.

In one aspect, the invention provides an isolated anti-FGF19 antibody that inhibits, reduces, and/or blocks FGF19-induced phosphorylation of FGFR4, MAPK, FRS2 and/or ERK2 in a cell exposed to FGF19.

In one aspect, the invention provides an isolated anti-FGF19 antibody that inhibits, reduces, and/or blocks FGF19-promoted cell migration. In some embodiments, the cell is a tumor cell. In some embodiments, the cell is a tumor cell. In some embodiments, the cell is an HCT116 cell.

In one aspect, the invention provides an isolated anti-FGF19 antibody that inhibits, reduces, and/or blocks Wnt pathway activation in a cell. In some embodiments, Wnt pathway activation comprises one or more of β-catenin immunoreactivity, tyrosine phosphorylation of β-catenin, expression of Wnt target genes, β-catenin mutation, and E-cadherin binding to β-catenin. Detection of Wnt pathway activation is known in the art, and some examples are described and exemplified herein.

In one embodiment, an antibody of the invention specifically binds to FGF19 of a first animal species, and does not specifically bind to FGF19 of a second animal species. In one embodiment, the first animal species is human and/or primate (e.g., cynomolgus monkey), and the second animal species is murine (e.g., mouse) and/or canine. In one embodiment, the first animal species is human. In one embodiment, the first animal species is primate, for example cynomolgus monkey. In one embodiment, the second animal species is murine, for example mouse. In one embodiment, the second animal species is canine.

In some embodiments, the antibody is a monoclonal antibody. In some embodiments, the antibody is a polyclonal antibody. In some embodiments, the antibody is selected from the group consisting of a chimeric antibody, an affinity matured antibody, a humanized antibody, and a human antibody. In some embodiments, the antibody is an antibody fragment. In some embodiments, the antibody is a Fab, Fab', Fab'-SH, F(ab')$_2$, or scFv.

In one aspect, the invention provides an antibody that competes with any of the above-mentioned antibodies for binding to FGF19 (i.e., blocks binding to FGF19 of any of the above-mentioned antibodies). In one aspect, the invention provides an antibody that binds to the same epitope on FGF19 as any of the above-mentioned antibodies.

In other embodiments, the antibodies of the invention further comprise changes in amino acid residues in the Fc region that lead to improved effector function including enhanced CDC and/or ADCC function and B-cell killing. Other antibodies of the invention include those having specific changes that improve stability. In other embodiments, the antibodies of the invention comprise changes in amino acid residues in the Fc region that lead to decreased effector function, e.g. decreased CDC and/or ADCC function and/or decreased B-cell killing. In some embodiments, the antibodies of the invention are characterized by decreased binding (such as absence of binding) to human complement factor C1q and/or human Fc receptor on natural killer (NK) cells. In some embodiments, the antibodies of the invention are characterized by decreased binding (such as the absence of binding) to human FcγRI, FcγRIIA, and/or FcγRIIIA. In some embodiments, the antibodies of the invention is of the IgG class (e.g., IgG1 or IgG4) and comprises at least one mutation in E233, L234, L235, G236, D265, D270, N297, E318, K320, K322, A327, A330, P331 and/or P329 (numbering according to the EU index). In some embodiments, the antibodies comprise the mutation L234A/L235A or D265A/N297A.

In one aspect, the invention provides anti-FGF19 polypeptides comprising any of the antigen binding sequences provided herein, wherein the anti-FGF19 polypeptides specifically bind to FGF19.

In one aspect, the invention provides an immunoconjugate (interchangeably termed "antibody drug conjugate" or "ADC") comprising any of the anti-FGF19 antibodies disclosed herein conjugated to an agent, such as a drug.

In one aspect, the invention provides compositions comprising one or more antibodies of the invention and a carrier. In one embodiment, the carrier is pharmaceutically acceptable.

In another aspect, the invention supplies a composition comprising one or more anti-FGF19 antibodies described herein, and a carrier. This composition may further comprise a second medicament, wherein the antibody is a first medicament. This second medicament, for cancer treatment, for example, may be another antibody, chemotherapeutic agent, cytotoxic agent, anti-angiogenic agent, immunosuppressive agent, prodrug, cytokine, cytokine antagonist, cytotoxic radiotherapy, corticosteroid, anti-emetic cancer vaccine, analgesic, anti-vascular agent, or growth-inhibitory agent. In another embodiment, a second medicament is administered to the subject in an effective amount, wherein the antibody is a first medicament. This second medicament is more than one medicament, and is preferably another antibody, chemotherapeutic agent, cytotoxic agent, anti-angiogenic agent, immunosuppressive agent, prodrug, cytokine, cytokine antagonist, cytotoxic radiotherapy, corticosteroid, anti-emetic, cancer vaccine, analgesic, anti-vascular agent, or growth-inhibitory agent. More specific agents include, for example, irinotecan (CAMPTOSAR®), cetuximab (ERBITUX®), fulvestrant (FASLODEX®), vinorelbine (NAVELBINEO), EFG-receptor antagonists such as erlotinib (TARCEVA®) VEGF antagonists such as bevacizumab (AVASTIN®), vincristine (ONCOVIN®), inhibitors of mTor (a serine/threonine protein kinase) such as rapamycin and CCI-779, and anti-HER1, HER2, ErbB, and/or EGFR antagonists such as trastuzumab (HERCEPTIN®), pertuzumab (OMNITARG™), or lapatinib, and other cytotoxic agents including chemotherapeutic agents. In some embodiments, the second medicament is an anti-estrogen drug such as tamoxifen, fulvestrant, or an aromatase inhibitor, an antagonist to vascular endothelial growth factor (VEGF) or to ErbB or the Efb receptor, or Her-1 or Her-2. In some embodiments, the second medicament is tamoxifen, letrozole, exemestane, anastrozole, irinotecan, cetuximab, fulvestrant, vinorelbine, erlotinib, bevacizumab, vincristine, imatinib, sorafenib, lapatinib, or trastuzumab, and preferably, the second medicament is erlotinib, bevacizumab, or trastuzumab.

In one aspect, the invention provides an anti-idiotype antibody that specifically binds an anti-FGF19 antibody of the invention.

In one aspect, the invention provides nucleic acids encoding an anti-FGF19 antibody of the invention.

In one aspect, the invention provides vectors comprising a nucleic acid of the invention.

In one aspect, the invention provides compositions comprising one or more nucleic acid of the invention and a carrier. In one embodiment, the carrier is pharmaceutically acceptable.

In one aspect, the invention provides host cells comprising a nucleic acid or a vector of the invention. A vector can be of any type, for example a recombinant vector such as an expression vector. Any of a variety of host cells can be used. In one embodiment, a host cell is a prokaryotic cell, for example, E. coli. In one embodiment, a host cell is a eukaryotic cell, for example a mammalian cell such as Chinese Hamster Ovary (CHO) cell.

In one aspect, the invention provides methods of making an antibody of the invention. For example, the invention provides methods of making an anti-FGF19 antibody (which, as defined herein includes full length and fragments thereof), said method comprising expressing in a suitable host cell a recombinant vector of the invention encoding said antibody, and recovering said antibody.

In one aspect, the invention provides an article of manufacture comprising a container; and a composition contained within the container, wherein the composition comprises one or more anti-FGF19 antibodies of the invention. In one embodiment, the composition comprises a nucleic acid of the invention. In one embodiment, a composition comprising an antibody further comprises a carrier, which in some embodiments is pharmaceutically acceptable. In one embodiment, an article of manufacture of the invention further comprises instructions for administering the composition (for e.g., the antibody) to an individual (such as instructions for any of the methods described herein).

In one aspect, the invention provides a kit comprising a first container comprising a composition comprising one or more anti-FGF19 antibodies of the invention; and a second container comprising a buffer. In one embodiment, the buffer is pharmaceutically acceptable. In one embodiment, a composition comprising an antibody further comprises a carrier, which in some embodiments is pharmaceutically acceptable. In one embodiment, a kit further comprises instructions for administering the composition (for e.g., the antibody) to an individual.

In one aspect, the invention provides use of an anti-FGF19 antibody of the invention in the preparation of a medicament for the therapeutic and/or prophylactic treatment of a disorder, such as a cancer, a tumor, and/or a cell proliferative disorder. In some embodiments, the cancer, a tumor, and/or a cell proliferative disorder is colorectal cancer, hepatocellular carcinoma, lung cancer, breast cancer, or pancreatic cancer. In some embodiments, the disorder is a liver disorder, such as cirrhosis. In some embodiments, the disorder is a wasting disorder.

In one aspect, the invention provides use of a nucleic acid of the invention in the preparation of a medicament for the therapeutic and/or prophylactic treatment of a disorder, such as a cancer, a tumor, and/or a cell proliferative disorder. In some embodiments, the cancer, a tumor, and/or a cell proliferative disorder is colorectal cancer, hepatocellular carcinoma, lung cancer, breast cancer, or pancreatic cancer. In some embodiments, the disorder is a liver disorder, such as cirrhosis. In some embodiments, the disorder is a wasting disorder.

In one aspect, the invention provides use of an expression vector of the invention in the preparation of a medicament for the therapeutic and/or prophylactic treatment of a disorder, such as a cancer, a tumor, and/or a cell proliferative disorder. In some embodiments, the cancer, a tumor, and/or a cell proliferative disorder is colorectal cancer, hepatocellular carcinoma, lung cancer, breast cancer, or pancreatic cancer. In some embodiments, the disorder is a liver disorder, such as cirrhosis. In some embodiments, the disorder is a wasting disorder.

In one aspect, the invention provides use of a host cell of the invention in the preparation of a medicament for the therapeutic and/or prophylactic treatment of a disorder, such as a cancer, a tumor, and/or a cell proliferative disorder. In some embodiments, the cancer, a tumor, and/or a cell proliferative disorder is colorectal cancer, hepatocellular carcinoma, lung cancer, breast cancer, or pancreatic cancer. In some embodiments, the disorder is a liver disorder, such as cirrhosis. In some embodiments, the disorder is a wasting disorder.

In one aspect, the invention provides use of an article of manufacture of the invention in the preparation of a medicament for the therapeutic and/or prophylactic treatment of a disorder, such as a cancer, a tumor, and/or a cell proliferative disorder. In some embodiments, the cancer, a tumor, and/or a cell proliferative disorder is colorectal cancer, hepatocellular carcinoma, lung cancer, breast cancer, or pancreatic cancer. In some embodiments, the disorder is a liver disorder, such as cirrhosis. In some embodiments, the disorder is a wasting disorder.

In one aspect, the invention provides use of a kit of the invention in the preparation of a medicament for the therapeutic and/or prophylactic treatment of a disorder, such as a cancer, a tumor, and/or a cell proliferative disorder. In some embodiments, the cancer, a tumor, and/or a cell proliferative disorder is colorectal cancer, hepatocellular carcinoma, lung cancer, breast cancer, or pancreatic cancer. In some embodiments, the disorder is a liver disorder, such as cirrhosis. In some embodiments, the disorder is a wasting disorder.

The invention provides methods and compositions useful for modulating a disease associated with dysregulation of the FGF19/FGFR4 signaling axis (such as modulating disease states associated with expression and/or activity of FGF19 and/or FGFR4), said methods comprising administration of an effective dose of an anti-FGF19 antibody to an individual in need of such treatment.

In one aspect, the invention provides methods for killing a cell (such as a cancer or tumor cell), the methods comprising administering an effective amount of an anti-FGF19 antibody to an individual in need of such treatment.

In one aspect, the invention provides methods for reducing, inhibiting, blocking, or preventing growth of a tumor or cancer, the methods comprising administering an effective amount of an anti-FGF19 antibody to an individual in need of such treatment.

Methods of the invention can be used to affect any suitable pathological state. Exemplary disorders are described herein, and include a cancer selected from the group consisting of esophageal cancer, bladder cancer, lung cancer, ovarian cancer, pancreatic cancer, mammary fibroadenoma, prostate cancer, head and neck squamous cell carcinoma, soft tissue sarcoma, astrocytoma, pituitary cancer, breast cancer, neuroblastomas, melanoma, breast carcinoma, gastric cancer, colorectal cancer (CRC), epithelial carcinomas, brain cancer, endometrial cancer, testis cancer, cholangiocarcinoma, gallbladder carcinoma, and hepatocellular carcinoma.

In one embodiment, a cell that is targeted in a method of the invention is a cancer cell. For example, a cancer cell can be one selected from the group consisting of a breast cancer cell, a colorectal cancer cell, a lung cancer cell, a papillary carcinoma cell, a colon cancer cell, a pancreatic cancer cell, an ovarian cancer cell, a cervical cancer cell, a central nervous system cancer cell, an esophageal cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell, a leukemia cell, a brain cancer cell, a endometrial cancer cell, a testis cancer cell, a cholangiocarcinoma cell, a gallbladder carcinoma cell, a lung cancer cell, and/or a prostate cancer cell. In one embodiment, a cell that is targeted in a method of the invention is a hyperproliferative and/or hyperplastic cell. In one embodiment, a cell that is targeted in a method of the invention is a dysplastic cell. In yet another embodiment, a cell that is targeted in a method of the invention is a metastatic cell.

In one embodiment of the invention, the cell that is targeted is a cirrhotic liver cell.

Methods of the invention can further comprise additional treatment steps. For example, in one embodiment, a method further comprises a step wherein a targeted cell and/or tissue (for e.g., a cancer cell) is exposed to radiation treatment or a chemotherapeutic agent.

BRIEF DESCRIPTION OF THE FIGURES

FIG. 2: depicts alignment of sequences of the variable heavy chain for the following: light chain variable heavy subgroup III consensus sequence (SEQ ID NO:263), murine 1A6 antibody (SEQ ID NO:16) and the 1A6 grafted antibody (SEQ ID NO:264). Positions are numbered according to Kabat.

FIGS. 3A-D: depicts various HVR sequences of selected affinity-matured antibodies from libraries with individually-randomized HVR. HVR-L1: SEQ ID NOS: 1, 18 and 52-86; HVR-L2: SEQ ID NOS: 2, 87-127; HVR-L3: SEQ ID NOS: 3, 128-155; HVR-H1: SEQ ID NOS: 4, 156-176; HVR-H2: SEQ ID NOS: 7, 177-229; AND HVR=H3: SEQ ID NOS: 8, 230-260.

Figure 4A:
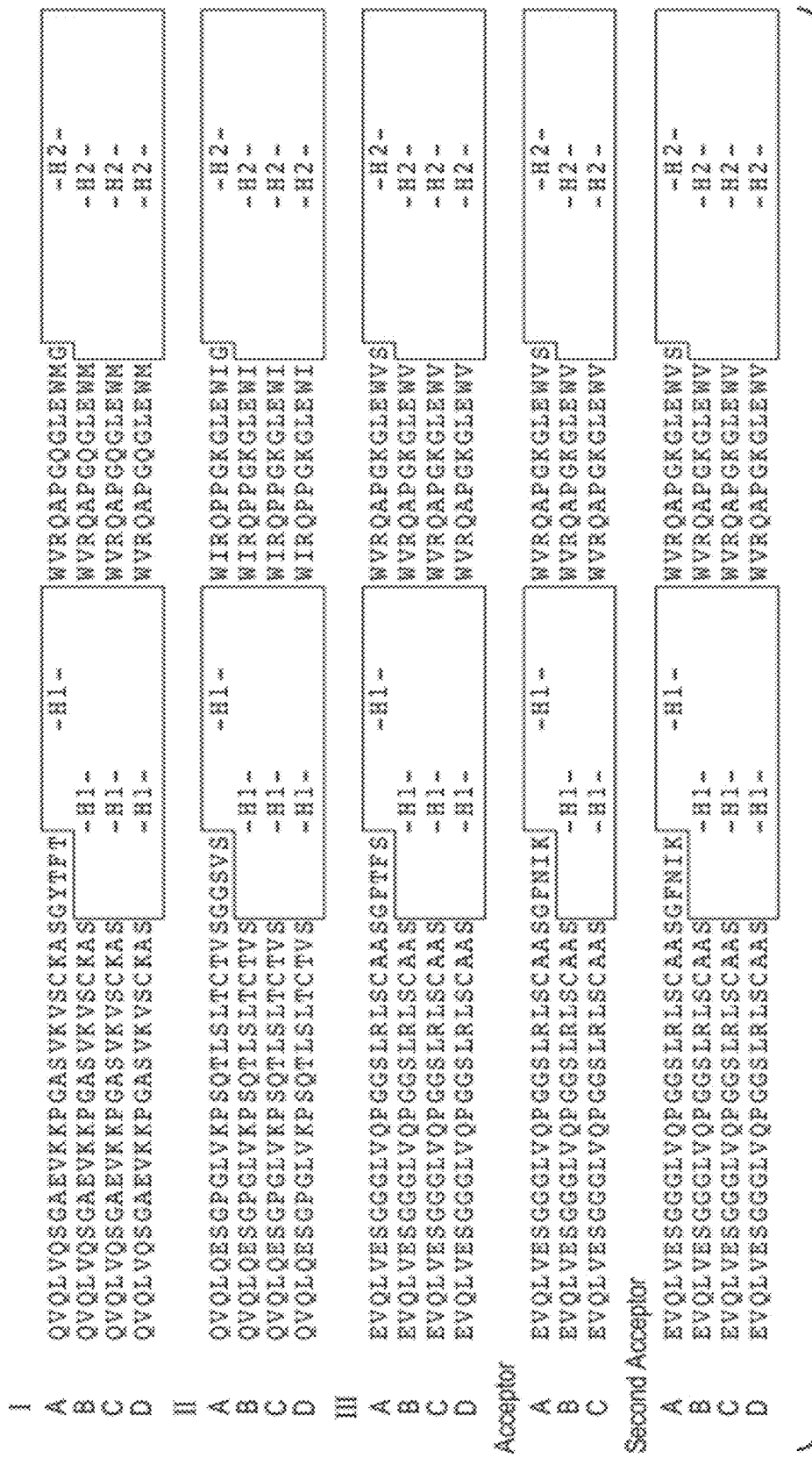
FIGS. 4A,B & 5: depict exemplary acceptor human consensus framework sequences for use in practicing the instant invention with sequence identifiers as follows.

Variable heavy (VH) consensus frameworks (FIG. 4A, B)
human VH subgroup I consensus framework minus Kabat CDRs (SEQ ID NOS 19-21 & 49, respectively, in order of appearance)
human VH subgroup I consensus framework minus extended hypervariable regions (SEQ ID NOS 22-23, 21 & 49; 22-24 & 49; and 22-23, 25 & 49, respectively, in order of appearance)
human VH subgroup II consensus framework minus Kabat CDRs (SEQ ID NOS 26-28 & 49, respectively, in order of appearance)
human VH subgroup II consensus framework minus extended hypervariable regions (SEQ ID N0S 29-30, 28 & 49; 29-31 & 49; and 29-30, 32 & 49, respectively, in order of appearance)
human VH subgroup III consensus framework minus Kabat CDRs (SEQ ID NOS 33-35 & 49, respectively, in order of appearance)
human VH subgroup III consensus framework minus extended hypervariable regions (SEQ ID NOS 46-47, 35 & 49; 46-47, 36 & 49; and 46-49, respectively, in order of appearance)
human VH acceptor framework minus Kabat CDRs (SEQ ID NOS 37, 34, 268 & 49, respectively, in order of appearance)
human VH acceptor framework minus extended hypervariable regions (SEQ ID NOS 46-47, 268 & 49 and 46-47, 267 & 49, respectively, in order of appearance)
human VH acceptor 2 framework minus Kabat CDRs (SEQ ID NOS 37, 34, 266 & 49, respectively, in order of appearance)
human VH acceptor 2 framework minus extended hypervariable regions (SEQ ID NOS 46-47, 266 & 49; 46-47, 265 & 49; and 46-47, 270 & 49, respectively, in order of appearance)

Figure 5:
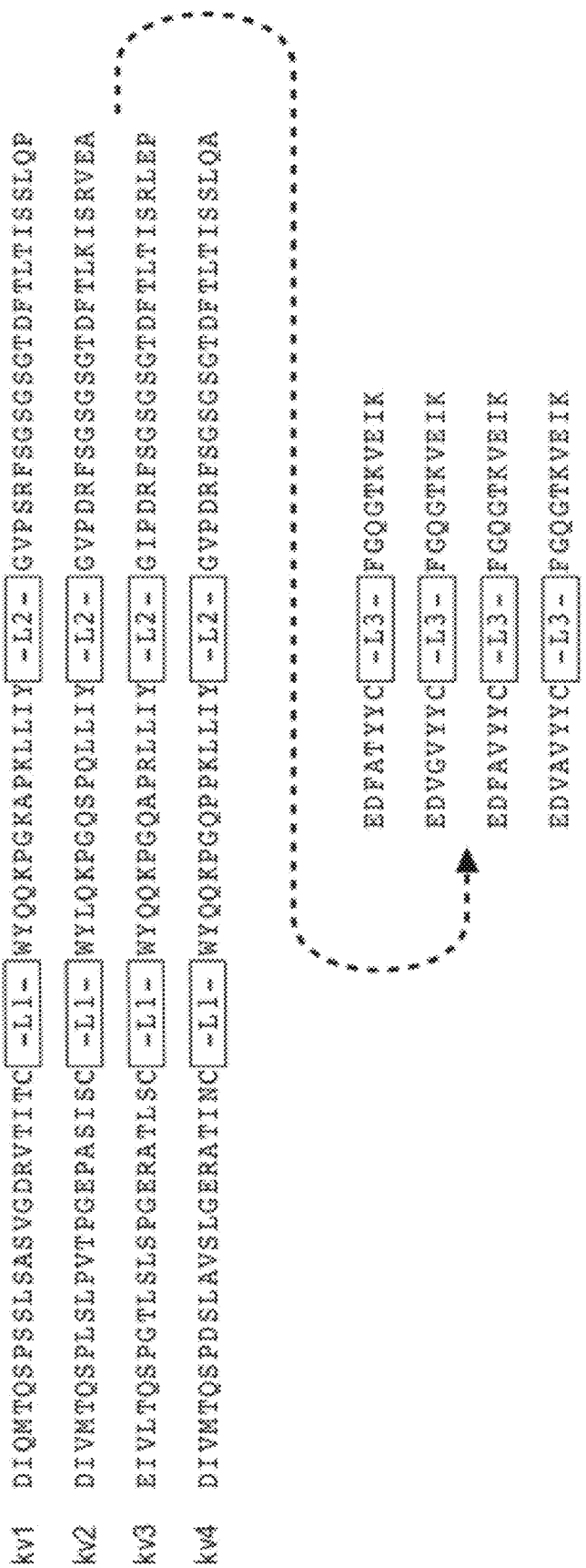

Variable light (VL) consensus frameworks (FIG. 5)
human VL kappa subgroup I consensus framework (SEQ ID NOS 42-45, respectively, in order of appearance)
human VL kappa subgroup II consensus framework (SEQ ID NOS 38-40 & 45, respectively, in order of appearance)
human VL kappa subgroup III consensus framework (SEQ ID NOS 41, 272-273 & 45, respectively, in order of appearance)
human VL kappa subgroup IV consensus framework (SEQ ID NOS 274-276 & 45, respectively, in order of appearance)

FIG. 6: depicts framework region sequences of huMAb4D5-8 light and heavy chains. Numbers in superscript/bold indicate amino acid positions according to Kabat.

FIG. 7: depicts modified/variant framework region sequences of huMAb4D5-8 light and heavy chains. Numbers in superscript/bold indicate amino acid positions according to Kabat.

Figures 8, 9:
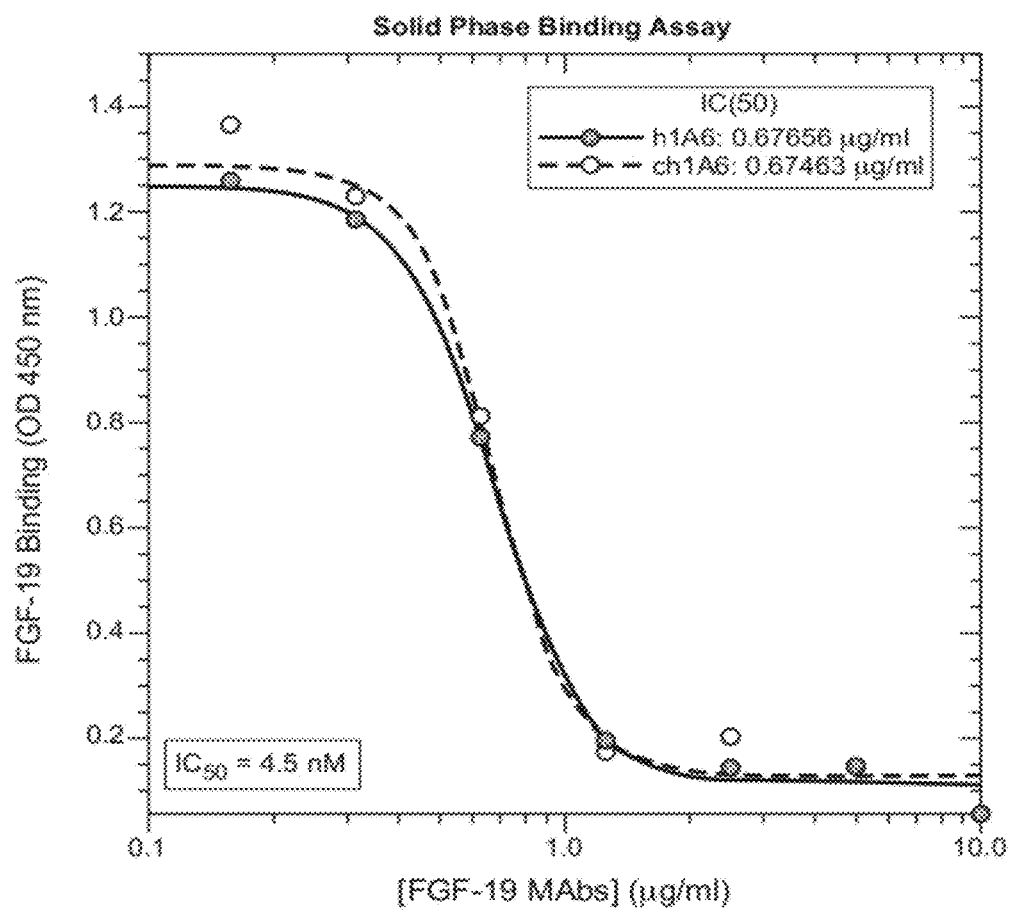

FIG. 8: depicts donor (murine antibody 1A6) light chain (LC) and heavy chain (HC) variable domain sequences.

FIG. 9: Humanized anti-FGF19 antibody 1A6.v1 ("h1A6") and chimeric anti-FGF19 antibody 1A6 ("ch1A6") demonstrated similar blocking activity. In a solid phase receptor binding assay, hu1A6 and ch1A6 blocked FGF19 interaction with FGFR4 with the same efficacy (IC50=4.5 nM).

Figure 10A:
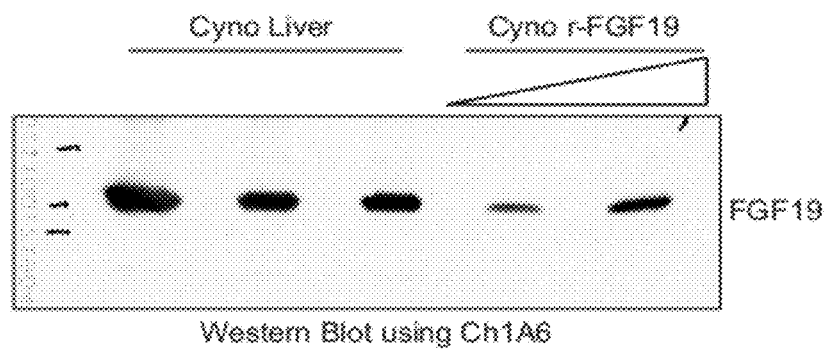
Figure 10B:
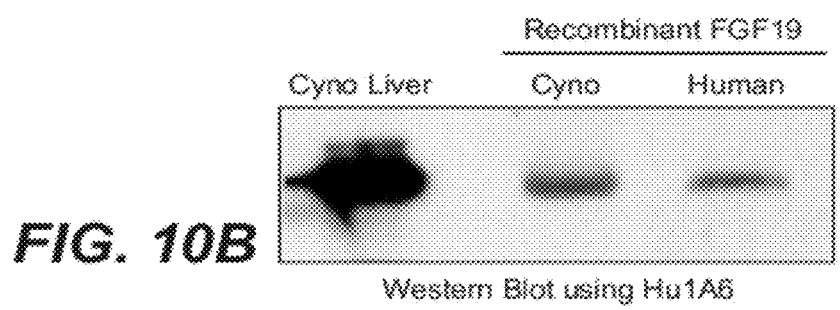

FIG. 10: Western blot analysis of FGF19 expression in human and cynomolgus liver. (A) Humanized anti-FGF19 antibody 1A6.v1 ("hu1A6") bound to human and cynomolgus FGF19. (B) Humanized anti-FGF19 antibody 1A6.v1 recognized recombinant huFGF19, recombinant cynoFGF19 and cynoFGF19 proteins isolated from the liver.

Figure 11:
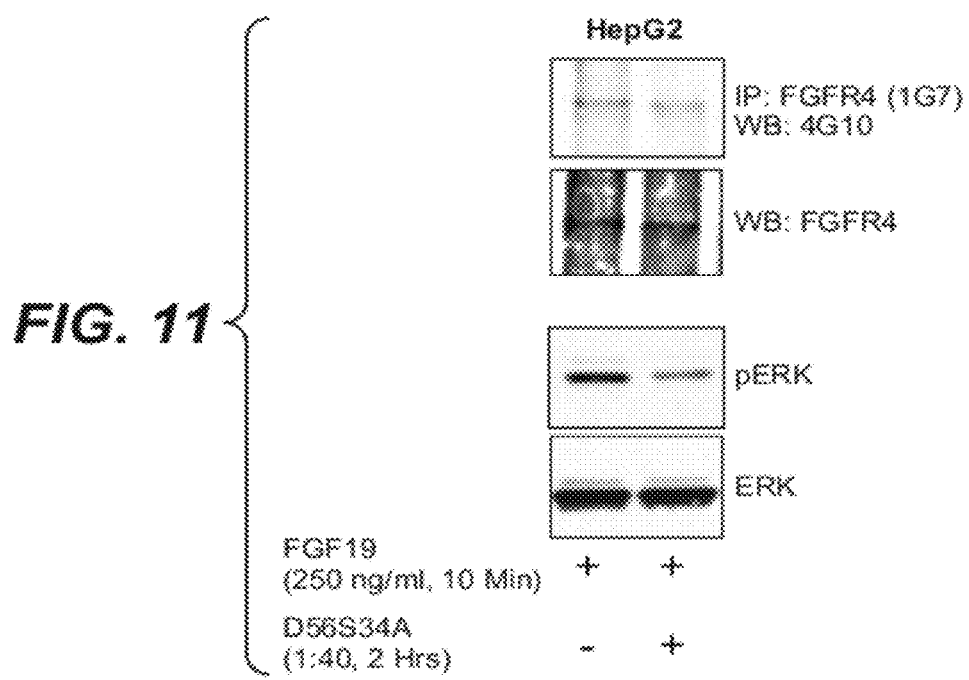

FIG. 11: Treatment with humanized anti-FGF10 antibody 1A6.v1 inhibited FGFR4, FRS2 and ERK phosphorylation in vitro. Phosphorylation of FGFR4, FRS2, and ERK was inhibited in humanized anti-FGF19 antibody 1A6.v1-treated HCT116 colon tumor cell.

Figure 12A:
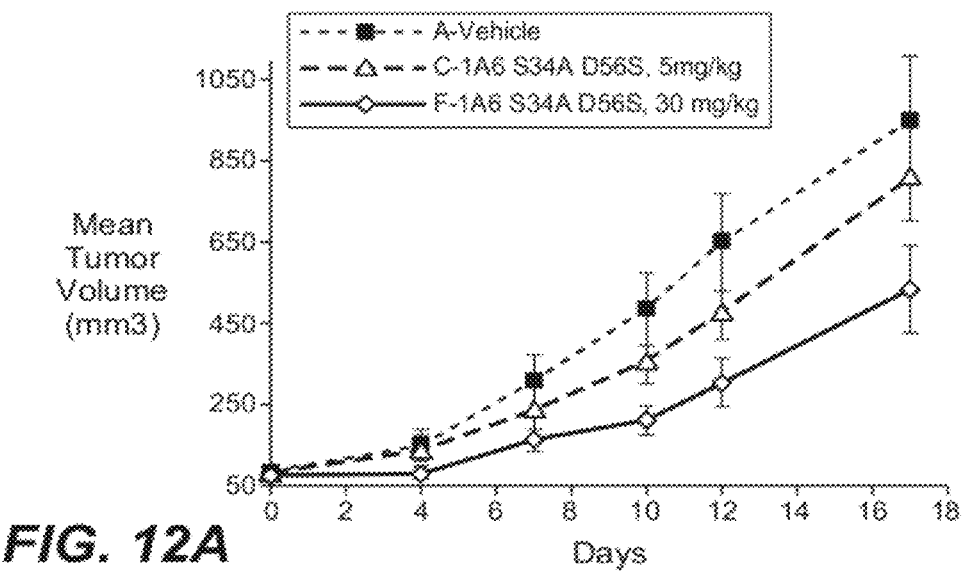
Figure 12B:
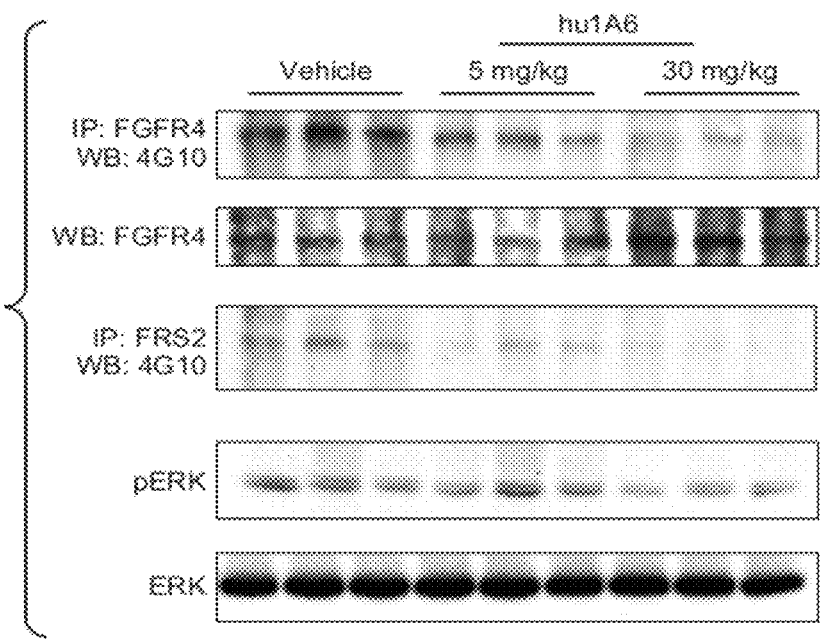

FIG. 12: Treatment with humanized anti-FGF19 antibody 1A6.v1 inhibited colon tumor cell line growth in vivo. (A) Growth of HCT116 colon tumor xenografts was significantly inhibited by treatment with 30 mg/kg of 1A6.v1 compared to control antibody (p=0.042). A 44% inhibition of tumor growth was observed when animals were treated with 30 mg/kg of 1A6.v1. (B) Phosphorylation of FGFR4, FRS2, and ERK was inhibited in humanized anti-FGF19 antibody 1A6.v1-treated HCT116 xenograft tumors.

DETAILED DESCRIPTION OF THE INVENTION

The invention provides methods, compositions, kits and articles of manufacture for identifying and/or using inhibitors of the FGF19/FGFR4 signaling pathway.

Details of these methods, compositions, kits and articles of manufacture are provided herein.

General Techniques

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Definitions

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "anti-FGF19 antibody" or "an antibody that binds to FGF19" refers to an antibody that is capable of binding FGF19 with sufficient affinity such that the antibody is useful as a diagnostic and/or therapeutic agent in targeting FGF19. Preferably, the extent of binding of an anti-FGF19 antibody to an unrelated, non-FGF19 protein is less than about 10% of the binding of the antibody to FGF19 as measured, e.g., by a radioimmunoassay (RIA). In certain embodiments, an antibody that binds to FGF19 has a dissociation constant (Kd) of $\leq 1$ μM, $\leq 100$ nM, $\leq 10$ nM, $\leq 1$ nM, or $\leq 0.1$ nM. In certain embodiments, an anti-FGF19 antibody binds to an epitope of FGF19 that is conserved among FGF19 from different species.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol Biol 293: 865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 μM or 26 pM [$^{125}$I]-antigen antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25 C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) J. Mol Biol 293:865-881. If the on-rate exceeds $10^6$ M$^{-1}$ S$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (Thermo-Spectronic) with a stirred cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25 C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneously fitting the association and dissociation sensorgram. The equilibrium dissociation constant (Kd) was calculated as the ratio $k_{off}/k_{on}$. See, e.g., Chen, Y., et al., (1999) J. Mol Biol 293:865-881. However, if the on-rate exceeds $10^6 M^{-1} S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a a spectrometer, such as a stop-flow equipped spectrophometer (Aviv Instruments) or a 8000-series SLM-Aminco spectrophotometer (ThermoSpectronic) with a stirred cuvette.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The term "FGF19" (interchangeably termed "Fibroblast growth factor 19"), as used herein, refers, unless specifically or contextually indicated otherwise, to any native or variant (whether native or synthetic) FGF19 polypeptide. The term "native sequence" specifically encompasses naturally occurring truncated or secreted forms (e.g., an extracellular domain sequence), naturally occurring variant forms (e.g., alternatively spliced forms) and naturally-occurring allelic variants.

The term "wild type FGF19" generally refers to a polypeptide comprising the amino acid sequence of a naturally occurring FGF19 protein. The term "wild type FGF19 sequence" generally refers to an amino acid sequence found in a naturally occurring FGF19.

The term "FGFR4" (interchangeably termed "Fibroblast growth factor receptor 4"), as used herein, refers, unless specifically or contextually indicated otherwise, to any native or variant (whether native or synthetic) FGFR4 polypeptide. The term "native sequence" specifically encompasses naturally occurring truncated or secreted forms (e.g., an extracellular domain sequence), naturally occurring variant forms (e.g., alternatively spliced forms) and naturally-occurring allelic variants. The term "wild type FGFR4" generally refers to a polypeptide comprising the amino acid sequence of a naturally occurring FGFR4 protein. The term "wild type FGFR4 sequence" generally refers to an amino acid sequence found in a naturally occurring FGFR4.

The terms "antibody" and "immunoglobulin" are used interchangeably in the broadest sense and include monoclonal antibodies (for e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (HVRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three HVRs, which form loops connecting, and in some cases forming part of, the β-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For e.g., such an antibody fragment may comprise on antigen binding arm linked to an Fc sequence capable of conferring in vivo stability to the fragment.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in *The Pharmacology of Monoclonal Antibodies*, vol. 113, Rosenburg and Moore eds., Springer-Verlag, New York, pp. 269-315 (1994).

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is a polypeptide.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993). Triabodies and tetrabodies are also described in Hudson et al., *Nat. Med.* 9:129-134 (2003).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic; challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies may be produced using certain procedures known in the art. For example, Marks et al. *Bio/Technology* 10:779-783 (1992) describes affinity maturation by VH and VL domain shuffling. Random mutagenesis of HVR and/or framework residues is described by, for example, Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody," as used herein, is an antibody which partially or fully mimics at least one of the functional activities of a polypeptide of interest.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology*, 15(7):637-640 (1997); Hinton et al., *J. Biol. Chem.* 279(8):6213-6216 (2004); WO 2004/92219 (Hinton et al.).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. *J. Biol. Chem.* 9(2):6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *PNAS (USA)* 95:652-656 (1998).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. *J. Immunol.* 164: 4178-4184 (2000).

The term "Fc region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, a composition comprising an antibody having an Fc region according to this invention can comprise an antibody with K447, with all K447 removed, or a mixture of antibodies with and without the K447 residue.

An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

A "VH subgroup III consensus framework" comprises the consensus sequence obtained from the amino acid sequences in variable heavy subgroup III of Kabat et al. In one embodiment, the VH subgroup III consensus framework amino acid sequence comprises at least a portion or all of each of the following sequences:

| | |
|---|---|
| EVQLVESGGGLVQPGGSLRLSCAAS | (SEQ ID NO: 46)- |
| H1-WVRQAPGKGLEWV | (SEQ ID NO: 47)- |
| H2-RFTISRDNSKNTLYLQMNSLRAEDTAVYYC | (SEQ ID NO: 48)- |
| H3-WGQGTLVTVSS. | (SEQ ID NO: 49) |

A "VL subgroup I consensus framework" comprises the consensus sequence obtained from the amino acid sequences in variable light kappa subgroup I of Kabat et al. In one embodiment, the VH subgroup I consensus framework amino acid sequence comprises at least a portion or all of each of the following sequences:

| | |
|---|---|
| DIQMTQSPSSLSASVGDRVTITC | (SEQ ID NO: 42)- |
| L1-WYQQKPGKAPKLLIY | (SEQ ID NO: 43)- |
| L2-GVPSRFSGSGSGTDFTLTISSLQPEDFATYYC | (SEQ ID NO: 44)- |
| L3-FGQGTKVEIK. | (SEQ ID NO: 45) |

A "biological sample" (interchangeably termed "sample" or "tissue or cell sample") encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments, the biological sample is obtained from a primary or metastatic tumor. The biological sample may contain compounds which are not naturally intermixed with the tissue in nature such as preservatives, anticoagulants, buffers, fixatives, nutrients, antibiotics, or the like.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention. In some embodiments, the same section of tissue sample is analyzed at both morphological and molecular levels, or is analyzed with respect to both protein and nucleic acid.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

A "medicament" is an active drug to treat the disorder in question or its symptoms, or side effects.

A "disorder" or "disease" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; carcinoma, blastoma, and sarcoma.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all precancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer. Dysregulation of angiogenesis can lead to many disorders that can be treated by compositions and methods of the invention. These disorders include both non-neoplastic and neoplastic conditions. Neoplastics include but are not limited those described above. Non-neoplastic disorders include but are not limited to undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

The term "wasting" disorders (e.g., wasting syndrome, cachexia, sarcopenia) refers to a disorder caused by undesirable and/or unhealthy loss of weight or loss of body cell mass. In the elderly as well as in AIDS and cancer patients, wasting disease can result in undesired loss of body weight, including both the fat and the fat-free compartments. Wasting diseases can be the result of inadequate intake of food and/or metabolic changes related to illness and/or the aging process. Cancer patients and AIDS patients, as well as patients following extensive surgery or having chronic infections, immunologic diseases, hyperthyroidism, Crohn's disease, psychogenic disease, chronic heart failure or other severe trauma, frequently suffer from wasting disease which is sometimes also referred to as cachexia, a metabolic and, sometimes, an eating disorder. Cachexia is additionally characterized by hypermetabolism and hypercatabolism. Although cachexia and wasting disease are frequently used interchangeably to refer to wasting conditions, there is at least one body of research which differentiates cachexia from wasting syndrome as a loss of fat-free mass, and particularly, body cell mass (Mayer, 1999, J. Nutr. 129(1S Suppl.):2565-2595). Sarcopenia, yet another such disorder which can affect the aging individual, is typically characterized by loss of muscle mass. End stage wasting disease as described above can develop in individuals suffering from either cachexia or sarcopenia.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, antibodies of the invention are used to delay development of a disease or disorder.

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. For example, an anti-angiogenesis agent is an antibody or other antagonist to an angiogenic agent as defined above, e.g., antibodies to VEGF, antibodies to VEGF receptors, small molecules that block VEGF receptor signaling (e.g., PTK787/ZK2284, SU6668, SUTENT/SU11248 (sunitinib malate), AMG706). Anti-angiogensis agents also include native angiogenesis inhibitors, e.g., angiostatin, endostatin, etc. See, e.g., Klagsbrun and D'Amore, Annu Rev. Physiol., 53:217-39 (1991); Streit and Detmar, Oncogene, 22:3172-3179 (2003) (e.g., Table 3 listing anti-angiogenic therapy in malignant melanoma); Ferrara & Alitalo, Nature Medicine 5(12):1359-1364 (1999); Tonini et al., Oncogene, 22:6549-6556 (2003) (e.g., Table 2 listing antiangiogenic factors); and, Sato Int. J. Clin. Oncol., 8:200-206 (2003) (e.g., Table 1 lists Anti-angiogenic agents used in clinical trials).

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

"Mammal" for purposes of treatment refers to any animal classified as a mammal, including humans, domestic and farm animals, and zoo, sports, or pet animals, such as dogs, horses, cats, cows, etc. Preferably, the mammal is human.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "toxin" is any substance capable of having a detrimental effect on the growth or proliferation of a cell.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem. Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chlorambucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyl-transferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

A "growth inhibitory agent" when used herein refers to a compound or composition which inhibits growth of a cell (such as a cell expressing FGF19) either in vitro or in vivo. Thus, the growth inhibitory agent may be one which significantly reduces the percentage of cells (such as a cell expressing FGF19) in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "Fc region-comprising polypeptide" refers to a polypeptide, such as an antibody or immunoadhesin (see definitions below), which comprises an Fc region. The C-terminal lysine (residue 447 according to the EU numbering system) of the Fc region may be removed, for example, during purification of the polypeptide or by recombinant engineering the nucleic acid encoding the polypeptide. Accordingly, a composition comprising a polypeptide having an Fc region according to this invention can comprise polypeptides with K447, with all K447 removed, or a mixture of polypeptides with and without the K447 residue.

Generating Variant Antibodies Exhibiting Reduced or Absence of HAMA Response

Reduction or elimination of a HAMA response is a significant aspect of clinical development of suitable therapeutic agents. See, e.g., Khaxzaeli et al., J. Natl. Cancer Inst. (1988), 80:937; Jaffers et al., Transplantation (1986), 41:572; Shawler et al., J. Immunol. (1985), 135:1530; Sears et al., J. Biol. Response Mod. (1984), 3:138; Miller et al., Blood (1983), 62:988; Hakimi et al., J. Immunol. (1991), 147:1352; Reichmann et al., Nature (1988), 332:323; Junghans et al., Cancer Res. (1990), 50:1495. As described herein, the invention provides antibodies that are humanized such that HAMA response is reduced or eliminated. Variants of these antibodies can further be obtained using routine methods known in the art, some of which are further described below.

For example, an amino acid sequence from an antibody as described herein can serve as a starting (parent) sequence for diversification of the framework and/or hypervariable sequence(s). A selected framework sequence to which a starting hypervariable sequence is linked is referred to herein as an acceptor human framework. While the acceptor human frameworks may be from, or derived from, a human immunoglobulin (the VL and/or VH regions thereof), preferably the acceptor human frameworks are from, or derived from, a human consensus framework sequence as such frameworks have been demonstrated to have minimal, or no, immunogenicity in human patients.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor.

In one embodiment, human consensus frameworks herein are from, or derived from, VH subgroup III and/or VL kappa subgroup I consensus framework sequences.

Thus, the VH acceptor human framework may comprise one, two, three or all of the following framework sequences:

FR1 comprising EVQLVESGGGLVQPGGSLRLSCAAS (SEQ ID NO:46),

FR2 comprising WVRQAPGKGLEWV (SEQ ID NO:47),

FR3 comprising FR3 comprises RFTISX1DX2SKNTX3YLQMNSLRAEDTAVYYC (SEQ ID NO:50), wherein X1 is A or R, X2 is T or N, and X3 is A or L, FR4 comprising WGQGTLVTVSS (SEQ ID NO:49).

Examples of VH consensus frameworks include:

human VH subgroup I consensus framework minus Kabat CDRs (SEQ ID NOS 19-21 & 49, respectively, in order of appearance)

human VH subgroup I consensus framework minus extended hypervariable regions (SEQ ID NOS 22-23, 21 & 49; 22-24 & 49; and 22-23, 25 & 49, respectively, in order of appearance)

human VH subgroup II consensus framework minus Kabat CDRs (SEQ ID NOS 26-28 & 49, respectively, in order of appearance)

human VH subgroup II consensus framework minus extended hypervariable regions (SEQ ID NOS 29-30, 28 & 49; 29-31 & 49; and 29-30, 32 & 49, respectively, in order of appearance)

human VH subgroup III consensus framework minus Kabat CDRs (SEQ ID NOS 33-35 & 49, respectively, in order of appearance)

human VH subgroup III consensus framework minus extended hypervariable regions (SEQ ID NOS 46-47, 35 & 49; 46-47, 36 & 49; and 46-48 & 49, respectively, in order of appearance)

human VH acceptor framework minus Kabat CDRs (SEQ ID NOS 37, 34, 268 & 49, respectively, in order of appearance)

human VH acceptor framework minus extended hypervariable regions (SEQ ID N0S 46-47, 268 & 49 and 46-47, 267 & 49, respectively, in order of appearance)

human VH acceptor 2 framework minus Kabat CDRs (SEQ ID NOS 37, 34, 266 & 49, respectively, in order of appearance)

human VH acceptor 2 framework minus extended hypervariable regions (SEQ ID NOS 46-47, 266 & 49; 46-47, 265 & 49; and 46-47, 270 & 49, respectively, in order of appearance)

In one embodiment, the VH acceptor human framework comprises one, two, three or all of the following framework sequences:

FR1 comprising EVQLVESGGGLVQPGGSLRLSCAAS (SEQ ID NO:46),

FR2 comprising WVRQAPGKGLEWV (SEQ ID NO:47),

FR3 comprising RFTISADTSKNTAYLQMNSLRAEDTAVYYC (SEQ ID NO:270),
RFTISADTSKNTAYLQMNSLRAEDTAVYYCA (SEQ ID NO:265),
RFTISADTSKNTAYLQMNSLRAEDTAVYYCAR (SEQ ID NO:266),
RFTISADTSKNTAYLQMNSLRAEDTAVYYCS (SEQ ID NO:267), or
RFTISADTSKNTAYLQMNSLRAEDTAVYYCSR (SEQ ID NO:268)

FR4 comprising WGQGTLVTVSS (SEQ ID NO:49).

The VL acceptor human framework may comprise one, two, three or all of the following framework sequences:
FR1 comprising DIQMTQSPSSLSASVGDRVTITC (SEQ ID NO:42),
FR2 comprising WYQQKPGKAPKLLIY (SEQ ID NO:43),
FR3 comprising GVPSRFSGSGSGTDFTLTISSLQPEDFATYYC (SEQ ID NO:44),
FR4 comprising FGQGTKVEIK (SEQ ID NO:45).
Examples of VL consensus frameworks include:
human VL kappa subgroup I consensus framework (SEQ ID NOS 42-45, respectively, in order of appearance)
human VL kappa subgroup II consensus framework (SEQ ID NOS 38-40 & 45, respectively, in order of appearance)
human VL kappa subgroup III consensus framework (SEQ ID NOS 41, 272-273 & 45, respectively, in order of appearance) human VL kappa subgroup IV consensus framework (SEQ ID NOS 274-276 & 45, respectively, in order of appearance)

While the acceptor may be identical in sequence to the human framework sequence selected, whether that is from a human immunoglobulin or a human consensus framework, the present invention contemplates that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

Hypervariable region residues of the non-human antibody are incorporated into the VL and/or VH acceptor human frameworks. For example, one may incorporate residues corresponding to the Kabat CDR residues, the Chothia hypervariable loop residues, the Abm residues, and/or contact residues. Optionally, the extended hypervariable region residues as follows are incorporated: 24-34 (L1), 50-56 (L2) and 89-97 (L3), 26-35 (H1), 50-65 or 49-65 (H2) and 93-102, 94-102, or 95-102 (H3).

While "incorporation" of hypervariable region residues is discussed herein, it will be appreciated that this can be achieved in various ways, for example, nucleic acid encoding the desired amino acid sequence can be generated by mutating nucleic acid encoding the mouse variable domain sequence so that the framework residues thereof are changed to acceptor human framework residues, or by mutating nucleic acid encoding the human variable domain sequence so that the hypervariable domain residues are changed to non-human residues, or by synthesizing nucleic acid encoding the desired sequence, etc.

In the examples herein, hypervariable region-grafted variants were generated by Kunkel mutagenesis of nucleic acid encoding the human acceptor sequences, using a separate oligonucleotide for each hypervariable region. Kunkel et al., *Methods Enzymol.* 154:367-382 (1987). Appropriate changes can be introduced within the framework and/or hypervariable region, using routine techniques, to correct and re-establish proper hypervariable region-antigen interactions.

Phage(mid) display (also referred to herein as phage display in some contexts) can be used as a convenient and fast method for generating and screening many different potential variant antibodies in a library generated by sequence randomization. However, other methods for making and screening altered antibodies are available to the skilled person.

Phage(mid) display technology has provided a powerful tool for generating and selecting novel proteins which bind to a ligand, such as an antigen. Using the techniques of phage (mid) display allows the generation of large libraries of protein variants which can be rapidly sorted for those sequences that bind to a target molecule with high affinity. Nucleic acids encoding variant polypeptides are generally fused to a nucleic acid sequence encoding a viral coat protein, such as the gene III protein or the gene VIII protein. Monovalent phagemid display systems where the nucleic acid sequence encoding the protein or polypeptide is fused to a nucleic acid sequence encoding a portion of the gene III protein have been developed. (Bass, S., *Proteins,* 8:309 (1990); Lowman and Wells, *Methods: A Companion to Methods in Enzymology,* 3:205 (1991)). In a monovalent phagemid display system, the gene fusion is expressed at low levels and wild type gene III proteins are also expressed so that infectivity of the particles is retained. Methods of generating peptide libraries and screening those libraries have been disclosed in many patents (e.g. U.S. Pat. No. 5,723,286, U.S. Pat. No. 5,432,018, U.S. Pat. No. 5,580,717, U.S. Pat. No. 5,427,908 and U.S. Pat. No. 5,498,530).

Libraries of antibodies or antigen binding polypeptides have been prepared in a number of ways including by altering a single gene by inserting random DNA sequences or by cloning a family of related genes. Methods for displaying antibodies or antigen binding fragments using phage(mid) display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with the desired characteristics.

Methods of substituting an amino acid of choice into a template nucleic acid are well established in the art, some of which are described herein. For example, hypervariable region residues can be substituted using the Kunkel method. See, e.g., Kunkel et al., *Methods Enzymol.* 154:367-382 (1987).

The sequence of oligonucleotides includes one or more of the designed codon sets for the hypervariable region residues to be altered. A codon set is a set of different nucleotide triplet sequences used to encode desired variant amino acids. Codon sets can be represented using symbols to designate particular nucleotides or equimolar mixtures of nucleotides as shown in below according to the IUB code.

IUB Codes
G Guanine
A Adenine
T Thymine
C Cytosine
R (A or G)
Y (C or T)
M (A or C)
K (G or T)
S (C or G)
W (A or T)
H (A or C or T)
B (C or G or T)
V (A or C or G)
D (A or G or T)
N (A or C or G or T)

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Lys, Ser, Arg, Asp, Glu, Gly, and Cys.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis. This technique is well known in the art as described by Zoller et al. *Nucleic Acids Res.* 10:6487-6504 (1987). Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., *Proc. Nat'l. Acad. Sci. USA,* 75:5765 (1978).

The DNA template is generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.,* 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as *E. coli* JM101. After growing the cells, they are plated onto agarose plates and screened using the oligonucleotide primer radiolabelled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. *Meth. Enzymol.*, 153:3 (1987). Thus, the DNA that is to be mutated must be inserted into one of these vectors in order to generate single-stranded template. Production of the single-stranded template is described in sections 4.21-4.41 of Sambrook et al., supra.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

The sequence of the PCR primers includes one or more of the designed codon sets for the solvent accessible and highly diverse positions in a hypervariable region. As described above, a codon set is a set of different nucleotide triplet sequences used to encode desired variant amino acids.

Antibody selectants that meet the desired criteria, as selected through appropriate screening/selection steps can be isolated and cloned using standard recombinant techniques.

Antibody Fragments

The present invention encompasses antibody fragments. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Fab and $F(ab')_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering*, ed. Borrebaeck, supra. The antibody fragment may also be a "linear antibody", e.g., as described in U.S. Pat. No. 5,641,870, for example. Such linear antibodies may be monospecific or bispecific.

Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies. See, e.g., Carter et al. (1992) *Proc. Natl. Acad. Sci. USA*, 89:4285; Presta et al. (1993) *J. Immunol.*, 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human antibodies of the invention can be constructed by combining Fv clone variable domain sequence(s) selected from human-derived phage display libraries with known human constant domain sequences(s) as described above. Alternatively, human monoclonal antibodies of the invention can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90: 2551 (1993); Jakobovits et al., *Nature*, 362: 255 (1993); Bruggermann et al., *Year in Immunol.*, 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by HVR grafting, this technique provides completely human antibodies, which have no FR or HVR residues of non-human origin.

Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for FGF19 and the other is for any other antigen. In certain embodiments, bispecific antibodies may bind to two different epitopes of FGF19. Bispecific antibodies may also be used to localize cytotoxic agents to cells which express FGF19. These antibodies possess a FGF19-binding arm and an arm which binds a cytotoxic agent, such as, e.g., saporin, anti-interferon-α, vinca alkaloid, ricin A chain, methotrexate or radioactive isotope hapten. Bispecific antibodies can be prepared as full length antibodies or antibody fragments (e.g. F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature*, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.*, 10: 3655 (1991).

According to a different approach, antibody variable domains with the desired binding specificities (antibody-antigen combining sites) are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1), containing the site necessary for light chain binding, is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach, the interface between a pair of antibody molecules can be engineered to maximize the percentage of heterodimers which are recovered from recombinant cell culture. The interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking method. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-dized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker that is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. (1997) *TIBTECH* 15:26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

For example, antibody variants are provided having a carbohydrate structure that lacks fucose attached (directly or indirectly) to an Fc region. Such variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336: 1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, an antibody variant comprises an Fc region with one or more amino acid substitutions which further improve ADCC, for example, substitutions at positions 298, 333, and/or 334 of the Fc region (Eu numbering of residues). Such substitutions may occur in combination with any of the variations described above.

In certain embodiments, the invention contemplates an antibody variant that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). Non-limiting examples of in vitro assays to assess ADCC activity of a molecule of interest is described in U.S. Pat. No. 5,500,362 (see, e.g. Hellstrom, I., et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. To assess complement activation, a CDC assay may be performed (see, for example, Gazzano-Santoro et al., *J. Immunol. Methods* 202: 163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, for example, Petkova, S. B. et al., *Int'l. Immunol.* 18(12):1759-1769 (2006)).

Other antibody variants having one or more amino acid substitutions are provided. Sites of interest for substitutional mutagenesis include the hypervariable regions, but FR alterations are also contemplated. Conservative substitutions are shown in Table 1 under the heading of "preferred substitutions." More substantial changes, denominated "exemplary substitutions" are provided in Table 1, or as further described below in reference to amino acid classes. Amino acid substitutions may be introduced into an antibody of interest and the products screened, e.g., for a desired activity, such as improved antigen binding, decreased immunogenicity, improved ADCC or CDC, etc.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Modifications in the biological properties of an antibody may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. An exemplary substitutional variant is an affinity matured antibody, which may be conveniently generated using phage display-based affinity maturation techniques. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and variants with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter, *Nature* 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. *J. Biol. Chem.* 9(2): 6591-6604 (2001). Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al. *J. Immunol.* 164: 4178-4184 (2000).

In another aspect, the invention provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

In yet another aspect, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region.

Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, polypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Activity Assays

The antibodies of the present invention can be characterized for their physical/chemical properties and biological functions by various assays known in the art.

In one aspect, assays are provided for identifying anti-19 antibodies thereof having biological activity. Biological activity may include, e.g., the modulation of one or more aspects of FGF19-associated effects, including but not limited to FGF19 binding, FGFR4 activation, FGFR4 downstream molecular signaling, disruption of FGFR4 binding to FGF19, FGFR4 multimerization, expression of a CYP7α1 gene, phosphorylation of FGFR4, MAPK, FRS2 and/or ERK2, activation of β-catenin, FGF19-promoted cell migration, and/or disruption of any biologically relevant FGF19 and/or FGFR4 biological pathway, and/or treatment and/or prevention of a tumor, cell proliferative disorder or a cancer; and/or treatment or prevention of a disorder associated with FGF19 expression and/or activity (such as increased FGF19 expression and/or activity).

In certain embodiments, an antibody of the invention is tested for its ability to inhibit, reduce, and/or block FGF19-induced repression of expression of a CYP7α1 gene in a cell exposed to FGF19, using methods known in the art, e.g., as described in co-owned U.S. patent application Ser. No. 11/673,411, filed Feb. 9, 2007. In certain embodiments, an antibody of the invention is tested for its ability to inhibit, reduce, and/or block FGF19-induced phosphorylation of FGFR4, MAPK, FRS2 and/or ERK2 in a cell exposed to FGF19, using methods known in the art (e.g., as described in co-owned U.S. patent application Ser. No. 11/673,411, filed Feb. 9, 2007) or exemplified herein. In certain embodiments, an antibody of the invention is tested for its ability to inhibit, reduce, and/or block FGF19-promoted cell (e.g., a tumor cell, e.g., an HCT116 cell) migration, using methods known in the art (e.g., as described in co-owned U.S. patent application Ser. No. 11/673,411, filed Feb. 9, 2007). In certain embodiments, an antibody of the invention is tested for its ability to inhibit, reduce, and/or block Wnt pathway activation in a cell. In some embodiments, Wnt pathway activation comprises one or more of β-catenin immunoreactivity, tyrosine phosphorylation of β-catenin, expression of Wnt target genes, β-catenin mutation, and E-cadherin binding to β-catenin. Detection of Wnt pathway activation is known in the art, and some examples are described and exemplified in, e.g., co-owned U.S. patent application Ser. No. 11/673,411, filed Feb. 9, 2007.

In one aspect, an antibody of the invention is tested for its antigen binding activity, e.g., by known methods such as ELISA, Western blot, etc. In some embodiments, an antibody of the invention is tested for its ability to block FGF19 binding to FGFR4, for example as exemplified herein. In another aspect, competition assays may be used to identify a monoclonal antibody that competes with any of the anti-FGF19 antibodies described herein for binding to FGF19. In certain embodiments, such a competing antibody binds to the same epitope (e.g., a linear or a conformational epitope) that is bound by any of the anti-FGF19 antibodies described herein. Exemplary competition assays include, but are not limited to, routine assays such as those provided in Harlow and Lane (1988) *Antibodies: A Laboratory Manual* ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in *Methods in Molecular Biology* vol. 66 (Humana Press, Totowa, N.J.). Two antibodies are said to bind to the same epitope if each blocks binding of the other by 50% or more.

In an exemplary competition assay, immobilized FGF19 is incubated in a solution comprising a first labeled antibody that binds to FGF19 and a second unlabeled antibody that is being tested for its ability to compete with the first antibody for binding to FGF19. The second antibody may be present in a hybridoma supernatant. As a control, immobilized FGF19 is incubated in a solution comprising the first labeled antibody but not the second unlabeled antibody. After incubation under conditions permissive for binding of the first antibody to FGF19, excess unbound antibody is removed, and the amount of label associated with immobilized FGF19 is measured. If the amount of label associated with immobilized FGF19 is substantially reduced in the test sample relative to the control sample, then that indicates that the second antibody is competing with the first antibody for binding to FGF19.

The purified immunoglobulins can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the immunoglobulins produced herein are analyzed for their biological activity. In some embodiments, the immunoglobulins of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. An illustrative antigen binding assay is provided below in the Examples section.

The purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the antibodies produced herein are analyzed for their biological activity. In some embodiments, the antibodies of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. Illustrative antigen binding assay are provided below in the Examples section.

In some embodiments, the present invention contemplates altered antibodies that possess some but not all effector functions, which make it a desired candidate for many applications in which the half life of the antibody in vivo is important yet certain effector functions (such as complement and ADCC) are unnecessary or deleterious. In certain embodiments, the Fc activities of the produced immunoglobulin are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu Rev. Immunol 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to confirm that the antibody is unable to bind C1q and hence lacks CDC activity. To assess complement activation, a CDC assay, e.g. as described in Gazzano-Santoro et al., J. Immunol. Methods 202:163 (1996), may be performed. FcRn binding and in vivo clearance/half life determinations can also be performed using methods known in the art.

In some embodiments, the invention provides altered antibodies that possess increased effector functions and/or increased half-life.

Vectors, Host Cells and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

a. Generating Antibodies Using Prokaryotic Host Cells:
i. Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, lpp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB− strains) provide cytoplasm conditions that are favorable for disulfide bond formation, thereby permitting proper folding and assembly of expressed protein subunits. Proba and Pluckthun Gene, 159:203 (1995).

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli*λ, 1776 (ATCC 31,537) and *E. coli* RV308(ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

ii. Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41 kD cell wall protein from *Staphylococcus aureas* which binds with a high affinity to the Fc region of antibodies. Lindmark et al (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

b. Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

(v) Enhancer Element Component

Transcription of DNA encoding the antibody polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. No. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Immunoconjugates

The invention also provides immunoconjugates (interchangeably referred to as "antibody-drug conjugates," or "ADCs") comprising an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

Immunoconjugates have been used for the local delivery of cytotoxic agents, i.e., drugs that kill or inhibit the growth or proliferation of cells, in the treatment of cancer (Lambert, J. (2005) *Curr. Opinion in Pharmacology* 5:543-549; Wu et al (2005) *Nature Biotechnology* 23(9):1137-1146; Payne, G. (2003) i 3:207-212; Syrigos and Epenetos (1999) *Anticancer Research* 19:605-614; Niculescu-Duvaz and Springer (1997) *Adv. Drug Deliv. Rev.* 26:151-172; U.S. Pat. No. 4,975,278). Immunoconjugates allow for the targeted delivery of a drug moiety to a tumor, and intracellular accumulation therein, where systemic administration of unconjugated drugs may result in unacceptable levels of toxicity to normal cells as well as the tumor cells sought to be eliminated (Baldwin et al., *Lancet* (Mar. 15, 1986) pp. 603-05; Thorpe (1985) "Antibody Carriers Of Cytotoxic Agents In Cancer Therapy: A Review," in *Monoclonal Antibodies '84: Biological And Clinical Applications* (A. Pinchera et al., eds) pp. 475-506. Both polyclonal antibodies and monoclonal antibodies have been reported as useful in these strategies (Rowland et al., (1986) *Cancer Immunol. Immunother.* 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791), maytansinoids (EP 1391213; Liu et al., (1996) *Proc. Natl. Acad. Sci. USA* 93:8618-8623), and calicheamicin (Lode et al (1998) *Cancer Res.* 58:2928; Hinman et al (1993) *Cancer Res.* 53:3336-3342). The toxins may exert their cytotoxic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and 111In or 90Y radioisotope bound by a thiourea linker-chelator (Wiseman et al (2000) *Eur. Jour. Nucl. Med.* 27(7):766-77; Wiseman et al (2002) *Blood* 99(12):4336-42; Witzig et al (2002) *J. Clin. Oncol.* 20(10):2453-63; Witzig et al (2002) *J. Clin. Oncol.* 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody-drug conjugate composed of a huCD33 antibody linked to calicheamicin, was approved in 2000 for the treatment of acute myeloid leukemia by injection (*Drugs of the Future* (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody-drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and other cancers. MLN-2704 (Millennium Pharm., BZL Biologics, Immunogen Inc.), an antibody-drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) *Nature Biotechnol.* 21(7):778-784) and are under therapeutic development.

In certain embodiments, an immunoconjugate comprises an antibody and a chemotherapeutic agent or other toxin. Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

Maytansine and Maytansinoids

In some embodiments, the immunoconjugate comprises an antibody (full length or fragments) conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses 3×10$^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and non-patent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Auristatins and Dolastatins

In some embodiments, the immunoconjugate comprises an antibody conjugated to dolastatins or dolastatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 1 5:859-863. See also Doronina (2003) Nat Biotechnol 21(7):778-784; "Monomethylvaline Compounds Capable of Conjugation to Ligands", U.S. Ser. No. 10/983, 340, filed Nov. 5, 2004, hereby incorporated by reference in its entirety (disclosing, e.g., linkers and methods of preparing monomethylvaline compounds such as MMAE and MMAF conjugated to linkers).

Calicheamicin

In other embodiments, the immunoconjugate comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma 1I$, $\alpha 2I$, $\alpha 3I$, N-acetyl-$\gamma 1I$, PSAG and $\theta I1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99}m$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds expressly contemplate, but are not limited to, ADC prepared with cross-linker reagents: BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC), an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab\text{-}(L\text{-}D)_p \qquad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC"), and N-Succinimidyl (4-iodo-acetyl) aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Pharmaceutical Formulations

Therapeutic formulations comprising an antibody of the invention are prepared for storage by mixing the antibody having the desired degree of purity with optional physiologically acceptable carriers, excipients or stabilizers (*Remington: The Science and Practice of Pharmacy* 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington: The Science and Practice of Pharmacy* 20th edition (2000).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the present invention may be used in, for example, in vitro, ex vivo and in vivo therapeutic methods.

The invention provides methods and compositions useful for modulating disease states associated with expression and/or activity of FGF19 and/or FGFR4, such as increased expression and/or activity or undesired expression and/or activity, said methods comprising administration of an effective dose of an anti-FGF19 antibody to an individual in need of such treatment. In some embodiments, the disease state is associated with increased expression of FGF19, and the disease state comprises cholestasis or dysregulation of bile acid metabolism.

In one aspect, the invention provides methods for treating or preventing a tumor, a cancer, and/or a cell proliferative disorder, the methods comprising administering an effective amount of an anti-FGF19 antibody to an individual in need of such treatment.

In one aspect, the invention provides methods for treating or preventing a tumor, a cancer, and/or a cell proliferative disorder associated with increased expression and/or activity of FGF19, the methods comprising administering an effective amount of an anti-FGF19 antibody to an individual in need of such treatment.

In one aspect, the invention provides methods for treating or preventing a tumor, a cancer, and/or a cell proliferative disorder associated with increased expression and/or activity of FGFR4, the methods comprising administering an effective amount of an anti-FGF19 antibody to an individual in need of such treatment.

In one aspect, the invention provides methods for treating and/or preventing a liver disorder, the methods comprising administering an effective amount of an anti-FGF19 antibody to an individual in need of such treatment. In some embodiments, the liver disorder is cirrhosis.

In one aspect, the invention provides methods for treating and/or preventing a wasting disorder, the methods comprising administering an effective amount of an anti-FGF19 antibody to an individual in need of such treatment. In some embodiments, the individual has a tumor, a cancer, and/or a cell proliferative disorder.

It is understood that any suitable anti-FGF19 antibody may be used in methods of treatment, including monoclonal and/ or polyclonal antibodies, a human antibody, a chimeric antibody, an affinity-matured antibody, a humanized antibody, and/or an antibody fragment. In some embodiments, any anti-FGF19 antibody described herein is used for treatment.

Moreover, at least some of the antibodies of the invention can bind antigen from other species. Accordingly, the antibodies of the invention can be used to bind specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse). In one embodiment, the antibody of the invention can be used for inhibiting antigen activities by contacting the antibody with the antigen such that antigen activity is inhibited. Preferably, the antigen is a human protein molecule.

In one embodiment, an antibody of the invention can be used in a method for binding an antigen in an individual suffering from a disorder associated with increased antigen expression and/or activity, comprising administering to the subject an antibody of the invention such that the antigen in the subject is bound. Preferably, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the immunoglobulin cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration).

The antibodies of the invention can be used to treat, inhibit, delay progression of, prevent/delay recurrence of, ameliorate, or prevent diseases, disorders or conditions associated with expression and/or activity of one or more antigen molecules.

In certain embodiments, an immunoconjugate comprising an antibody conjugated with one or more cytotoxic agent(s) is administered to the patient. In some embodiments, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell. In one embodiment, the cytotoxic agent targets or interferes with microtubule polymerization. Examples of such cytotoxic agents include any of the chemotherapeutic agents noted herein (such as a maytansinoid, auristatin, dolastatin, or a calicheamicin), a radioactive isotope, or a ribonuclease or a DNA endonuclease.

In any of the methods herein, one may administer to the subject or patient along with the antibody herein an effective amount of a second medicament (where the antibody herein is a first medicament), which is another active agent that can treat the condition in the subject that requires treatment. For instance, an antibody of the invention may be co-administered with another antibody, chemotherapeutic agent(s) (including cocktails of chemotherapeutic agents), anti-angiogenic agent(s), immunosuppressive agents(s), cytokine(s), cytokine antagonist(s), and/or growth-inhibitory agent(s). The type of such second medicament depends on various factors, including the type of disorder, such as cancer or an autoimmune disorder, the severity of the disease, the condition and age of the patient, the type and dose of first medicament employed, etc.

Where an antibody of the invention inhibits tumor growth, for example, it may be particularly desirable to combine it with one or more other therapeutic agents that also inhibit tumor growth. For instance, an antibody of the invention may be combined with an anti-angiogenic agent, such as an anti-VEGF antibody (e.g., AVASTIN®) and/or anti-ErbB antibodies (e.g. HERCEPTIN® trastuzumab anti-HER2 antibody or an anti-HER2 antibody that binds to Domain II of HER2, such as OMNITARG™ pertuzumab anti-HER2 antibody) in a treatment scheme, e.g. in treating any of the disease described herein, including colorectal cancer, lung cancer, hepatocellular carcinoma, breast cancer and/or pancreatic cancer. Alternatively, or additionally, the patient may receive combined radiation therapy (e.g. external beam irradiation or therapy with a radioactive labeled agent, such as an antibody). Such combined therapies noted above include combined administration (where the two or more agents are included in the same or separate formulations), and separate administration, in which case, administration of the antibody of the invention can occur prior to, and/or following, administration of the adjunct therapy or therapies. In addition, combining an antibody of this invention with a relatively non-cytotoxic agent such as another biologic molecule, e.g., another antibody is expected to reduce cytotoxicity versus combining the antibody with a chemotherapeutic agent of other agent that is highly toxic to cells.

Treatment with a combination of the antibody herein with one or more second medicaments preferably results in an improvement in the signs or symptoms of cancer. For instance, such therapy may result in an improvement in survival (overall survival and/or progression-free survival) relative to a patient treated with the second medicament only (e.g., a chemotherapeutic agent only), and/or may result in an objective response *(partial or complete, preferably complete). Moreover, treatment with the combination of an antibody herein and one or more second medicament(s) preferably results in an additive, and more preferably synergistic (or greater than additive), therapeutic benefit to the patient. Preferably, in this combination method the timing between at least one administration of the second medicament and at least one administration of the antibody herein is about one month or less, more preferably, about two weeks or less.

For treatment of cancers, the second medicament is preferably another antibody, chemotherapeutic agent (including cocktails of chemotherapeutic agents), anti-angiogenic agent, immunosuppressive agent, prodrug, cytokine, cytokine antagonist, cytotoxic radiotherapy, corticosteroid, antiemetic, cancer vaccine, analgesic, anti-vascular agent, and/or growth-inhibitory agent. The cytotoxic agent includes an agent interacting with DNA, the antimetabolites, the topoisomerase I or II inhibitors, or the spindle inhibitor or stabilizer agents (e.g., preferably vinca alkaloid, more preferably selected from vinblastine, deoxyvinblastine, vincristine, vindesine, vinorelbine, vinepidine, vinfosiltine, vinzolidine and vinfunine), or any agent used in chemotherapy such as 5-FU, a taxane, doxorubicin, or dexamethasone.

In another embodiment, the second medicament is another antibody used to treat cancers such as those directed against the extracellular domain of the HER2/neu receptor, e.g., trastuzumab, or one of its functional fragments, pan-HER inhibitor, a Src inhibitor, a MEK inhibitor, or an EGFR inhibitor (e.g., an anti-EGFR antibody (such as one inhibiting the tyrosine kinase activity of the EGFR), which is preferably the mouse monoclonal antibody 225, its mouse-man chimeric derivative C225, or a humanized antibody derived from this antibody 225 or derived natural agents, dianilinophthalimides, pyrazolo- or pyrrolopyridopyrimidines, quinazilines, gefitinib, erlotinib, cetuximab, ABX-EFG, canertinib, EKB-569 and PKI-166), or dual-EGFR/HER-2 inhibitor such as lapatanib. Additional second medicaments include alemtuzumab (CAMPATH™), FavID (IDKLH), CD20 antibodies with altered glycosylation, such as GA-101/GLYCART™, oblimersen (GENASENSE™), thalidomide and analogs thereof, such as lenalidomide (REVLIMID™), imatinib, sorafenib, ofatumumab (HUMAX-CD20™), anti-CD40 antibody, e.g. SGN-40, and anti-CD-80 antibody, e.g. galiximab.

The anti-emetic agent is preferably ondansetron hydrochloride, granisetron hydrochloride, metroclopramide, domperidone, haloperidol, cyclizine, lorazepam, prochlorperazine, dexamethasone, levomepromazine, or tropisetron. The vaccine is preferably GM-CSF DNA and cell-based vaccines, dendritic cell vaccine, recombinant viral vaccines, heat shock protein (HSP) vaccines, allogeneic or autologous tumor vaccines. The analgesic agent preferably is ibuprofen, naproxen, choline magnesium trisalicylate, or oxycodone hydrochloride. The anti-vascular agent preferably is bevacizumab, or rhuMAb-VEGF. Further second medicaments include antiproliferative agents such a farnesyl protein transferase inhibitors, anti-VEGF inhibitors, p53 inhibitors, or PDGFR inhibitors. The second medicament herein includes also biologic-targeted therapy such as treatment with antibodies as well as small-molecule-targeted therapy, for example, against certain receptors.

Many anti-angiogenic agents have been identified and are known in the art, including those listed herein, e.g., listed under Definitions, and by, e.g., Carmeliet and Jain, Nature 407:249-257 (2000); Ferrara et al., Nature Reviews: Drug Discovery, 3:391-400 (2004); and Sato Int. J. Clin. Oncol., 8:200-206 (2003). See also, US Patent Application US20030055006. In one embodiment, an anti-FGF19 antibody is used in combination with an anti-VEGF neutralizing antibody (or fragment) and/or another VEGF antagonist or a VEGF receptor antagonist including, but not limited to, for example, soluble VEGF receptor (e.g., VEGFR-1, VEGFR-2, VEGFR-3, neuropillins (e.g., NRP1, NRP2)) fragments, aptamers capable of blocking VEGF or VEGFR, neutralizing anti-VEGFR antibodies, low molecule weight inhibitors of VEGFR tyrosine kinases (RTK), antisense strategies for VEGF, ribozymes against VEGF or VEGF receptors, antagonist variants of VEGF; and any combinations thereof. Alternatively, or additionally, two or more angiogenesis inhibitors may optionally be co-administered to the patient in addition to VEGF antagonist and other agent. In certain embodiment, one or more additional therapeutic agents, e.g., anti-cancer agents, can be administered in combination with anti-FGF19 antibody, the VEGF antagonist, and an anti-angiogenesis agent.

Chemotherapeutic agents useful herein are described supra, e.g., in the definition of "chemotherapeutic agent".

Exemplary second medicaments include an alkylating agent, a folate antagonist, a pyrimidine antagonist, a cytotoxic antibiotic, a platinum compound or platinum-based compound, a taxane, a vinca alkaloid, a c-Kit inhibitor, a topoisomerase inhibitor, an anti-angiogenesis inhibitor such as an anti-VEGF inhibitor, a HER-2 inhibitor, an EGFR inhibitor or dual EGFR/HER-2 kinase inhibitor, an anti-estrogen such as fulvestrant, and a hormonal therapy agent, such as carboplatin, cisplatin, gemcitabine, capecitabine, epirubicin, tamoxifen, an aromatase inhibitor, and prednisone. Most preferably, the cancer is colorectal cancer and the second medicament is an EGFR inhibitor such as erlotinib, an anti-VEGF inhibitor such as bevacizumab, or is cetuximab, arinotecan, irinotecan, or FOLFOX, or the cancer is breast cancer an the second medicament is an anti-estrogen modulator such as fulvestrant, tamoxifen or an aromatase inhibitor such as letrozole, exemestane, or anastrozole, or is a VEGF inhibitor such as bevacizumab, or is a chemotherapeutic agent such as doxorubicin, and/or a taxane such as paclitaxel, or is an anti-HER-2 inhibitor such as trastuzumab, or a dual EGFR/HER-2 kinase inhibitor such as lapatinib or a HER-2 downregulator such as 17AAG (geldanamycin derivative that is a heat shock protein [Hsp] 90 poison) (for example, for breast cancers that have progressed on trastuzumab). In other embodiments, the cancer is lung cancer, such as small-cell lung cancer, and the second medicament is a VEGF inhibitor such as bevacizumab, or an EGFR inhibitor such as, e.g., erlotinib or a c-Kit inhibitor such as e.g., imatinib. In other embodiments, the cancer is liver cancer, such as hepatocellular carcinoma, and the second medicament is an EGFR inhibitor such as erlotinib, a chemotherapeutic agent such as doxorubicin or irinotecan, a taxane such as paclitaxel, thalidomide and/or interferon. Further, a preferred chemotherapeutic agent for front-line therapy of cancer is taxotere, alone in combination with other second medicaments. Most preferably, if chemotherapy is administered, it is given first, followed by the antibodies herein.

Such second medicaments may be administered within 48 hours after the antibodies herein are administered, or within 24 hours, or within 12 hours, or within 3-12 hours after said agent, or may be administered over a pre-selected period of time, which is preferably about 1 to 2 days. Further, the dose of such agent may be sub-therapeutic.

The antibodies herein can be administered concurrently, sequentially, or alternating with the second medicament or upon non-responsiveness with other therapy. Thus, the combined administration of a second medicament includes co-administration (concurrent administration), using separate formulations or a single pharmaceutical formulation, and consecutive administration in either order, wherein preferably there is a time period while both (or all) medicaments simultaneously exert their biological activities. All these second medicaments may be used in combination with each other or by themselves with the first medicament, so that the express "second medicament" as used herein does not mean it is the only medicament besides the first medicament, respectively. Thus, the second medicament need not be one medicament, but may constitute or comprise more than one such drug.

These second medicaments as set forth herein are generally used in the same dosages and with administration routes as the first medicaments, or about from 1 to 99% of the dosages of the first medicaments. If such second medicaments are used at all, preferably, they are used in lower amounts than if the first medicament were not present, especially in subsequent dosings beyond the initial dosing with the first medicament, so as to eliminate or reduce side effects caused thereby.

The invention also provides methods and compositions for inhibiting or preventing relapse tumor growth or relapse cancer cell growth. Relapse tumor growth or relapse cancer cell growth is used to describe a condition in which patients undergoing or treated with one or more currently available therapies (e.g., cancer therapies, such as chemotherapy, radiation therapy, surgery, hormonal therapy and/or biological therapy/immunotherapy, anti-VEGF antibody therapy, particularly a standard therapeutic regimen for the particular cancer) is not clinically adequate to treat the patients or the patients are no longer receiving any beneficial effect from the therapy such that these patients need additional effective therapy. As used herein, the phrase can also refer to a condition of the "non-responsive/refractory" patient, e.g., which describe patients who respond to therapy yet suffer from side effects, develop resistance, do not respond to the therapy, do not respond satisfactorily to the therapy, etc. In various embodiments, a cancer is relapse tumor growth or relapse cancer cell growth where the number of cancer cells has not been significantly reduced, or has increased, or tumor size has not been significantly reduced, or has increased, or fails any further reduction in size or in number of cancer cells. The determination of whether the cancer cells are relapse tumor growth or relapse cancer cell growth can be made either in vivo or in vitro by any method known in the art for assaying the effectiveness of treatment on cancer cells, using the art-accepted meanings of "relapse" or "refractory" or "non-responsive" in such a context. A tumor resistant to anti-VEGF treatment is an example of a relapse tumor growth.

The invention provides methods of blocking or reducing relapse tumor growth or relapse cancer cell growth in a subject by administering one or more anti-FGF19 antibody to block or reduce the relapse tumor growth or relapse cancer cell growth in subject. In certain embodiments, the antagonist can be administered subsequent to the cancer therapeutic. In certain embodiments, the anti-FGF19 antibody is administered simultaneously with cancer therapy. Alternatively, or additionally, the anti-FGF19 antibody therapy alternates with another cancer therapy, which can be performed in any order. The invention also encompasses methods for administering one or more inhibitory antibodies to prevent the onset or recurrence of cancer in patients predisposed to having cancer. Generally, the subject was or is concurrently undergoing cancer therapy. In one embodiment, the cancer therapy is treatment with an anti-angiogenesis agent, e.g., a VEGF antagonist. The anti-angiogenesis agent includes those known in the art and those found under the Definitions herein. In one embodiment, the anti-angiogenesis agent is an anti-VEGF neutralizing antibody or fragment (e.g., humanized A4.6.1, AVASTIN® (Genentech, South San Francisco, Calif.), Y0317, M4, G6, B20, 2C3, etc.). See, e.g., U.S. Pat. Nos. 6,582,959, 6,884,879, 6,703,020; WO98/45332; WO 96/30046; WO94/10202; EP 0666868B1; US Patent Applications 20030206899, 20030190317, 20030203409, and 20050112126; Popkov et al., Journal of Immunological Methods 288:149-164 (2004); and, WO2005012359. Additional agents can be administered in combination with VEGF antagonist and an anti-FGF19 antibody for blocking or reducing relapse tumor growth or relapse cancer cell growth.

The antibodies of the invention (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibodies are suitably administered by pulse infusion, particularly with declining doses of the antibody. Dosing can be by any suitable route, e.g. by injections, such as intravenous or subcutaneous injections, depending in part on whether the administration is brief or chronic.

The location of the binding target of an antibody of the invention may be taken into consideration in preparation and administration of the antibody. When the binding target is an intracellular molecule, certain embodiments of the invention provide for the antibody or antigen-binding fragment thereof to be introduced into the cell where the binding target is located. In one embodiment, an antibody of the invention can be expressed intracellularly as an intrabody. The term "intrabody," as used herein, refers to an antibody or antigen-binding portion thereof that is expressed intracellularly and that is capable of selectively binding to a target molecule, as described, e.g., in Marasco, Gene Therapy 4: 11-15 (1997); Kontermann, Methods 34: 163-170 (2004); U.S. Pat. Nos. 6,004,940 and 6,329,173; U.S. Patent Application Publication No. 2003/0104402, and PCT Publication No. WO2003/077945. See also, for example, WO96/07321 published Mar. 14, 1996, concerning the use of gene therapy to generate intracellular antibodies.

Intracellular expression of an intrabody may be effected by introducing a nucleic acid encoding the desired antibody or antigen-binding portion thereof (lacking the wild-type leader sequence and secretory signals normally associated with the gene encoding that antibody or antigen-binding fragment) into a target cell. One or more nucleic acids encoding all or a portion of an antibody of the invention can be delivered to a target cell, such that one or more intrabodies are expressed which are capable of binding to an intracellular target polypeptide and modulating the activity of the target polypeptide. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of interest.

In certain embodiments, nucleic acid (optionally contained in a vector) may be introduced into a patient's cells by in vivo and ex vivo methods. In one example of in vivo delivery, nucleic acid is injected directly into the patient, e.g., at the site where therapeutic intervention is required. In a further example of in vivo delivery, nucleic acid is introduced into a cell using transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of certain gene marking and gene therapy protocols, see Anderson et al., Science 256:808-813 (1992), and WO 93/25673 and the references cited therein. In an example of ex vivo treatment, a patient's cells are removed, nucleic acid is introduced into those isolated cells, and the modified cells are administered to the patient either directly or, for example, encapsulated within porous membranes which are implanted into the patient (see, e.g., U.S. Pat. Nos. 4,892,538 and 5,283, 187). A commonly used vector for ex vivo delivery of a nucleic acid is a retroviral vector.

In another embodiment, internalizing antibodies are provided. Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the target protein may be advantageous. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889-7893 (1993).

Entry of antibodies into target cells can be enhanced by other methods known in the art. For example, certain sequences, such as those derived from HIV Tat or the Antennapedia homeodomain protein are able to direct efficient uptake of heterologous proteins across cell membranes. See, e.g., Chen et al., *Proc. Natl. Acad. Sci. USA* (1999), 96:4325-4329.

When the binding target of an antibody is located in the brain, certain embodiments of the invention provide for the antibody to traverse the blood-brain barrier. Several art-known approaches exist for transporting molecules across the blood-brain barrier, including, but not limited to, physical methods, lipid-based methods, stem cell-based methods, and receptor and channel-based methods.

Physical methods of transporting an antibody across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., *Gene Therapy* 9: 398-406 (2002)), interstitial infusion/convection-enhanced delivery (see, e.g., Bobo et al., *Proc. Natl. Acad. Sci. USA* 91: 2076-2080 (1994)), and implanting a delivery device in the brain (see, e.g., Gill et al., *Nature Med.* 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., *Implication of the Blood-Brain Barrier and its Manipulation*, Vols 1 & 2, Plenum Press, N.Y. (1989)), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody (see, e.g., U.S. Patent Publication No. 2003/0083299).

Lipid-based methods of transporting an antibody across the blood-brain barrier include, but are not limited to, encapsulating the antibody in liposomes that are coupled to antibody binding fragments that bind to receptors on the vascular endothelium of the blood-brain barrier (see, e.g., U.S. Patent Application Publication No. 20020025313), and coating the antibody in low-density lipoprotein particles (see, e.g., U.S. Patent Application Publication No. 20040204354) or apolipoprotein E (see, e.g., U.S. Patent Application Publication No. 20040131692).

Stem-cell based methods of transporting an antibody across the blood-brain barrier entail genetically engineering neural progenitor cells (NPCs) to express the antibody of interest and then implanting the stem cells into the brain of the individual to be treated. See Behrstock et al. (2005) *Gene Ther.* 15 Dec. 2005 advanced online publication (reporting that NPCs genetically engineered to express the neurotrophic factor GDNF reduced symptoms of Parkinson disease when implanted into the brains of rodent and primate models).

Receptor and channel-based methods of transporting an antibody across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Diagnostic Methods and Methods of Detection

The anti-FGF19 antibodies of the invention are useful in assays detecting FGF19 expression (such as diagnostic or prognostic assays) in specific cells or tissues wherein the antibodies are labeled as described below and/or are immobilized on an insoluble matrix. However, it is understood that any suitable anti-FGF19 antibody may be used in embodiments involving detection and diagnosis. Some methods for making anti-FGF19 antibodies are described herein and methods for making anti-FGF19 antibodies are well known in the art.

In another aspect, the invention provides methods for detection of FGF19, the methods comprising detecting FGF19-anti-FGF19 antibody complex in the sample. The term "detection" as used herein includes qualitative and/or quantitative detection (measuring levels) with or without reference to a control.

In another aspect, the invention provides methods for diagnosing a disorder associated with FGF19 expression and/or activity, the methods comprising detecting FGF19-anti-FGF19 antibody complex in a biological sample from an individual having or suspected of having the disorder. In some embodiments, the FGF19 expression is increased expression or abnormal (undesired) expression.

In another aspect, the invention provides any of the anti-FGF19 antibodies described herein, wherein the anti-FGF19 antibody comprises a detectable label.

In another aspect, the invention provides a complex of any of the anti-FGF19 antibodies described herein and FGF19. In some embodiments, the complex is in vivo or in vitro. In some embodiments, the complex comprises a cancer cell. In some embodiments, the anti-FGF19 antibody is detectably labeled.

Anti-FGF19 antibodies (e.g., any of the FGF19 antibodies described herein) can be used for the detection of FGF19 in any one of a number of well known detection assay methods.

In one aspect, the invention provides methods for detecting a disorder associated with FGF19 expression and/or activity, the methods comprising detecting FGF19 in a biological sample from an individual. In some embodiments, the FGF19 expression is increased expression or abnormal expression. In some embodiments, the disorder is a tumor, cancer, and/or a cell proliferative disorder, such as colorectal cancer, lung cancer, hepatocellular carcinoma, breast cancer and/or pancreatic cancer. In some embodiment, the biological sample is serum or of a tumor.

In another aspect, the invention provides methods for selecting treatment for an individual, the methods comprising: (a) detecting FGF19 expression in an individual's biological sample, if any; and (b) subsequence to step (a), selecting treatment for the individual, wherein the selection of treatment is based on the FGF19 expression detected in step (a). In some embodiments, increased FGF19 expression in the individual's biological sample relative to a reference value or control sample is detected. In some embodiments, decreased FGF19 expression in the individual's biological sample relative to a reference value or control sample is detected in the individual. In some embodiments, FGF19 expression is detected and treatment with an anti-FGF19 antibody is selected. Methods of treating a disorder with an anti-FGF19 antibody are described herein and some methods are exemplified herein.

In another aspect, the invention provides methods for treating an individual having or suspected of having a cancer, a tumor, and/or a cell proliferative disorder or a liver disorder (such as cirrhosis) by administering an effective amount of an anti-FGF19 antibody, further wherein FGF19 expression and/or FGFR4 is detected in cells and/or tissue from the human patient before, during or after administration of an anti-FGF19 antibody. In some embodiments, FGF19 overexpression is detected before, during and/or after administration of an anti-FGF19 antibody. In some embodiments, FGFR4 expression is detected before, during and/or after administration of an anti-FGF19 antibody. Expression may be detected before; during; after; before and during; before and after; during and after; or before, during and after administration of an anti-FGF19 antibody. Methods of treating a disorder with an anti-FGF19 antibody are described herein and some methods are exemplified herein.

For example, a biological sample may be assayed for FGF19 by obtaining the sample from a desired source, admixing the sample with anti-FGF19 antibody to allow the antibody to form antibody/FGF19 complex with any FGF19 present in the mixture, and detecting any antibody/FGF19 complex present in the mixture. The biological sample may be prepared for assay by methods known in the art which are suitable for the particular sample. The methods of admixing the sample with antibodies and the methods of detecting antibody/FGF19 complex are chosen according to the type of assay used. Such assays include immunohistochemistry, competitive and sandwich assays, and steric inhibition assays. For sample preparation, a tissue or cell sample from a mammal (typically a human patient) may be used. Examples of samples include, but are not limited to, cancer cells such as colon, breast, prostate, ovary, lung, stomach, pancreas, lymphoma, and leukemia cancer cells. FGF19 may also be measured in serum. The sample can be obtained by a variety of procedures known in the art including, but not limited to surgical excision, aspiration or biopsy. The tissue may be fresh or frozen. In one embodiment, the sample is fixed and embedded in paraffin or the like. The tissue sample may be fixed (i.e. preserved) by conventional methodology (See e.g., "Manual of Histological Staining Method of the Armed Forces Institute of Pathology," $3^{rd}$ edition (1960) Lee G. Luna, H T (ASCP) Editor, The Blakston Division McGraw-Hill Book Company, New York; *The Armed Forces Institute of Pathology Advanced Laboratory Methods in Histology and Pathology* (1994) Ulreka V. Mikel, Editor, Armed Forces Institute of Pathology, American Registry of Pathology, Washington, D.C.). One of ordinary skill in the art will appreciate that the choice of a fixative is determined by the purpose for which the sample is to be histologically stained or otherwise analyzed. One of ordinary skill in the art will also appreciate that the length of fixation depends upon the size of the tissue sample and the fixative used. By way of example, neutral buffered formalin, Bouin's or paraformaldehyde, may be used to fix a sample. Generally, the sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine. If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De7 (CMS, Houston, Tex.) may be used.

Analytical methods for FGF19 all use one or more of the following reagents: labeled FGF19 analogue, immobilized FGF19 analogue, labeled anti-FGF19 antibody, immobilized anti-FGF19 antibody and steric conjugates. The labeled reagents also are known as "tracers."

The label used is any detectable functionality that does not interfere with the binding of FGF19 and anti-FGF19 antibody. Numerous labels are known for use in immunoassay, examples including moieties that may be detected directly, such as fluorochrome, chemiluminescent, and radioactive labels, as well as moieties, such as enzymes, that must be reacted or derivatized to be detected.

The label used is any detectable functionality that does not interfere with the binding of FGF19 and anti-FGF19 antibody. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., Nature, 144: 945 (1962); David et al., Biochemistry, 13: 1014-1021 (1974); Pain et al., J. Immunol. Methods, 40: 219-230 (1981); and Nygren, J. Histochem. and Cytochem., 30: 407-412 (1982). Preferred labels herein are enzymes such as horseradish peroxidase and alkaline phosphatase. The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166.

Immobilization of reagents is required for certain assay methods. Immobilization entails separating the anti-FGF19 antibody from any FGF19 that remains free in solution. This conventionally is accomplished by either insolubilizing the anti-FGF19 antibody or FGF19 analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the anti-FGF19 antibody or FGF19 analogue afterward, e.g., by immunoprecipitation.

The expression of proteins in a sample may be examined using immunohistochemistry and staining protocols. Immunohistochemical staining of tissue sections has been shown to be a reliable method of assessing or detecting presence of proteins in a sample. Immunohistochemistry ("IHC") techniques utilize an antibody to probe and visualize cellular antigens in situ, generally by chromogenic or fluorescent methods. For sample preparation, a tissue or cell sample from a mammal (typically a human patient) may be used. The sample can be obtained by a variety of procedures known in the art including, but not limited to surgical excision, aspiration or biopsy. The tissue may be fresh or frozen. In one embodiment, the sample is fixed and embedded in paraffin or the like. The tissue sample may be fixed (i.e. preserved) by conventional methodology. One of ordinary skill in the art will appreciate that the choice of a fixative is determined by the purpose for which the sample is to be histologically stained or otherwise analyzed. One of ordinary skill in the art will also appreciate that the length of fixation depends upon the size of the tissue sample and the fixative used.

IHC may be performed in combination with additional techniques such as morphological staining and/or fluorescence in-situ hybridization. Two general methods of IHC are available; direct and indirect assays. According to the first assay, binding of antibody to the target antigen (e.g., FGF19) is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

Aside from the sample preparation procedures discussed above, further treatment of the tissue section prior to, during or following IHC may be desired, For example, epitope retrieval methods, such as heating the tissue sample in citrate buffer may be carried out (see, e.g., Leong et al. Appl. Immunohistochem. 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody which binds specifically to the primary antibody (e.g. the primary antibody is rabbit polyclonal antibody and secondary antibody is goat anti-rabbit antibody).

Specimens thus prepared may be mounted and coverslipped. Slide evaluation is then determined, e.g. using a microscope, and staining intensity criteria, routinely used in the art, may be employed.

Other assay methods, known as competitive or sandwich assays, are well established and widely used in the commercial diagnostics industry.

Competitive assays rely on the ability of a tracer FGF19 analogue to compete with the test sample FGF19 for a limited number of anti-FGF19 antibody antigen-binding sites. The anti-FGF19 antibody generally is insolubilized before or after the competition and then the tracer and FGF19 bound to the anti-FGF19 antibody are separated from the unbound tracer and FGF19. This separation is accomplished by decanting (where the binding partner was preinsolubilized) or by centrifuging (where the binding partner was precipitated after the competitive reaction). The amount of test sample FGF19 is inversely proportional to the amount of bound tracer as measured by the amount of marker substance. Dose-response curves with known amounts of FGF19 are prepared and compared with the test results to quantitatively determine the amount of FGF19 present in the test sample. These assays are called ELISA systems when enzymes are used as the detectable markers.

Another species of competitive assay, called a "homogeneous" assay, does not require a phase separation. Here, a conjugate of an enzyme with the FGF19 is prepared and used such that when anti-FGF19 antibody binds to the FGF19 the presence of the anti-FGF19 antibody modifies the enzyme activity. In this case, the FGF19 or its immunologically active fragments are conjugated with a bifunctional organic bridge to an enzyme such as peroxidase. Conjugates are selected for use with anti-FGF19 antibody so that binding of the anti-FGF19 antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small FGF19 fragment so that antibody to hapten is substantially unable to bind the conjugate at the same time as anti-FGF19 antibody. Under this assay procedure the FGF19 present in the test sample will bind anti-FGF19 antibody, thereby allowing anti-hapten to bind the conjugate, resulting in a change in the character of the conjugate hapten, e.g., a change in fluorescence when the hapten is a fluorophore.

Sandwich assays particularly are useful for the determination of FGF19 or anti-FGF19 antibodies. In sequential sandwich assays an immobilized anti-FGF19 antibody is used to adsorb test sample FGF19, the test sample is removed as by washing, the bound FGF19 is used to adsorb a second, labeled anti-FGF19 antibody and bound material is then separated from residual tracer. The amount of bound tracer is directly proportional to test sample FGF19. In "simultaneous" sandwich assays the test sample is not separated before adding the labeled anti-FGF19. A sequential sandwich assay using an anti-FGF19 monoclonal antibody as one antibody and a polyclonal anti-FGF19 antibody as the other is useful in testing samples for FGF19.

The foregoing are merely exemplary detection assays for FGF19. Other methods now or hereafter developed that use anti-FGF19 antibody for the determination of FGF19 are included within the scope hereof, including the bioassays described herein.

In one aspect, the invention provides methods to detect (e.g., presence or absence of or amount) a polynucleotide(s) (e.g., FGF19 polynucleotides) in a biological sample from an individual, such as a human subject. A variety of methods for detecting polynucleotides can be employed and include, for example, RT-PCR, taqman, amplification methods, polynucleotide microarray, and the like.

Methods for the detection of polynucleotides (such as mRNA) are well known and include, for example, hybridization assays using complementary DNA probes (such as in situ hybridization using labeled FGF19 riboprobes), Northern blot and related techniques, and various nucleic acid amplification assays (such as RT-PCR using complementary primers specific for FGF19, and other amplification type detection methods, such as, for example, branched DNA, SPIA, Ribo-SPIA, SISBA, TMA and the like).

Biological samples from mammals can be conveniently assayed for, e.g., FGF19 mRNAs using Northern, dot blot or PCR analysis. For example, RT-PCR assays such as quantitative PCR assays are well known in the art. In an illustrative embodiment of the invention, a method for detecting FGF19 mRNA in a biological sample comprises producing cDNA from the sample by reverse transcription using at least one primer; amplifying the cDNA so produced using an FGF19 polynucleotide as sense and antisense primers to amplify FGF19 cDNAs therein; and detecting the presence or absence of the amplified FGF19 cDNA. In addition, such methods can include one or more steps that allow one to determine the amount (levels) of FGF19 mRNA in a biological sample (e.g. by simultaneously examining the levels a comparative control mRNA sequence of a housekeeping gene such as an actin family member). Optionally, the sequence of the amplified FGF19 cDNA can be determined.

Probes and/or primers may be labeled with a detectable marker, such as, for example, a radioisotope, fluorescent compound, bioluminescent compound, a chemiluminescent compound, metal chelator or enzyme. Such probes and primers can be used to detect the presence of FGF 19 polynucleotides in a sample and as a means for detecting a cell expressing FGF19 proteins. As will be understood by the skilled artisan, a great many different primers and probes may be prepared (e.g., based on the sequences provided in herein) and used effectively to amplify, clone and/or determine the presence or absence of and/or amount of FGF19 mRNAs.

Optional methods of the invention include protocols comprising detection of polynucleotides, such as FGF19 polynucleotide, in a tissue or cell sample using microarray technologies. For example, using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment. (see, e.g., WO 01/75166 published Oct. 11, 2001; (See, for example, U.S. Pat. No. 5,700,637, U.S. Pat. No. 5,445,934, and U.S. Pat. No. 5,807,522, Lockart, Nature Biotechnology, 14:1675-1680 (1996); Cheung, V. G. et al., Nature Genetics 21(Suppl):15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps: 1. preparation of fluorescently labeled target from RNA isolated from the sample, 2. hybridization of the labeled target to the microarray, 3. washing, staining, and scanning of the array, 4. analysis of the scanned image and 5. generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ).

The Affymetrix GeneChip® system is a commercially available microarray system which comprises arrays fabricated by direct synthesis of oligonucleotides on a glass surface. Probe/Gene Arrays: Oligonucleotides, usually 25 mers, are directly synthesized onto a glass wafer by a combination of semiconductor-based photolithography and solid phase chemical synthesis technologies. Each array contains up to 400,000 different oligos and each oligo is present in millions of copies. Since oligonucleotide probes are synthesized in known locations on the array, the hybridization patterns and signal intensities can be interpreted in terms of gene identity and relative expression levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligo. The Microarray Suite software subtracts the hybridization intensities of the mismatch probes from those of the perfect match probes to determine the absolute or specific intensity value for each probe set. Probes are chosen based on current information from GenBank and other nucleotide repositories. The sequences are believed to recognize unique regions of the 3' end of the gene. A GeneChip Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

In some embodiments, FGF19 gene deletion, gene mutation, or gene amplification is detected. Gene deletion, gene mutation, or amplification may be measured by any one of a wide variety of protocols known in the art, for example, by conventional Southern blotting, Northern blotting to quantitate the transcription of mRNA (Thomas, Proc. Natl. Acad. Sci. USA, 77:5201-5205 (1980)), dot blotting (DNA analysis), or in situ hybridization (e.g., FISH), using an appropriately labeled probe, cytogenetic methods or comparative genomic hybridization (CGH) using an appropriately labeled probe. In addition, these methods may be employed to detect FGF19 ligand gene deletion, ligand mutation, or gene amplification. As used herein, "detecting FGF19 expression" encompasses detection of FGF19 gene deletion, gene mutation or gene amplification.

Additionally, one can examine the methylation status of the FGF 19 gene in a tissue or cell sample. Aberrant demethylation and/or hypermethylation of CpG islands in gene 5' regulatory regions frequently occurs in immortalized and transformed cells, and can result in altered expression of various genes. A variety of assays for examining methylation status of a gene are well known in the art. For example, one can utilize, in Southern hybridization approaches, methylation-sensitive restriction enzymes which cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al. eds., 1995; De Marzo et al., Am. J. Pathol. 155(6): 1985-1992 (1999); Brooks et al, Cancer Epidemiol. Biomarkers Prev., 1998, 7:531-536); and Lethe et al., Int. J. Cancer 76(6): 903-908 (1998). As used herein, "detecting FGF19 expression" encompasses detection of FGF19 gene methylation.

In one aspect, the invention provides detection of expression of FGFR4 polypeptide and/or polynucleotide (alone or in conjunction (simultaneously and/or sequentially)) with FGF19 expression) in a biological sample. Using methods known in the art, including those described herein, the polynucleotide and/or polypeptide expression of FGFR4 can be detected. By way of example, the IHC techniques described above may be employed to detect the presence of one of more such molecules in the sample. As used herein, "in conjunction" is meant to encompass any simultaneous and/or sequential detection. Thus, it is contemplated that in embodiments in which a biological sample is being examined not only for the presence of FGF19, but also for the presence of FGFR4, separate slides may be prepared from the same tissue or sample, and each slide tested with a reagent that binds to FGF19 and/or FGFR4, respectively. Alternatively, a single slide may be prepared from the tissue or cell sample, and antibodies directed to FGF19 and FGFR4 may be used in connection with a multi-color staining protocol to allow visualization and detection of the FGF19 and FGFR4.

In another aspect, the invention provides methods for diagnosing a disorder associated with FGFR4 expression and/or activity, the methods comprising detecting FGFR4 in a biological sample from an individual. In some embodiments, FGFR4 expression is increased expression or abnormal expression. In some embodiments, the disorder is a tumor, cancer, and/or a cell proliferative disorder, such as colorectal cancer, lung cancer, hepatocellular carcinoma, breast cancer and/or pancreatic cancer. In some embodiment, the biological sample is serum or of a tumor.

In another aspect, the invention provides methods for diagnosing a disorder associated with FGFR4 and FGF19 expression and/or activity, the methods comprising detecting FGFR4 and FGF19 in a biological sample from an individual. In some embodiments, the FGF19 expression is increased expression or abnormal expression. In some embodiments, FGFR4 expression is increased expression or abnormal expression. In some embodiments, the disorder is a tumor, cancer, and/or a cell proliferative disorder, such as colorectal cancer, lung cancer, hepatocellular carcinoma, breast cancer and/or pancreatic cancer. In some embodiment, the biological sample is serum or of a tumor. In some embodiments, expression of FGFR4 is detected in a first biological sample, and expression of FGF19 is detected in a second biological sample.

In another aspect, the invention provides methods for selecting treatment for an individual, the methods comprising: (a) detecting FGFR4 expression in an individual's biological sample, if any; and (b) subsequence to step (a), selecting treatment for the individual, wherein the selection of treatment is based on the FGFR4 expression detected in step (a). In some embodiments, increased FGFR4 expression in the individual's biological sample relative to a reference value or control sample is detected. In some embodiments, decreased FGFR4 expression in the individual's biological sample relative to a reference value or control sample is detected in the individual. In some embodiments, FGFR4 expression is detected and treatment with an anti-FGF19 antibody is selected.

In another aspect, the invention provides methods for selecting treatment for an individual, the methods comprising: (a) detecting FGF19 and FGFR4 expression in the biological sample, if any; and (b) subsequence to step (a), selecting treatment for the individual, wherein the selection of treatment is based on the FGF19 and FGFR4 expression detected in step (a). In some embodiments, increased FGF19 expression in the individual's biological sample relative to a reference value or control sample is detected. In some embodiments, decreased FGF19 expression in the individual's biological sample relative to a reference value or control sample is detected in the individual. In some embodiments, increased FGFR4 expression in the individual's biological sample relative to a reference value or control sample is detected. In some embodiments, decreased FGFR4 expression in the individual's biological sample relative to a reference value or control sample is detected in the individual. In some embodiments, FGFR4 and FGF19 expression are detected and treatment with an anti-FGF19 antibody is selected. In some embodiments, expression of FGFR4 is detected in a first biological sample, and expression of FGF19 is detected in a second biological sample.

In another aspect, the invention provides methods for treating an individual having or suspected of having a cancer, a tumor, and/or a cell proliferative disorder or a liver disorder (such as cirrhosis) by administering an effective amount of an anti-FGF19 antibody, further wherein FGF19 expression and/or FGFR4 is detected in cells and/or tissue from the human patient before, during or after administration of an anti-FGF19 antibody. In some embodiments, FGF19 overexpression is detected before, during and/or after administration of an anti-FGF19 antibody. In some embodiments, FGFR4 expression is detected before, during and/or after administration of an anti-FGF19 antibody. Expression may be detected before; during; after; before and during; before and after; during and after; or before, during and after administration of an anti-FGF19 antibody.

In some embodiments involving detection, expression of FGFR4 downstream molecular signaling is detected in addition to or as an alternative to detection of FGFR4 detection. In some embodiments, detection of FGFR4 downstream molecular signaling comprises one or more of detection of phosphorylation of MAPK, FRS2 or ERK2.

Some embodiments involving detection further comprise detection of Wnt pathway activation. In some embodiments, detection of Wnt pathway activation comprises one or more of tyrosine phosphorylation of β-catenin, expression of Wnt target genes, β-catenin mutation, and E-cadherin binding to β-catenin. Detection of Wnt pathway activation is known in the art, and some examples are described and exemplified herein.

In some embodiments, the treatment is for a cancer selected from the group consisting of colorectal cancer, lung cancer, ovarian cancer, pituitary cancer, pancreatic cancer, mammary fibroadenoma, prostate cancer, head and neck squamous cell carcinoma, soft tissue sarcoma, breast cancer, neuroblastomas, melanoma, breast carcinoma, gastric cancer, colorectal cancer (CRC), epithelial carcinomas, brain cancer, endometrial cancer, testis cancer, cholangiocarcinoma, gallbladder carcinoma, and hepatocellular carcinoma.

Biological samples are described herein, e.g., in the definition of Biological Sample. In some embodiment, the biological sample is serum or of a tumor.

In embodiments involving detection of FGF19 and/or FGFR4 expression, FGF19 and/or FGFR4 polynucleotide expression and/or FGF19 and/or FGFR4 polypeptide expression may be detected. In some embodiments involving detection of FGF19 and/or FGFR4 expression, FGF19 and/or FGFR4 mRNA expression is detected. In other embodiments, FGF19 and/or FGFR4 polypeptide expression is detected using an anti-FGF19 agent and/or an anti-FGFR4 agent. In some embodiments, FGF19 and/or FGFR4 polypeptide expression is detected using an antibody. Any suitable antibody may be used for detection and/or diagnosis, including monoclonal and/or polyclonal antibodies, a human antibody, a chimeric antibody, an affinity-matured antibody, a humanized antibody, and/or an antibody fragment. In some embodiments, an anti-FGF19 antibody described herein is use for detection. In some embodiments, FGF19 and/or FGFR4 polypeptide expression is detected using immunohistochemistry (IHC). In some embodiments, FGF19 expression is scored at 2 or higher using an IHC.

In some embodiments involving detection of FGF19 and/or FGFR4 expression, presence and/or absence and/or level of FGF19 and/or FGFR4 expression may be detected. FGF19 and/or FGFR4 expression may be increased. It is understood that absence of FGF19 and/or FGFR4 expression includes insignificant, or de minimus levels. In some embodiments, FGF19 expression in the test biological sample is higher than that observed for a control biological sample (or control or reference level of expression). In some embodiments, FGF19 expression is at least about 2-fold, 5-fold, 10-fold, 20-fold, 30-fold, 40-fold, 50-fold, 75-fold, 100-fold, 150-fold higher, or higher in the test biological sample than in the control biological sample. In some embodiments, FGF19 polypeptide expression is determined in an immunohistochemistry ("IHC") assay to score at least 2 or higher for staining intensity. In some embodiments, FGF19 polypeptide expression is determined in an IHC assay to score at least 1 or higher, or at least 3 or higher for staining intensity. In some embodiments, FGF19 expression in the test biological sample is lower than that observed for a control biological sample (or control expression level).

In some embodiments, FGF19 expression is detected in serum and FGFR4 expression is detected in a tumor sample. In some embodiments, FGF19 expression and FGFR4 expression are detected in a tumor sample. In some embodiments, FGF19 expression is detected in serum or a tumor sample, and FGFR4 downstream molecular signaling and/or FGFR4 expression is detected in a tumor sample. In some embodiments, FGF19 expression is detected in serum or a tumor sample, and Wnt pathway activation is detected in a tumor sample. In some embodiments, FGF19 expression is detected in serum or a tumor sample, and FGFR4 downstream molecular signaling and/or FGFR4 expression and/or Wnt pathway activation is detected in a tumor sample.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition(s) effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice, such as cancer. Moreover, the article of manufacture may comprise (a) a first container with a composition contained therein, wherein the composition comprises an antibody of the invention; and (b) a second container with a composition contained therein. The article of manufacture in this embodiment of the invention may further comprise a package insert indicating that the first and second antibody compositions can be used to treat a particular condition, e.g. cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

EXAMPLES

The following materials and methods were used in the Examples.

Residue numbers are according to Kabat (Kabat et al., Sequences of proteins of immunological interest, 5th Ed., Public Health Service, National Institutes of Health, Bethesda, Md. (1991)).

Direct Hypervariable Region Grafts onto the Acceptor Human Consensus Framework

The phagemid used for this work is a monovalent Fab-g3 display vector and consists of 2 open reading frames under control of a single phoA promoter. The first open reading frame consists of the stII signal sequence fused to the VL and CH1 domains of the acceptor light chain and the second consists of the stII signal sequence fused to the VH and CH1 domains of the acceptor heavy chain followed by the minor phage coat protein P3.

Figure 1:
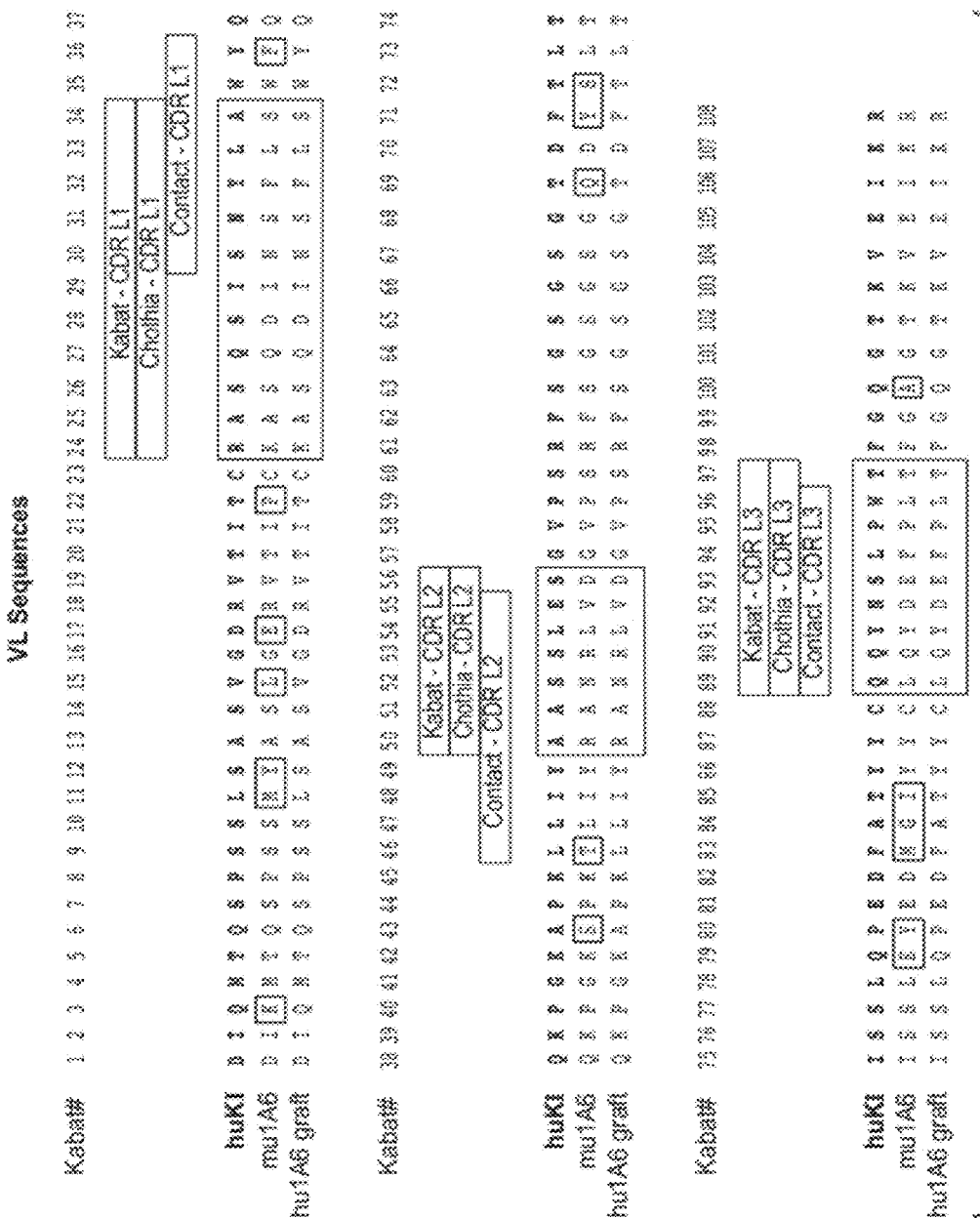
FIG. 1: depicts alignment of sequences of the variable light chain for the following: light chain human κI consensus sequence (SEQ ID NO:261), murine 1A6 antibody (SEQ ID NO:17) and, the 1A6 grafted antibody (SEQ ID NO:262). Positions are numbered according to Kabat.
Figure 2:
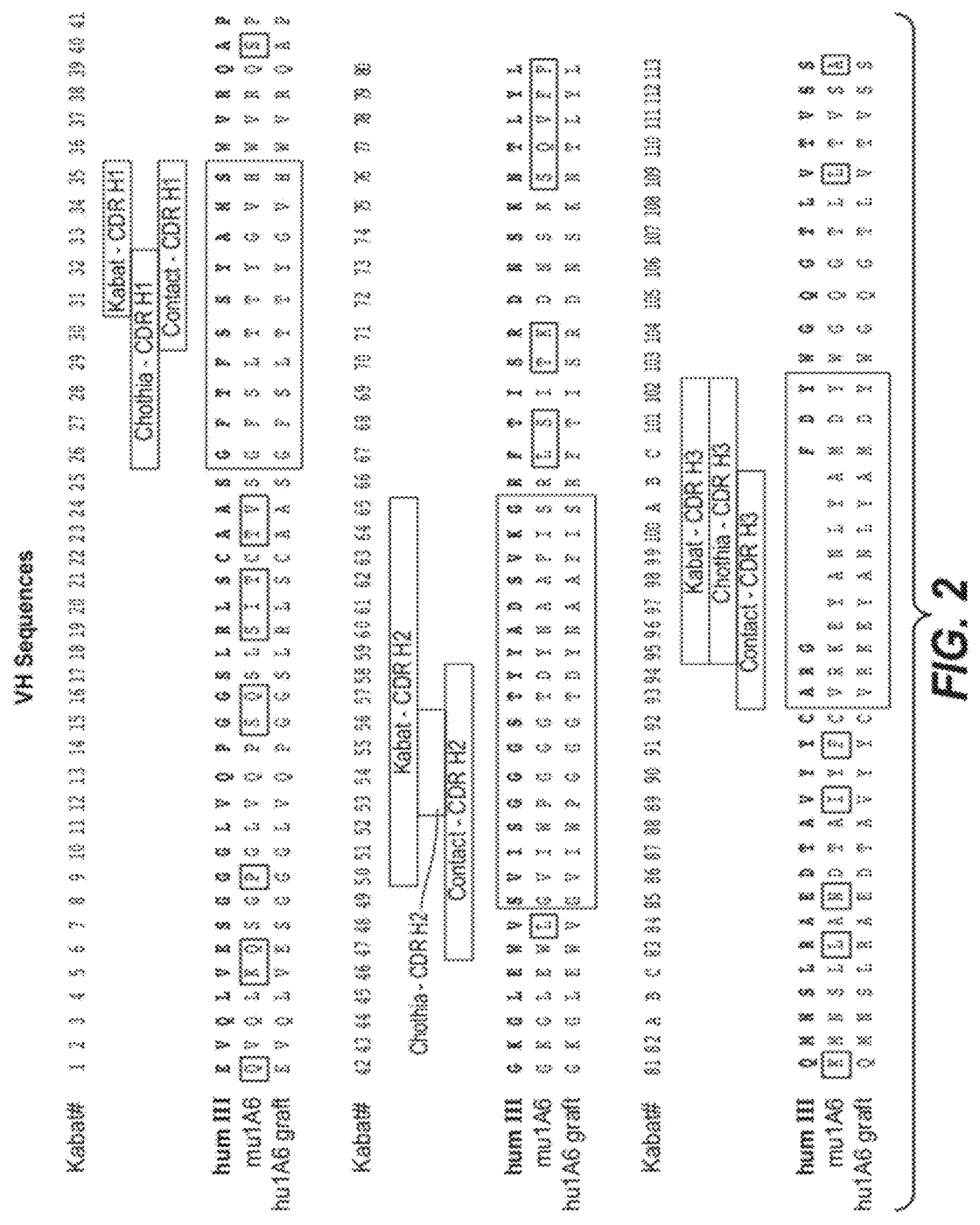

To make the HVR grafts, hypervariable regions from murine 1A6 antibody (mu1A6) (FIG. 8; see co-owned U.S. patent application Ser. No. 11/673,411, filed Feb. 9, 2007) were grafted into the huKI and huIII consensus acceptor frameworks to generate the direct HVR-graft of 1A6 (1A6-graft) (FIGS. 1 and 2). In the VL domain the following regions were grafted to the human consensus acceptor: positions 24-34 (L1), 50-56 (L2) and 89-97 (L3). In the VH domain, positions 26-35 (H1), 49-65 (H2) and 93-102 (H3) were grafted. MacCallum et al. (MacCallum et al. *J. Mol. Biol.* 262: 732-745 (1996)) have analyzed antibody and antigen complex crystal structures and found positions 49, 93 and 94 of the heavy chain are part of the contact region thus it seems reasonable to include these positions in the definition of HVR-H2 and HVR-H3 when humanizing antibodies. Correct clones were assessed by DNA sequencing.

Affinity Maturation

Human FGF19 was expressed in CHO cells and purified by conventional means.

For affinity maturation, phage libraries based upon the HVR graft were generated that had mutations introduced in to the HVR loops, e.g., as described in Dennis, WO2005080432.

High affinity clones were identified through five rounds of panning against human FGF19 protein with progressively increased stringency. Briefly, for the first 2 rounds of selection, FGF19 was immobilized directly on MaxiSorp microtiter plates (Nunc) at 2 µg/ml in PBS. Successive rounds of selection used biotinylated-FGF19 (b-FGF19) in a soluble selection method (see, e.g., Fuh et al. J. Mol. Biol. (2004)). FGF19 was biotinylated (b-FGF-19) using Sulfo-NHS-LC-biotin (Pierce). A short binding period and low concentrations of b-FGF19 were utilized to enable selection of clones possessing faster association rates.

Fab and IgG Production

To express Fab protein for affinity measurements, a stop codon was introduced between the heavy chain and g3 in the phage display vector. Clones were transformed into *E. coli* 34B8 cells and grown in Complete C.R.A.P. media at 30° C. (Presta et al. *Cancer Res.* 57: 4593-4599 (1997)). Cells were harvested by centrifugation, suspended in PBS, 100 uM PMSF, 100 uM benzamidine, 2.5 mM EDTA and broken open using a microfluidizer. Fab was purified with Protein G affinity chromatography.

For screening purposes, IgG variants were initially produced in 293 cells. Vectors coding for VL and VH (25 µg) were transfected into 293 cells using the FuGene system. 500 uL of FuGENE was mixed with 4.5 mL of DMEM media containing no FBS. This was incubated at room temperature for 5 minutes. The 25 µg of each chain is added to this mixture and incubated at room temperature for 20 minutes. 1 mL of mixture was pipetted into each flask for transfection overnight at 37 C in 5% CO2. The following day the media containing the transfection mixture was removed and replaced with 23 mL PS04 media with 0.1 mL/L of trace elements (A0934) and 10 mg/L of insulin (A0940). Cells were returned to the 37 C 5% CO2 incubator for an additional 5 days after which the media was harvested. The media was spun at 1000 rpm for 5 minutes and then sterile filtered using a 0.22 µm low protein binding filter. 2.5 mL of 0.1 M PMSF was added for every 125 mL of media as a protease inhibitor and then stored at 4 C.

Affinity Determinations

Affinity determinations were performed by surface plasmon resonance using a BIAcore™-2000. Two protocols were used. Purified 1A6 variant IgG was immobilized directly (approximately 550 RU) in 10 mM sodium acetate pH 4.8 on a CM5 sensor chip and serial 2-fold dilutions of the FGF19 (0.08-1250 nM) in PBST were injected at a flow rate of 30 µl/min. Each sample was analyzed with 4-minute association and 10-minute dissociation. After each injection the chip was regenerated using 10 mM Glycine pH 1.7. Binding response was corrected by subtracting the RU from a flow cell with an irrelevant IgG immobilized at similar density. A 1:1 Languir model of simultaneous fitting of $k_{on}$ and $k_{off}$ was used for kinetics analysis.

Unpurified 1A6 variant IgG was also assayed from culture supernatants using an anti-human IgG capture method on the BIAcore™ 2000. Approximately 2700 RU of rabbit anti-human IgG (Pierce #31143) was immobilized in 10 mM sodium acetate pH 4.0 on a CM5 sensor chip. The concentration of unpurified 1A6 variant IgG was normalized to capture approximately 200 RU of IgG from 5 µL of supernatant; an irrelevant IgG was captured on a control flow cell. FGF19 (a 2-fold serial dilution, 0.08 to 1000 nM in PBST) was injected at a flow rate of 30 μL/min. Each sample was analyzed with 4-minute association and 10-minute disassociation. After each injection the chip was regenerated using 10 mM Glycine pH 1.7. The immobilized anti-human IgG was then recharged with culture supernatant containing unpurified 1A6 variant IgG for the next dilution of FGF19. Binding response was corrected by subtracting the irrelevant IgG flow cell control from 1A6 variant IgG flow cells. A 1:1 Languir model of simultaneous fitting of $k_{on}$ and $k_{off}$ was used for kinetics analysis.

Solid Phase Receptor Binding Assay

Maxisorb 96 well plates were coated overnight at 4° C. with 50 μl of 2 μg/ml anti-human immunoglobulin Fcγ fragment specific (Jackson Immunoresearch) and used to capture 1 μg/ml FGFR-Fc chimeric proteins (R & D Systems). The non-specific binding sites were saturated with PBS/3% BSA for 1 hour and FGF19 (0.25 μg/ml) was incubated for 2 h in PBS/0.3% BSA in the presence of oligosaccharides (0.5 μg/ml; Neoparin Inc.) and the indicated anti-FGF19 antibody (0-10 μg/ml). FGF19 binding was detected using a biotinylated FGF19 specific polyclonal antibody (0.5 μg/ml; BAF969; R & D Systems) followed by streptavidin-HRP and TMB colorimetric substrate.

FGFR4/MAPK Phosphorylation

HEPG2 cells starved overnight in serum free media were treated with 250 ng/ml FGF19 for 10 min in the presence or the absence of antibodies. Cells were lysed in R27A buffer (Upstate) with 10 mM NaF, 1 mM sodium orthovanadate, and complete protease inhibitor tablet (Roche). Lysates were prepared, electrophoresed and analyzed by Immunoblot using anti-phospho-MAPK and anti-MAPK specific antibodies (Cell Signaling). For immunoprecipitation of FGFR4, equal amounts of proteins were incubated with 1 μg specific anti-FGFR4 (1G7; Genentech, Inc.) antibody immobilized onto protein A-Sepharose for 2 h at 4° C. then washed with lysis buffer and eluted with 2× Laemmli buffer, boiled, and microcentrifuged. Immunoblotting was performed with anti-phosphotyrosine antibody (4G10, UpState), anti-phospho-ERK2 antibody (Santa Cruz Biotech). Membranes were stripped (Pierce) and reprobed with appropriate antibodies to determine total proteins.

Western Blot for FGF19

Liver tissues were homogenized in modified RIPA buffer (50 mM Tris-Cl, pH 7.5; 150 mM NaCl; 1% IGEPAL; 1 mM EDTA; 0.25% sodium deoxycholate; 1 mM NaF; 1 mM Na3VO4; protease inhibitors cocktail (Sigma-Aldrich, St. Louis, Mo.) and clarified by centrifugation. Protein concentrations of the lysates were determined using the BCA protein assay reagent (Pierce, Rockford, Ill.). Equal amounts of proteins were incubated with specific antibody immobilized onto protein A-Sepharose (Sigma-Aldrich) for 2 hours at 4° C. with gentle rotation. Beads were washed extensively with lysis buffer and immunecomplexes were eluted in 2× Laemmli buffer, boiled and microcentrifuged. Proteins were resolved on SDS-PAGE, transferred to nitrocellulose membrane and incubated with specific primary antibodies. After washing and incubating with secondary antibodies, immunoreactive proteins were visualized by the ECL detection system (Amersham, Arlington Ht. IL). Recombinant human and cynomolgus proteins were loaded at a concentration of 100 ng or 200 ng.

Xenograft Experiment

Six- to eight-week-old athymic BALB/c female mice (Charles Rivers Inc.) were inoculated subcutaneously with $5 \times 10^6$ HCT116 colon tumor (200 μl/mouse). After 7 days, mice bearing tumors of equivalent volumes (~100 mm³) were randomized into groups (n=10) and treated intraperitoneally once weekly. Tumors were measured with an electronic caliper (Fowler Sylvac Ultra-Cal Mark III) and average tumor volume was calculated using the formula: (W2×L)/2 (W, the smaller diameter; L, the larger diameter).

FGFR4, FRS2, ERK and β-Catenin Phosphorylation in Xenograft Tumors

Tumors excised from treated animals were homogenized in lysis buffer [50 mM Tris-HCl, pH 7.5, 150 mM NaCl, 1% NP-40, 1 mM EDTA, 0.25% sodium deoxycholate, 1 mM NaF, 1 mM sodium orthovanadate and complete protease inhibitor (Roche)]. Equal amounts of proteins were incubated with 1 μg specific FGFR4 (1G7; Genentech, Inc.) or FRS2 (UpState) antibody immobilized onto protein A-Sepharose for 2 h at 4° C. then washed with lysis buffer and eluted with 2× Laemmli buffer, boiled, and microcentrifuged. Immunoblots were done with anti-phosphotyrosine antibody (4G10, UpState), anti-phospho-ERK2 antibody (Santa Cruz Biotech) or anti-N-terminally dephosphorylated β-catenin antibody (UpState). Membranes were stripped (Pierce) and reprobed with appropriate antibodies to determine total proteins.

Results and Discussion

Humanization of 1A6

The human acceptor framework used for humanization of 1A6 consists of the consensus human kappa I VL domain and the human subgroup III consensus VH domain. The VL and VH domains of mu1A6 were aligned with the human kappa I and subgroup III domains; each HVR was identified and grafted into the human acceptor framework to generate a 1A6 HVR graft that could be displayed as an Fab on phage (FIGS. 1 and 2).

Phage expressing the 1A6-graft bound to immobilized huFGF19; however, when 1A6-graft was expressed as an IgG, Biacore analysis of its affinity for FGF19 revealed that binding affinity had been reduced by over 50-fold relative to the chimeric 1A6 antibody, largely due to a reduction in the association rate ($K_{on}$) (Table 2).

TABLE 2

Biacore analysis of chimeric 1A6 and 1A6-graft

| | Binding to soluble Human FGF19 | | |
|---|---|---|---|
| | Ka (M/s) | Kd (s−1) | KD (pM) |
| chimeric 1A6 | 1.47E+06 | 5.30E−05 | 36 |
| 1A6-graft | 5.93E+04 | 1.24E−04 | 2091 |

Figure 3A:
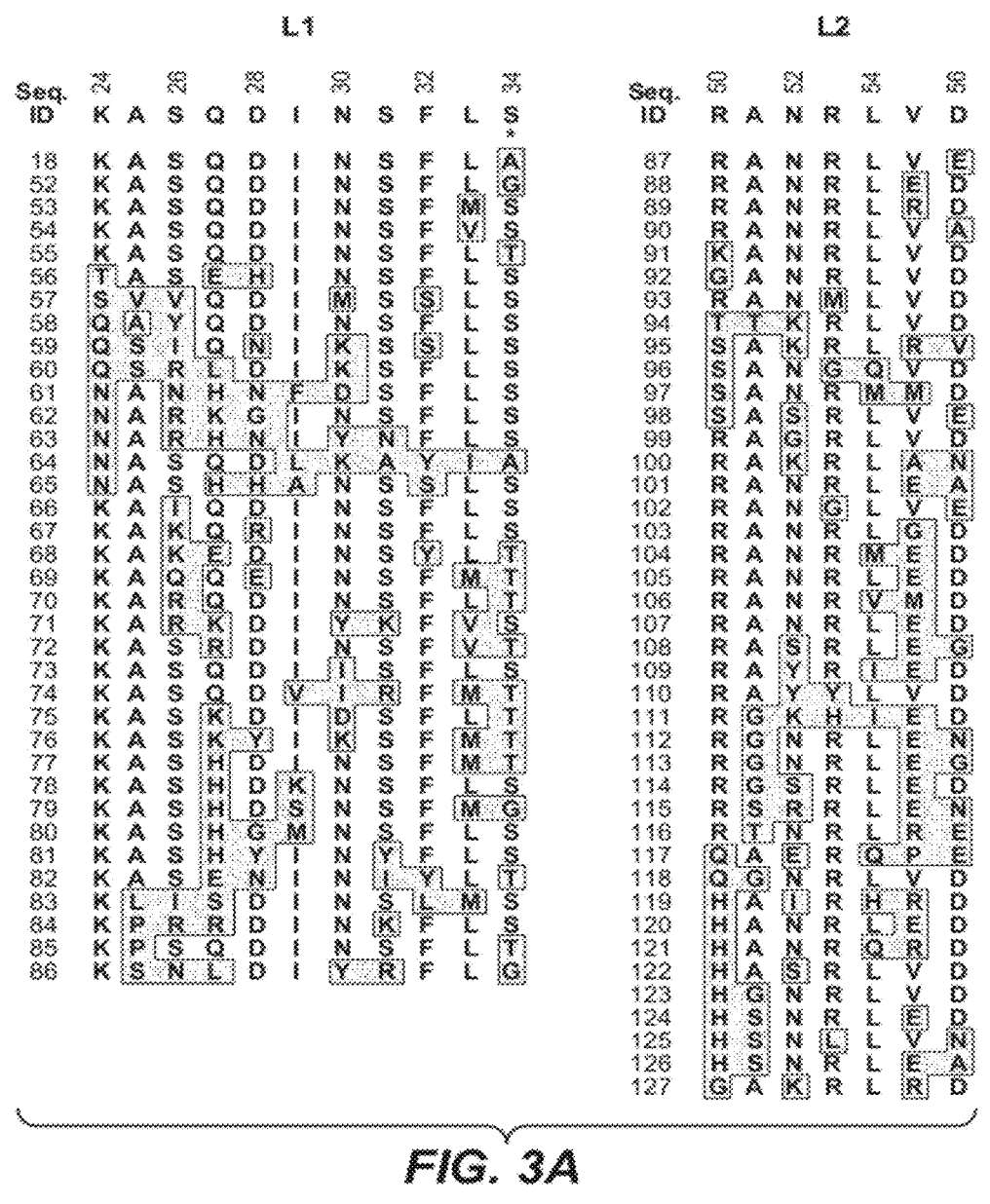
Figure 3B:
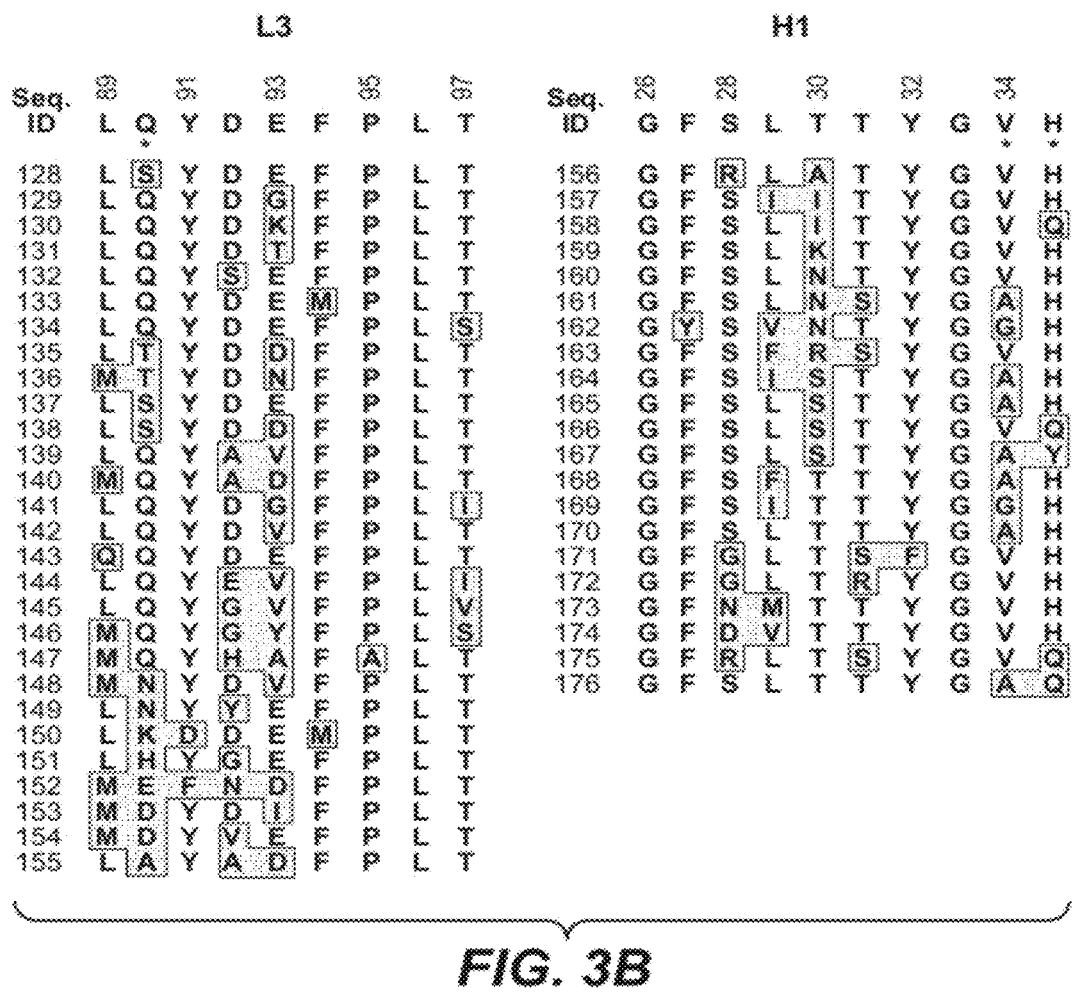
Figure 3C:
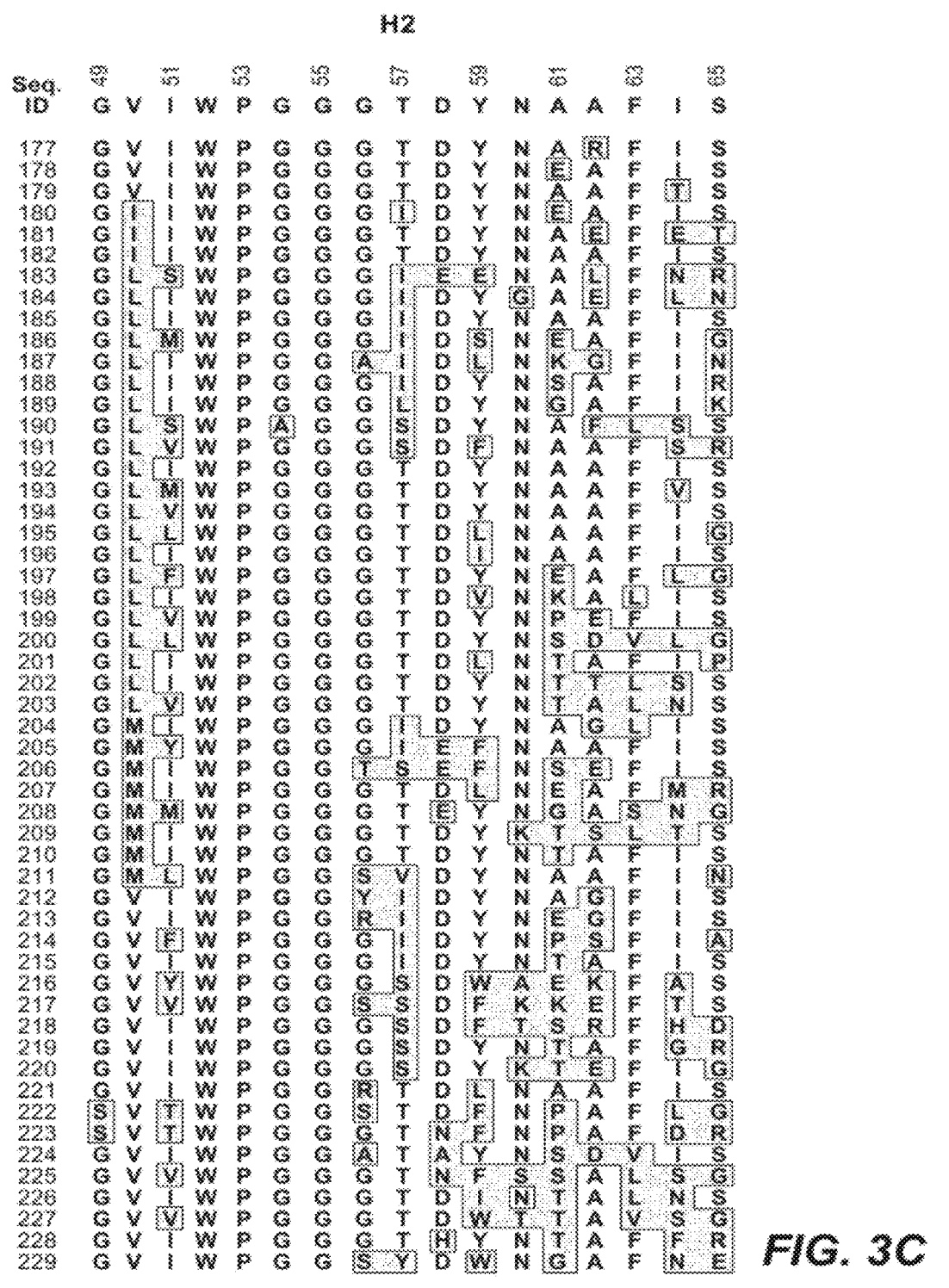

Phage libraries based upon the 1A6 HVR graft were generated that had mutations introduced in to the HVR loops. These libraries were panned for 2 rounds against immobilized FGF19 followed by 3 additional rounds of selection using short durations for binding to low concentrations of soluble b-FGF19. Enrichment, defined as the number of phage recovered in the presence of b-FGF divided by the number of phage recovered in the absence of b-FGF, was observed beginning after round 3. Following 5 rounds of selection, clones were picked for DNA sequence analysis. Sequence changes targeting each of the HVRs were observed (FIG. 3).

Selected clones were reformatted as IgG for further analysis by Biacore. Several clones had improved affinities compared to the 1A6-graft antibody (Table 3). These clones had changes in the light chain variable region (S34T, S34A or Q90S) or in the heavy chain variable region V34A, H35Q, V50L, A100bR or A100bP/M100cS).

TABLE 3

Biacore analysis of selected affinity matured antibodies

| | Binding to soluble Human FGF19 | | |
|---|---|---|---|
| | Ka (fold slower) | Kd (fold faster) | KD (fold weaker) |
| chimeric 1A6 | 1 | 1 | 1 |
| 1A6- graft | 24.8 | 2.3 | 58.1 |
| hu1A6.S34T (HVR-L1) | 12.0 | 1.2 | 14.0 |
| hu1A6.S34A (HVR-L1) | 7.7 | 1.2 | 9.1 |
| hu1A6.Q90S (HVR-L3) | 10.4 | 1.5 | 16.0 |
| hu1A6.V34A (HVR-H1) | 12.5 | 0.9 | 10.5 |
| hu1A6.H35Q (HVR-H1) | 5.0 | 1.3 | 6.6 |
| hu1A6.V50L (HVR-H2) | 6.3 | 0.9 | 5.7 |
| hu1A6.A100bR (HVR-H3) | 2.6 | 0.9 | 2.3 |
| hu1A6.A100bP/M100kS (HVR-H3) | 1.7 | 0.5 | 0.9 |

The best clones had 1 change from 1A6-graft (either S34A or S34G) and showed similar binding affinity to the murine 1A6 antibody for human FGF19.

Elimination of a Potential Iso-Aspartic Acid Forming Site in HVR-L2 of Humanized 1A6

To avoid potential manufacturing issues, a potential iso-aspartic acid forming site (Asp-Gly) in HVR-L2 of the humanized 1A6 variants was eliminated by converting D56 either to Glu (D56E) or Ser (D56S). Neither substitution had an effect on binding FGF19 as determined by Biacore. Tables 4 and 5 show the Biacore analysis of the D56S substituted antibodies.

TABLE 4

Biacore analysis of chimeric 1A6 antibody and affinity matured 1A6 variants to human FGF19

| | Binding to soluble Human FGF19 | | |
|---|---|---|---|
| | Ka (M/s) | Kd (s−1) | KD (pM) |
| chimeric 1A6 | 1.70E+06 | 5.40E−05 | 32 |
| hu1A6.S34A/D56S (HVR-L1/L2) | 3.90E+05 | 4.60E−05 | 118 |
| hu1A6.S34G/D56S (HVR-L1/L2) | 1.40E+05 | 1.60E−05 | 114 |

TABLE 5

Biacore analysis of chimeric 1A6 antibody and affinity matured 1A6 variants to cynomolgus FGF19

| | Binding to soluble Cyno FGF19 | | |
|---|---|---|---|
| | Ka (M/s) | Kd (s−1) | KD (pM) |
| chimeric 1A6 | 7.60E+05 | 6.60E−05 | 87 |
| hu1A6.S34A/D56S (HVR-L1/L2) | 1.60E+05 | 7.70E−05 | 481 |
| hu1A6.S34G/D56S (HVR-L1/L2) | 5.30E+04 | 4.80E−05 | 906 |

Thus, starting from a graft of the 6 murine 1A6 HVRs, the expansion of HVR-H2 to include position 49 (Glycine), the expansion of HCR-H3 to include positions 93 (Valine) and 94 (Arginine), the addition of 1 change in HVR-L1 leads to a fully humanized, high affinity 1A6 antibody with a binding affinity for human FGF19 that is similar to that of the parent murine 1A6 antibody. Other humanized 1A6 variants have also been identified that are potentially therapeutically suitable. Furthermore, selected humanized antibodies described herein have been determined to have at least comparable biological activity as the parent 1A6 antibody, for example in receptor phosphorylation assays, etc.

Characterization of an Antibody of the Invention

Humanized anti-FGF19 antibody 1A6.v1 was characterized as follows:

(1) In an assay to test ability of 1A6.v1 to block binding of FGF19 to its receptor, FGFR4, 1A6.v1 was able to block FGF19 binding to its receptor at least as well as one comparator antibody—namely a chimeric antibody (which comprised the variable regions from the murine parent 1A6 antibody (variable domains depicted in FIG. 8) fused to a human Fc region). When tested across an antibody concentration range of about 1-67 nM, under conditions as described in the Materials and Methods section above, 1A6.v1 was found to have an IC50 value that was similar to a comparator antibody such as the chimeric 1A6 antibody. See FIG. 9.

(2) 1A6.v1 was also tested for cross-species binding among human and primate (Cynomolgus macaque monkey). 1A6.v1 was found to bind specifically to human and primate (Cynomolgus monkey) FGF 19 receptor. In situ analysis revealed that cyno FGF19 expression in liver showed a similar pattern to human FGF19 expression in liver tissue. See FIG. 10.

(3) 1A6.v1 was tested for in vitro efficacy using a colon tumor cell line (HCT116 cells). Results from this study showed that the 1A6.v1 antibody was capable of inhibiting the phosphorylation of FGFR4, FRS2 and ERK in vitro. See FIG. 11.

(4) 1A6.v1 was tested for in vivo efficacy using a tumor xenograft model based on a colon tumor cell line (HCT116 cells). Results from this efficacy study showed that the 1A6.v1 antibody was capable of inhibiting growth of tumors in vivo. Moreover, the phosphorylation of FGFR4, FRS2, and ERK was inhibited in humanized anti-FGF19 antibody 1A6.v1-treated HCT116 xenograft tumors. See FIG. 12.

Although the foregoing invention has been described in some detail by way of illustration and example for purposes of clarity of understanding, the descriptions and examples should not be construed as limiting the scope of the invention.

What is claimed is:

1. An isolated anti-FGF19 antibody comprising:
   (a) a light chain comprising: (i) hypervariable region (HVR)-L1 comprising sequence A1-A11, wherein A1-A11 is KASQDINSFLA (SEQ ID NO:11); (ii) HVR-L2 comprising sequence B1-B7, wherein B1-B7 is RANRLVD (SEQ ID NO:2), RANRLVS (SEQ ID NO:13), or RANRLVE (SEQ ID NO:14); and (iii) HVR-L3 comprising sequence C1-C9, wherein C1-C9 is LQYDEFPLT (SEQ ID NO:3); and
   (b) a heavy chain comprising: (i) HVR-H1 comprising sequence D1-D10, wherein D1-D10 is GFSLTTYGVH (SEQ ID NO:4); (ii) HVR-H2 comprising sequence E1-E17, wherein E1-E17 is GVIWPGGGTDYNAAFIS (SEQ ID NO:7); and (iii) HVR-H3 comprising sequence F1-F13, wherein F1-F13 is VRKEYANLYAMDY (SEQ ID NO:8).

2. The antibody of claim 1, wherein the antibody is humanized.

3. The antibody of claim 1, wherein at least a portion of the framework sequence is a human consensus framework sequence.

4. The antibody of claim 1, wherein B1-B7 is RANRLVD (SEQ ID NO:2).

5. The antibody of claim 1, wherein B1-B7 is RANRLVS (SEQ ID NO:13).

6. The antibody of claim 1, wherein B1-B7 is RANRLVE (SEQ ID NO:14).

7. The antibody of claim 1 comprising human κ subgroup 1 consensus framework sequence.

8. The antibody of claim 1 comprising heavy chain human subgroup III consensus framework sequence.

9. Isolated nucleic acid encoding the antibody of claim 1.

10. A host cell comprising the nucleic acid of claim 9.

11. A pharmaceutical composition comprising the antibody of claim 1 and a pharmaceutically acceptable carrier.

12. A method for making an anti-FGF19 antibody, said method comprising culturing the host cell of claim 10 so that the antibody is produced.

13. The method of claim 12, further comprising recovering the antibody from the host cell.

14. The method of claim 12, wherein the host cell is eukaryotic.

* * * * *

SEQUENCE LISTING

<160> NUMBER OF SEQ ID NOS: 276

<210> SEQ ID NO 1
<211> LENGTH: 11
<212> TYPE: PRT
<213> ORGANISM: Homo sapiens

```
<400> SEQUENCE: 1

Lys Ala Ser Gln Asp Ile Asn Ser Phe Leu Ser
1               5                   10

<210> SEQ ID NO 2
<211> LENGTH: 7
<212> TYPE: PRT
<213> ORGANISM: Homo sapiens

<400> SEQUENCE: 2

Arg Ala Asn Arg Leu Val Asp
1               5

<210> SEQ ID NO 3
<211> LENGTH: 9
<212> TYPE: PRT
<213> ORGANISM: Homo sapiens

<400> SEQUENCE: 3

Leu Gln Tyr Asp Glu Phe Pro Leu Thr
1               5

<210> SEQ ID NO 4
<211> LENGTH: 10
<212> TYPE: PRT
<213> ORGANISM: Homo sapiens

<400> SEQUENCE: 4

Gly Phe Ser Leu Thr Thr Tyr Gly Val His
1               5                   10

<210> SEQ ID NO 5
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Any amino acid except Gly

<400> SEQUENCE: 5

Xaa Val Ile Trp Pro Gly Gly Gly Thr Asp Tyr Asn Ala Ala Phe Ile
1               5                   10                  15

Ser

<210> SEQ ID NO 6
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Any amino acid except Val
<220> FEATURE:
<221> NAME/KEY: MOD_RES
<222> LOCATION: (2)..(2)
<223> OTHER INFORMATION: Any amino acid except Arg

<400> SEQUENCE: 6

Xaa Xaa Lys Glu Tyr Ala Asn Leu Tyr Ala Met Asp Tyr
1               5                   10

<210> SEQ ID NO 7
<211> LENGTH: 17
<212> TYPE: PRT
<213> ORGANISM: Homo sapiens
```

```
<400> SEQUENCE: 7

Gly Val Ile Trp Pro Gly Gly Gly Thr Asp Tyr Asn Ala Ala Phe Ile
1               5                   10                  15

Ser

<210> SEQ ID NO 8
<211> LENGTH: 13
<212> TYPE: PRT
<213> ORGANISM: Homo sapiens

<400> SEQUENCE: 8

Val Arg Lys Glu Tyr Ala Asn Leu Tyr Ala Met Asp Tyr
1               5                   10

<210> SEQ ID NO 9
<211> LENGTH: 13
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Any amino acid except Arg

<400> SEQUENCE: 9

Val Xaa Lys Glu Tyr Ala Asn Leu Tyr Ala Met Asp Tyr
1               5                   10

<210> SEQ ID NO 10
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Any amino acid except Val

<400> SEQUENCE: 10

Xaa Arg Lys Glu Tyr Ala Asn Leu Tyr Ala Met Asp Tyr
1               5                   10

<210> SEQ ID NO 11
<211> LENGTH: 11
<212> TYPE: PRT
<213> ORGANISM: Homo sapiens

<400> SEQUENCE: 11

Lys Ala Ser Gln Asp Ile Asn Ser Phe Leu Ala
1               5                   10

<210> SEQ ID NO 12
<211> LENGTH: 11
<212> TYPE: PRT
<213> ORGANISM: Homo sapiens

<400> SEQUENCE: 12

Lys Ala Ser Gln Asp Ile Asn Ser Phe Leu Gly
1               5                   10

<210> SEQ ID NO 13
<211> LENGTH: 7
<212> TYPE: PRT
<213> ORGANISM: Homo sapiens

<400> SEQUENCE: 13

Arg Ala Asn Arg Leu Val Ser
1               5
```

```
<210> SEQ ID NO 14
<211> LENGTH: 7
<212> TYPE: PRT
<213> ORGANISM: Homo sapiens

<400> SEQUENCE: 14

Arg Ala Asn Arg Leu Val Glu
1               5

<210> SEQ ID NO 15
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 16
<211> LENGTH: 119
<212> TYPE: PRT
<213> ORGANISM: Mus sp.

<400> SEQUENCE: 16

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Thr Tyr
            20                  25                  30

Gly Val His Trp Val Arg Gln Ser Pro Gly Lys Gly Leu Glu Trp Leu
        35                  40                  45

Gly Val Ile Trp Pro Gly Gly Gly Thr Asp Tyr Asn Ala Ala Phe Ile
    50                  55                  60

Ser Arg Leu Ser Ile Thr Lys Asp Asn Ser Lys Ser Gln Val Phe Phe
65                  70                  75                  80

Lys Met Asn Ser Leu Leu Ala Asn Asp Thr Ala Ile Tyr Phe Cys Val
                85                  90                  95

Arg Lys Glu Tyr Ala Asn Leu Tyr Ala Met Asp Tyr Trp Gly Gln Gly
            100                 105                 110

Thr Leu Leu Thr Val Ser Ala
        115

<210> SEQ ID NO 17
<211> LENGTH: 108
<212> TYPE: PRT
```

<213> ORGANISM: Mus sp.

<400> SEQUENCE: 17

Asp Ile Lys Met Thr Gln Ser Pro Ser Ser Met Tyr Ala Ser Leu Gly
1               5                   10                  15

Glu Arg Val Thr Ile Pro Cys Lys Ala Ser Gln Asp Ile Asn Ser Phe
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Leu
                85                  90                  95

Thr Phe Gly Ala Gly Thr Lys Val Glu Ile Lys Arg
            100                 105

<210> SEQ ID NO 18
<211> LENGTH: 11
<212> TYPE: PRT
<213> ORGANISM: Homo sapiens

<400> SEQUENCE: 18

Lys Ala Ser Gln Asp Ile Asn Ser Phe Leu Ala
1               5                   10

<210> SEQ ID NO 19
<211> LENGTH: 30
<212> TYPE: PRT
<213> ORGANISM: Homo sapiens

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 20
<211> LENGTH: 14
<212> TYPE: PRT
<213> ORGANISM: Homo sapiens

<400> SEQUENCE: 20

Trp Val Arg Gln Ala Pro Gly Gln Gly Leu Glu Trp Met Gly
1               5                   10

<210> SEQ ID NO 21
<211> LENGTH: 32
<212> TYPE: PRT
<213> ORGANISM: Homo sapiens

<400> SEQUENCE: 21

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 22
<211> LENGTH: 25
<212> TYPE: PRT
<213> ORGANISM: Homo sapiens

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 23
<211> LENGTH: 13
<212> TYPE: PRT
<213> ORGANISM: Homo sapiens

<400> SEQUENCE: 23

Trp Val Arg Gln Ala Pro Gly Gln Gly Leu Glu Trp Met
1               5                   10

<210> SEQ ID NO 24
<211> LENGTH: 31
<212> TYPE: PRT
<213> ORGANISM: Homo sapiens

<400> SEQUENCE: 24

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala
            20                  25                  30

<210> SEQ ID NO 25
<211> LENGTH: 30
<212> TYPE: PRT
<213> ORGANISM: Homo sapiens

<400> SEQUENCE: 25

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 26
<211> LENGTH: 30
<212> TYPE: PRT
<213> ORGANISM: Homo sapiens

<400> SEQUENCE: 26

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser
            20                  25                  30

<210> SEQ ID NO 27
<211> LENGTH: 14
<212> TYPE: PRT
<213> ORGANISM: Homo sapiens

<400> SEQUENCE: 27

Trp Ile Arg Gln Pro Pro Gly Lys Gly Leu Glu Trp Ile Gly
1               5                   10

<210> SEQ ID NO 28
<211> LENGTH: 32
<212> TYPE: PRT
<213> ORGANISM: Homo sapiens

<400> SEQUENCE: 28

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 29
<211> LENGTH: 25
<212> TYPE: PRT
<213> ORGANISM: Homo sapiens

<400> SEQUENCE: 29

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 30
<211> LENGTH: 13
<212> TYPE: PRT
<213> ORGANISM: Homo sapiens

<400> SEQUENCE: 30

Trp Ile Arg Gln Pro Pro Gly Lys Gly Leu Glu Trp Ile
1               5                   10

<210> SEQ ID NO 31
<211> LENGTH: 31
<212> TYPE: PRT
<213> ORGANISM: Homo sapiens

<400> SEQUENCE: 31

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala
            20                  25                  30

<210> SEQ ID NO 32
<211> LENGTH: 30
<212> TYPE: PRT
<213> ORGANISM: Homo sapiens

<400> SEQUENCE: 32

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 33
<211> LENGTH: 30
<212> TYPE: PRT
<213> ORGANISM: Homo sapiens

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 34
<211> LENGTH: 14
<212> TYPE: PRT
<213> ORGANISM: Homo sapiens

```
<400> SEQUENCE: 34

Trp Val Arg Gln Ala Pro Gly Lys Gly Leu Glu Trp Val Ser
1               5                   10

<210> SEQ ID NO 35
<211> LENGTH: 32
<212> TYPE: PRT
<213> ORGANISM: Homo sapiens

<400> SEQUENCE: 35

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 36
<211> LENGTH: 31
<212> TYPE: PRT
<213> ORGANISM: Homo sapiens

<400> SEQUENCE: 36

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala
            20                  25                  30

<210> SEQ ID NO 37
<211> LENGTH: 30
<212> TYPE: PRT
<213> ORGANISM: Homo sapiens

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys
            20                  25                  30

<210> SEQ ID NO 38
<211> LENGTH: 23
<212> TYPE: PRT
<213> ORGANISM: Homo sapiens

<400> SEQUENCE: 38

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 39
<211> LENGTH: 15
<212> TYPE: PRT
<213> ORGANISM: Homo sapiens

<400> SEQUENCE: 39

Trp Tyr Leu Gln Lys Pro Gly Gln Ser Pro Gln Leu Leu Ile Tyr
1               5                   10                  15

<210> SEQ ID NO 40
<211> LENGTH: 32
<212> TYPE: PRT
<213> ORGANISM: Homo sapiens

<400> SEQUENCE: 40
```

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 41
<211> LENGTH: 23
<212> TYPE: PRT
<213> ORGANISM: Homo sapiens

<400> SEQUENCE: 41

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 42
<211> LENGTH: 23
<212> TYPE: PRT
<213> ORGANISM: Homo sapiens

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 43
<211> LENGTH: 15
<212> TYPE: PRT
<213> ORGANISM: Homo sapiens

<400> SEQUENCE: 43

Trp Tyr Gln Gln Lys Pro Gly Lys Ala Pro Lys Leu Leu Ile Tyr
1               5                   10                  15

<210> SEQ ID NO 44
<211> LENGTH: 32
<212> TYPE: PRT
<213> ORGANISM: Homo sapiens

<400> SEQUENCE: 44

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 45
<211> LENGTH: 10
<212> TYPE: PRT
<213> ORGANISM: Homo sapiens

<400> SEQUENCE: 45

Phe Gly Gln Gly Thr Lys Val Glu Ile Lys
1               5                   10

<210> SEQ ID NO 46
<211> LENGTH: 25
<212> TYPE: PRT
<213> ORGANISM: Homo sapiens

<400> SEQUENCE: 46

Glu Val Gln Leu Val Glu Ser Gly Gly Gly Leu Val Gln Pro Gly Gly
1               5                   10                  15

```
Ser Leu Arg Leu Ser Cys Ala Ala Ser
            20              25
```

<210> SEQ ID NO 47
<211> LENGTH: 13
<212> TYPE: PRT
<213> ORGANISM: Homo sapiens

<400> SEQUENCE: 47

```
Trp Val Arg Gln Ala Pro Gly Lys Gly Leu Glu Trp Val
1               5                   10
```

<210> SEQ ID NO 48
<211> LENGTH: 30
<212> TYPE: PRT
<213> ORGANISM: Homo sapiens

<400> SEQUENCE: 48

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30
```

<210> SEQ ID NO 49
<211> LENGTH: 11
<212> TYPE: PRT
<213> ORGANISM: Homo sapiens

<400> SEQUENCE: 49

```
Trp Gly Gln Gly Thr Leu Val Thr Val Ser Ser
1               5                   10
```

<210> SEQ ID NO 50
<211> LENGTH: 30
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Ala or Arg
<220> FEATURE:
<221> NAME/KEY: MOD_RES
<222> LOCATION: (8)..(8)
<223> OTHER INFORMATION: Thr or Asn
<220> FEATURE:
<221> NAME/KEY: MOD_RES
<222> LOCATION: (13)..(13)
<223> OTHER INFORMATION: Ala or Leu

<400> SEQUENCE: 50

```
Arg Phe Thr Ile Ser Xaa Asp Xaa Ser Lys Asn Thr Xaa Tyr Leu Gln
1               5                   10                  15

Met Asn Ser Leu Arg Ala Glu Asp Thr Ala Val Tyr Tyr Cys
            20                  25                  30
```

<210> SEQ ID NO 51
<211> LENGTH: 107
<212> TYPE: PRT
<213> ORGANISM: Homo sapiens

<400> SEQUENCE: 51

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30
```

```
Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 52
<211> LENGTH: 11
<212> TYPE: PRT
<213> ORGANISM: Homo sapiens

<400> SEQUENCE: 52

```
Lys Ala Ser Gln Asp Ile Asn Ser Phe Leu Gly
1               5                   10
```

<210> SEQ ID NO 53
<211> LENGTH: 11
<212> TYPE: PRT
<213> ORGANISM: Homo sapiens

<400> SEQUENCE: 53

```
Lys Ala Ser Gln Asp Ile Asn Ser Phe Met Ser
1               5                   10
```

<210> SEQ ID NO 54
<211> LENGTH: 11
<212> TYPE: PRT
<213> ORGANISM: Homo sapiens

<400> SEQUENCE: 54

```
Lys Ala Ser Gln Asp Ile Asn Ser Phe Val Ser
1               5                   10
```

<210> SEQ ID NO 55
<211> LENGTH: 11
<212> TYPE: PRT
<213> ORGANISM: Homo sapiens

<400> SEQUENCE: 55

```
Lys Ala Ser Gln Asp Ile Asn Ser Phe Leu Thr
1               5                   10
```

<210> SEQ ID NO 56
<211> LENGTH: 11
<212> TYPE: PRT
<213> ORGANISM: Homo sapiens

<400> SEQUENCE: 56

```
Thr Ala Ser Glu His Ile Asn Ser Phe Leu Ser
1               5                   10
```

<210> SEQ ID NO 57
<211> LENGTH: 11
<212> TYPE: PRT
<213> ORGANISM: Homo sapiens

<400> SEQUENCE: 57

```
Ser Val Val Gln Asp Ile Met Ser Ser Leu Ser
1               5                   10
```

<210> SEQ ID NO 58
<211> LENGTH: 11
<212> TYPE: PRT
<213> ORGANISM: Homo sapiens

<400> SEQUENCE: 58

Gln Ala Tyr Gln Asp Ile Asn Ser Phe Leu Ser
1               5                   10

<210> SEQ ID NO 59
<211> LENGTH: 11
<212> TYPE: PRT
<213> ORGANISM: Homo sapiens

<400> SEQUENCE: 59

Gln Ser Ile Gln Asn Ile Lys Ser Ser Leu Ser
1               5                   10

<210> SEQ ID NO 60
<211> LENGTH: 11
<212> TYPE: PRT
<213> ORGANISM: Homo sapiens

<400> SEQUENCE: 60

Gln Ser Arg Leu Asp Ile Lys Ser Phe Leu Ser
1               5                   10

<210> SEQ ID NO 61
<211> LENGTH: 11
<212> TYPE: PRT
<213> ORGANISM: Homo sapiens

<400> SEQUENCE: 61

Asn Ala Asn His Asn Phe Asp Ser Phe Leu Ser
1               5                   10

<210> SEQ ID NO 62
<211> LENGTH: 11
<212> TYPE: PRT
<213> ORGANISM: Homo sapiens

<400> SEQUENCE: 62

Asn Ala Arg Lys Gly Ile Asn Ser Phe Leu Ser
1               5                   10

<210> SEQ ID NO 63
<211> LENGTH: 11
<212> TYPE: PRT
<213> ORGANISM: Homo sapiens

<400> SEQUENCE: 63

Asn Ala Arg His Asn Ile Tyr Asn Phe Leu Ser
1               5                   10

<210> SEQ ID NO 64
<211> LENGTH: 11
<212> TYPE: PRT
<213> ORGANISM: Homo sapiens

<400> SEQUENCE: 64

Asn Ala Ser Gln Asp Leu Lys Ala Tyr Ile Ala
1               5                   10

<210> SEQ ID NO 65

```
<211> LENGTH: 11
<212> TYPE: PRT
<213> ORGANISM: Homo sapiens

<400> SEQUENCE: 65

Asn Ala Ser His His Ala Asn Ser Ser Leu Ser
1               5                   10

<210> SEQ ID NO 66
<211> LENGTH: 11
<212> TYPE: PRT
<213> ORGANISM: Homo sapiens

<400> SEQUENCE: 66

Lys Ala Ile Gln Asp Ile Asn Ser Phe Leu Ser
1               5                   10

<210> SEQ ID NO 67
<211> LENGTH: 11
<212> TYPE: PRT
<213> ORGANISM: Homo sapiens

<400> SEQUENCE: 67

Lys Ala Lys Gln Arg Ile Asn Ser Phe Leu Ser
1               5                   10

<210> SEQ ID NO 68
<211> LENGTH: 11
<212> TYPE: PRT
<213> ORGANISM: Homo sapiens

<400> SEQUENCE: 68

Lys Ala Lys Glu Asp Ile Asn Ser Tyr Leu Thr
1               5                   10

<210> SEQ ID NO 69
<211> LENGTH: 11
<212> TYPE: PRT
<213> ORGANISM: Homo sapiens

<400> SEQUENCE: 69

Lys Ala Gln Gln Glu Ile Asn Ser Phe Met Thr
1               5                   10

<210> SEQ ID NO 70
<211> LENGTH: 11
<212> TYPE: PRT
<213> ORGANISM: Homo sapiens

<400> SEQUENCE: 70

Lys Ala Arg Gln Asp Ile Asn Ser Phe Leu Thr
1               5                   10

<210> SEQ ID NO 71
<211> LENGTH: 11
<212> TYPE: PRT
<213> ORGANISM: Homo sapiens

<400> SEQUENCE: 71

Lys Ala Arg Lys Asp Ile Tyr Lys Phe Val Ser
1               5                   10

<210> SEQ ID NO 72
<211> LENGTH: 11
<212> TYPE: PRT
<213> ORGANISM: Homo sapiens
```

```
<400> SEQUENCE: 72

Lys Ala Ser Arg Asp Ile Asn Ser Phe Val Thr
1               5                   10

<210> SEQ ID NO 73
<211> LENGTH: 11
<212> TYPE: PRT
<213> ORGANISM: Homo sapiens

<400> SEQUENCE: 73

Lys Ala Ser Gln Asp Ile Ile Ser Phe Leu Ser
1               5                   10

<210> SEQ ID NO 74
<211> LENGTH: 11
<212> TYPE: PRT
<213> ORGANISM: Homo sapiens

<400> SEQUENCE: 74

Lys Ala Ser Gln Asp Val Ile Arg Phe Met Thr
1               5                   10

<210> SEQ ID NO 75
<211> LENGTH: 11
<212> TYPE: PRT
<213> ORGANISM: Homo sapiens

<400> SEQUENCE: 75

Lys Ala Ser Lys Asp Ile Asp Ser Phe Leu Thr
1               5                   10

<210> SEQ ID NO 76
<211> LENGTH: 11
<212> TYPE: PRT
<213> ORGANISM: Homo sapiens

<400> SEQUENCE: 76

Lys Ala Ser Lys Tyr Ile Asp Ser Phe Met Thr
1               5                   10

<210> SEQ ID NO 77
<211> LENGTH: 11
<212> TYPE: PRT
<213> ORGANISM: Homo sapiens

<400> SEQUENCE: 77

Lys Ala Ser His Asp Ile Asn Ser Phe Met Thr
1               5                   10

<210> SEQ ID NO 78
<211> LENGTH: 11
<212> TYPE: PRT
<213> ORGANISM: Homo sapiens

<400> SEQUENCE: 78

Lys Ala Ser His Asp Lys Asn Ser Phe Leu Ser
1               5                   10

<210> SEQ ID NO 79
<211> LENGTH: 11
<212> TYPE: PRT
<213> ORGANISM: Homo sapiens

<400> SEQUENCE: 79
```

```
Lys Ala Ser His Asp Ser Asn Ser Phe Met Gly
1               5                   10
```

<210> SEQ ID NO 80
<211> LENGTH: 11
<212> TYPE: PRT
<213> ORGANISM: Homo sapiens

<400> SEQUENCE: 80

```
Lys Ala Ser His Gly Met Asn Ser Phe Leu Ser
1               5                   10
```

<210> SEQ ID NO 81
<211> LENGTH: 11
<212> TYPE: PRT
<213> ORGANISM: Homo sapiens

<400> SEQUENCE: 81

```
Lys Ala Ser His Tyr Ile Asn Tyr Phe Leu Ser
1               5                   10
```

<210> SEQ ID NO 82
<211> LENGTH: 11
<212> TYPE: PRT
<213> ORGANISM: Homo sapiens

<400> SEQUENCE: 82

```
Lys Ala Ser Glu Asn Ile Asn Ile Tyr Leu Thr
1               5                   10
```

<210> SEQ ID NO 83
<211> LENGTH: 11
<212> TYPE: PRT
<213> ORGANISM: Homo sapiens

<400> SEQUENCE: 83

```
Lys Leu Ile Ser Asp Ile Asn Ser Leu Met Ser
1               5                   10
```

<210> SEQ ID NO 84
<211> LENGTH: 11
<212> TYPE: PRT
<213> ORGANISM: Homo sapiens

<400> SEQUENCE: 84

```
Lys Pro Arg Arg Asp Ile Asn Lys Phe Leu Ser
1               5                   10
```

<210> SEQ ID NO 85
<211> LENGTH: 11
<212> TYPE: PRT
<213> ORGANISM: Homo sapiens

<400> SEQUENCE: 85

```
Lys Pro Ser Gln Asp Ile Asn Ser Phe Leu Thr
1               5                   10
```

<210> SEQ ID NO 86
<211> LENGTH: 11
<212> TYPE: PRT
<213> ORGANISM: Homo sapiens

<400> SEQUENCE: 86

```
Lys Ser Asn Leu Asp Ile Tyr Arg Phe Leu Gly
1               5                   10
```

```
<210> SEQ ID NO 87
<211> LENGTH: 7
<212> TYPE: PRT
<213> ORGANISM: Homo sapiens

<400> SEQUENCE: 87

Arg Ala Asn Arg Leu Val Glu
1               5

<210> SEQ ID NO 88
<211> LENGTH: 7
<212> TYPE: PRT
<213> ORGANISM: Homo sapiens

<400> SEQUENCE: 88

Arg Ala Asn Arg Leu Glu Asp
1               5

<210> SEQ ID NO 89
<211> LENGTH: 7
<212> TYPE: PRT
<213> ORGANISM: Homo sapiens

<400> SEQUENCE: 89

Arg Ala Asn Arg Leu Arg Asp
1               5

<210> SEQ ID NO 90
<211> LENGTH: 7
<212> TYPE: PRT
<213> ORGANISM: Homo sapiens

<400> SEQUENCE: 90

Arg Ala Asn Arg Leu Val Ala
1               5

<210> SEQ ID NO 91
<211> LENGTH: 7
<212> TYPE: PRT
<213> ORGANISM: Homo sapiens

<400> SEQUENCE: 91

Lys Ala Asn Arg Leu Val Asp
1               5

<210> SEQ ID NO 92
<211> LENGTH: 7
<212> TYPE: PRT
<213> ORGANISM: Homo sapiens

<400> SEQUENCE: 92

Gly Ala Asn Arg Leu Val Asp
1               5

<210> SEQ ID NO 93
<211> LENGTH: 7
<212> TYPE: PRT
<213> ORGANISM: Homo sapiens

<400> SEQUENCE: 93

Arg Ala Asn Met Leu Val Asp
1               5

<210> SEQ ID NO 94
<211> LENGTH: 7
```

```
<212> TYPE: PRT
<213> ORGANISM: Homo sapiens

<400> SEQUENCE: 94

Thr Thr Lys Arg Leu Val Asp
1               5

<210> SEQ ID NO 95
<211> LENGTH: 7
<212> TYPE: PRT
<213> ORGANISM: Homo sapiens

<400> SEQUENCE: 95

Ser Ala Lys Arg Leu Arg Val
1               5

<210> SEQ ID NO 96
<211> LENGTH: 7
<212> TYPE: PRT
<213> ORGANISM: Homo sapiens

<400> SEQUENCE: 96

Ser Ala Asn Gly Gln Val Asp
1               5

<210> SEQ ID NO 97
<211> LENGTH: 7
<212> TYPE: PRT
<213> ORGANISM: Homo sapiens

<400> SEQUENCE: 97

Ser Ala Asn Arg Met Met Asp
1               5

<210> SEQ ID NO 98
<211> LENGTH: 7
<212> TYPE: PRT
<213> ORGANISM: Homo sapiens

<400> SEQUENCE: 98

Ser Ala Ser Arg Leu Val Glu
1               5

<210> SEQ ID NO 99
<211> LENGTH: 7
<212> TYPE: PRT
<213> ORGANISM: Homo sapiens

<400> SEQUENCE: 99

Arg Ala Gly Arg Leu Val Asp
1               5

<210> SEQ ID NO 100
<211> LENGTH: 7
<212> TYPE: PRT
<213> ORGANISM: Homo sapiens

<400> SEQUENCE: 100

Arg Ala Lys Arg Leu Ala Asn
1               5

<210> SEQ ID NO 101
<211> LENGTH: 7
<212> TYPE: PRT
<213> ORGANISM: Homo sapiens
```

```
<400> SEQUENCE: 101

Arg Ala Asn Arg Leu Glu Ala
1               5

<210> SEQ ID NO 102
<211> LENGTH: 7
<212> TYPE: PRT
<213> ORGANISM: Homo sapiens

<400> SEQUENCE: 102

Arg Ala Asn Gly Leu Val Glu
1               5

<210> SEQ ID NO 103
<211> LENGTH: 7
<212> TYPE: PRT
<213> ORGANISM: Homo sapiens

<400> SEQUENCE: 103

Arg Ala Asn Arg Leu Gly Asp
1               5

<210> SEQ ID NO 104
<211> LENGTH: 7
<212> TYPE: PRT
<213> ORGANISM: Homo sapiens

<400> SEQUENCE: 104

Arg Ala Asn Arg Met Glu Asp
1               5

<210> SEQ ID NO 105
<211> LENGTH: 7
<212> TYPE: PRT
<213> ORGANISM: Homo sapiens

<400> SEQUENCE: 105

Arg Ala Asn Arg Leu Glu Asp
1               5

<210> SEQ ID NO 106
<211> LENGTH: 7
<212> TYPE: PRT
<213> ORGANISM: Homo sapiens

<400> SEQUENCE: 106

Arg Ala Asn Arg Val Met Asp
1               5

<210> SEQ ID NO 107
<211> LENGTH: 7
<212> TYPE: PRT
<213> ORGANISM: Homo sapiens

<400> SEQUENCE: 107

Arg Ala Asn Arg Leu Glu Asp
1               5

<210> SEQ ID NO 108
<211> LENGTH: 7
<212> TYPE: PRT
<213> ORGANISM: Homo sapiens

<400> SEQUENCE: 108

Arg Ala Ser Arg Leu Glu Gly
```

<210> SEQ ID NO 109
<211> LENGTH: 7
<212> TYPE: PRT
<213> ORGANISM: Homo sapiens

<400> SEQUENCE: 109

Arg Ala Tyr Arg Ile Glu Asp
1               5

<210> SEQ ID NO 110
<211> LENGTH: 7
<212> TYPE: PRT
<213> ORGANISM: Homo sapiens

<400> SEQUENCE: 110

Arg Ala Tyr Tyr Leu Val Asp
1               5

<210> SEQ ID NO 111
<211> LENGTH: 7
<212> TYPE: PRT
<213> ORGANISM: Homo sapiens

<400> SEQUENCE: 111

Arg Gly Lys His Ile Glu Asp
1               5

<210> SEQ ID NO 112
<211> LENGTH: 7
<212> TYPE: PRT
<213> ORGANISM: Homo sapiens

<400> SEQUENCE: 112

Arg Gly Asn Arg Leu Glu Asn
1               5

<210> SEQ ID NO 113
<211> LENGTH: 7
<212> TYPE: PRT
<213> ORGANISM: Homo sapiens

<400> SEQUENCE: 113

Arg Gly Asn Arg Leu Glu Gly
1               5

<210> SEQ ID NO 114
<211> LENGTH: 7
<212> TYPE: PRT
<213> ORGANISM: Homo sapiens

<400> SEQUENCE: 114

Arg Gly Ser Arg Leu Glu Asp
1               5

<210> SEQ ID NO 115
<211> LENGTH: 7
<212> TYPE: PRT
<213> ORGANISM: Homo sapiens

<400> SEQUENCE: 115

Arg Ser Arg Arg Leu Glu Asn
1               5

```
<210> SEQ ID NO 116
<211> LENGTH: 7
<212> TYPE: PRT
<213> ORGANISM: Homo sapiens

<400> SEQUENCE: 116

Arg Thr Asn Arg Leu Arg Glu
1               5

<210> SEQ ID NO 117
<211> LENGTH: 7
<212> TYPE: PRT
<213> ORGANISM: Homo sapiens

<400> SEQUENCE: 117

Gln Ala Glu Arg Gln Pro Glu
1               5

<210> SEQ ID NO 118
<211> LENGTH: 7
<212> TYPE: PRT
<213> ORGANISM: Homo sapiens

<400> SEQUENCE: 118

Gln Gly Asn Arg Leu Val Asp
1               5

<210> SEQ ID NO 119
<211> LENGTH: 7
<212> TYPE: PRT
<213> ORGANISM: Homo sapiens

<400> SEQUENCE: 119

His Ala Ile Arg His Arg Asp
1               5

<210> SEQ ID NO 120
<211> LENGTH: 7
<212> TYPE: PRT
<213> ORGANISM: Homo sapiens

<400> SEQUENCE: 120

His Ala Asn Arg Leu Glu Asp
1               5

<210> SEQ ID NO 121
<211> LENGTH: 7
<212> TYPE: PRT
<213> ORGANISM: Homo sapiens

<400> SEQUENCE: 121

His Ala Asn Arg Gln Arg Asp
1               5

<210> SEQ ID NO 122
<211> LENGTH: 7
<212> TYPE: PRT
<213> ORGANISM: Homo sapiens

<400> SEQUENCE: 122

His Ala Ser Arg Leu Val Asp
1               5

<210> SEQ ID NO 123
<211> LENGTH: 7
<212> TYPE: PRT
```

<213> ORGANISM: Homo sapiens

<400> SEQUENCE: 123

His Gly Asn Arg Leu Val Asp
1               5

<210> SEQ ID NO 124
<211> LENGTH: 7
<212> TYPE: PRT
<213> ORGANISM: Homo sapiens

<400> SEQUENCE: 124

His Ser Asn Arg Leu Glu Asp
1               5

<210> SEQ ID NO 125
<211> LENGTH: 7
<212> TYPE: PRT
<213> ORGANISM: Homo sapiens

<400> SEQUENCE: 125

His Ser Asn Leu Leu Val Asn
1               5

<210> SEQ ID NO 126
<211> LENGTH: 7
<212> TYPE: PRT
<213> ORGANISM: Homo sapiens

<400> SEQUENCE: 126

His Ser Asn Arg Leu Glu Ala
1               5

<210> SEQ ID NO 127
<211> LENGTH: 7
<212> TYPE: PRT
<213> ORGANISM: Homo sapiens

<400> SEQUENCE: 127

Gly Ala Lys Arg Leu Arg Asp
1               5

<210> SEQ ID NO 128
<211> LENGTH: 9
<212> TYPE: PRT
<213> ORGANISM: Homo sapiens

<400> SEQUENCE: 128

Leu Ser Tyr Asp Glu Phe Pro Leu Thr
1               5

<210> SEQ ID NO 129
<211> LENGTH: 9
<212> TYPE: PRT
<213> ORGANISM: Homo sapiens

<400> SEQUENCE: 129

Leu Gln Tyr Asp Gly Phe Pro Leu Thr
1               5

<210> SEQ ID NO 130
<211> LENGTH: 9
<212> TYPE: PRT
<213> ORGANISM: Homo sapiens

<400> SEQUENCE: 130

Leu Gln Tyr Asp Lys Phe Pro Leu Thr
1               5

<210> SEQ ID NO 131
<211> LENGTH: 9
<212> TYPE: PRT
<213> ORGANISM: Homo sapiens

<400> SEQUENCE: 131

Leu Gln Tyr Asp Thr Phe Pro Leu Thr
1               5

<210> SEQ ID NO 132
<211> LENGTH: 9
<212> TYPE: PRT
<213> ORGANISM: Homo sapiens

<400> SEQUENCE: 132

Leu Gln Tyr Ser Glu Phe Pro Leu Thr
1               5

<210> SEQ ID NO 133
<211> LENGTH: 9
<212> TYPE: PRT
<213> ORGANISM: Homo sapiens

<400> SEQUENCE: 133

Leu Gln Tyr Asp Glu Met Pro Leu Thr
1               5

<210> SEQ ID NO 134
<211> LENGTH: 9
<212> TYPE: PRT
<213> ORGANISM: Homo sapiens

<400> SEQUENCE: 134

Leu Gln Tyr Asp Glu Phe Pro Leu Ser
1               5

<210> SEQ ID NO 135
<211> LENGTH: 9
<212> TYPE: PRT
<213> ORGANISM: Homo sapiens

<400> SEQUENCE: 135

Leu Thr Tyr Asp Asp Phe Pro Leu Thr
1               5

<210> SEQ ID NO 136
<211> LENGTH: 9
<212> TYPE: PRT
<213> ORGANISM: Homo sapiens

<400> SEQUENCE: 136

Met Thr Tyr Asp Asn Phe Pro Leu Thr
1               5

<210> SEQ ID NO 137
<211> LENGTH: 9
<212> TYPE: PRT
<213> ORGANISM: Homo sapiens

<400> SEQUENCE: 137

Leu Ser Tyr Asp Glu Phe Pro Leu Thr
1               5

```
<210> SEQ ID NO 138
<211> LENGTH: 9
<212> TYPE: PRT
<213> ORGANISM: Homo sapiens

<400> SEQUENCE: 138

Leu Ser Tyr Asp Asp Phe Pro Leu Thr
1               5

<210> SEQ ID NO 139
<211> LENGTH: 9
<212> TYPE: PRT
<213> ORGANISM: Homo sapiens

<400> SEQUENCE: 139

Leu Gln Tyr Ala Val Phe Pro Leu Thr
1               5

<210> SEQ ID NO 140
<211> LENGTH: 9
<212> TYPE: PRT
<213> ORGANISM: Homo sapiens

<400> SEQUENCE: 140

Met Gln Tyr Ala Asp Phe Pro Leu Thr
1               5

<210> SEQ ID NO 141
<211> LENGTH: 9
<212> TYPE: PRT
<213> ORGANISM: Homo sapiens

<400> SEQUENCE: 141

Leu Gln Tyr Asp Gly Phe Pro Leu Ile
1               5

<210> SEQ ID NO 142
<211> LENGTH: 9
<212> TYPE: PRT
<213> ORGANISM: Homo sapiens

<400> SEQUENCE: 142

Leu Gln Tyr Asp Val Phe Pro Leu Thr
1               5

<210> SEQ ID NO 143
<211> LENGTH: 9
<212> TYPE: PRT
<213> ORGANISM: Homo sapiens

<400> SEQUENCE: 143

Gln Gln Tyr Asp Glu Phe Pro Leu Thr
1               5

<210> SEQ ID NO 144
<211> LENGTH: 9
<212> TYPE: PRT
<213> ORGANISM: Homo sapiens

<400> SEQUENCE: 144

Leu Gln Tyr Glu Val Phe Pro Leu Ile
1               5

<210> SEQ ID NO 145
```

<211> LENGTH: 9
<212> TYPE: PRT
<213> ORGANISM: Homo sapiens

<400> SEQUENCE: 145

Leu Gln Tyr Gly Val Phe Pro Leu Val
1               5

<210> SEQ ID NO 146
<211> LENGTH: 9
<212> TYPE: PRT
<213> ORGANISM: Homo sapiens

<400> SEQUENCE: 146

Met Gln Tyr Gly Tyr Phe Pro Leu Ser
1               5

<210> SEQ ID NO 147
<211> LENGTH: 9
<212> TYPE: PRT
<213> ORGANISM: Homo sapiens

<400> SEQUENCE: 147

Met Gln Tyr His Ala Phe Ala Leu Thr
1               5

<210> SEQ ID NO 148
<211> LENGTH: 9
<212> TYPE: PRT
<213> ORGANISM: Homo sapiens

<400> SEQUENCE: 148

Met Asn Tyr Asp Val Phe Pro Leu Thr
1               5

<210> SEQ ID NO 149
<211> LENGTH: 9
<212> TYPE: PRT
<213> ORGANISM: Homo sapiens

<400> SEQUENCE: 149

Leu Asn Tyr Tyr Glu Phe Pro Leu Thr
1               5

<210> SEQ ID NO 150
<211> LENGTH: 9
<212> TYPE: PRT
<213> ORGANISM: Homo sapiens

<400> SEQUENCE: 150

Leu Lys Asp Asp Glu Met Pro Leu Thr
1               5

<210> SEQ ID NO 151
<211> LENGTH: 9
<212> TYPE: PRT
<213> ORGANISM: Homo sapiens

<400> SEQUENCE: 151

Leu His Tyr Gly Glu Phe Pro Leu Thr
1               5

<210> SEQ ID NO 152
<211> LENGTH: 9
<212> TYPE: PRT
<213> ORGANISM: Homo sapiens

<400> SEQUENCE: 152

Met Glu Phe Asn Asp Phe Pro Leu Thr
1               5

<210> SEQ ID NO 153
<211> LENGTH: 9
<212> TYPE: PRT
<213> ORGANISM: Homo sapiens

<400> SEQUENCE: 153

Met Asp Tyr Asp Ile Phe Pro Leu Thr
1               5

<210> SEQ ID NO 154
<211> LENGTH: 9
<212> TYPE: PRT
<213> ORGANISM: Homo sapiens

<400> SEQUENCE: 154

Met Asp Tyr Val Glu Phe Pro Leu Thr
1               5

<210> SEQ ID NO 155
<211> LENGTH: 9
<212> TYPE: PRT
<213> ORGANISM: Homo sapiens

<400> SEQUENCE: 155

Leu Ala Tyr Ala Asp Phe Pro Leu Thr
1               5

<210> SEQ ID NO 156
<211> LENGTH: 10
<212> TYPE: PRT
<213> ORGANISM: Homo sapiens

<400> SEQUENCE: 156

Gly Phe Arg Leu Ala Thr Tyr Gly Val His
1               5                   10

<210> SEQ ID NO 157
<211> LENGTH: 10
<212> TYPE: PRT
<213> ORGANISM: Homo sapiens

<400> SEQUENCE: 157

Gly Phe Ser Ile Ile Thr Tyr Gly Val His
1               5                   10

<210> SEQ ID NO 158
<211> LENGTH: 10
<212> TYPE: PRT
<213> ORGANISM: Homo sapiens

<400> SEQUENCE: 158

Gly Phe Ser Leu Ile Thr Tyr Gly Val Gln
1               5                   10

<210> SEQ ID NO 159
<211> LENGTH: 10
<212> TYPE: PRT
<213> ORGANISM: Homo sapiens

<400> SEQUENCE: 159

Gly Phe Ser Leu Lys Thr Tyr Gly Val His
1               5                   10

<210> SEQ ID NO 160
<211> LENGTH: 10
<212> TYPE: PRT
<213> ORGANISM: Homo sapiens

<400> SEQUENCE: 160

Gly Phe Ser Leu Asn Thr Tyr Gly Val His
1               5                   10

<210> SEQ ID NO 161
<211> LENGTH: 10
<212> TYPE: PRT
<213> ORGANISM: Homo sapiens

<400> SEQUENCE: 161

Gly Phe Ser Leu Asn Ser Tyr Gly Ala His
1               5                   10

<210> SEQ ID NO 162
<211> LENGTH: 10
<212> TYPE: PRT
<213> ORGANISM: Homo sapiens

<400> SEQUENCE: 162

Gly Tyr Ser Val Asn Thr Tyr Gly Gly His
1               5                   10

<210> SEQ ID NO 163
<211> LENGTH: 10
<212> TYPE: PRT
<213> ORGANISM: Homo sapiens

<400> SEQUENCE: 163

Gly Phe Ser Phe Arg Ser Tyr Gly Val His
1               5                   10

<210> SEQ ID NO 164
<211> LENGTH: 10
<212> TYPE: PRT
<213> ORGANISM: Homo sapiens

<400> SEQUENCE: 164

Gly Phe Ser Ile Ser Thr Tyr Gly Ala His
1               5                   10

<210> SEQ ID NO 165
<211> LENGTH: 10
<212> TYPE: PRT
<213> ORGANISM: Homo sapiens

<400> SEQUENCE: 165

Gly Phe Ser Leu Ser Thr Tyr Gly Ala His
1               5                   10

<210> SEQ ID NO 166
<211> LENGTH: 10
<212> TYPE: PRT
<213> ORGANISM: Homo sapiens

<400> SEQUENCE: 166

Gly Phe Ser Leu Ser Thr Tyr Gly Val Gln
1               5                   10

<210> SEQ ID NO 167
<211> LENGTH: 10
<212> TYPE: PRT
<213> ORGANISM: Homo sapiens

<400> SEQUENCE: 167

Gly Phe Ser Leu Ser Thr Tyr Gly Ala Tyr
1               5                   10

<210> SEQ ID NO 168
<211> LENGTH: 10
<212> TYPE: PRT
<213> ORGANISM: Homo sapiens

<400> SEQUENCE: 168

Gly Phe Ser Phe Thr Thr Tyr Gly Ala His
1               5                   10

<210> SEQ ID NO 169
<211> LENGTH: 10
<212> TYPE: PRT
<213> ORGANISM: Homo sapiens

<400> SEQUENCE: 169

Gly Phe Ser Ile Thr Thr Tyr Gly Gly His
1               5                   10

<210> SEQ ID NO 170
<211> LENGTH: 10
<212> TYPE: PRT
<213> ORGANISM: Homo sapiens

<400> SEQUENCE: 170

Gly Phe Ser Leu Thr Thr Tyr Gly Ala His
1               5                   10

<210> SEQ ID NO 171
<211> LENGTH: 10
<212> TYPE: PRT
<213> ORGANISM: Homo sapiens

<400> SEQUENCE: 171

Gly Phe Gly Leu Thr Ser Phe Gly Val His
1               5                   10

<210> SEQ ID NO 172
<211> LENGTH: 10
<212> TYPE: PRT
<213> ORGANISM: Homo sapiens

<400> SEQUENCE: 172

Gly Phe Gly Leu Thr Arg Tyr Gly Val His
1               5                   10

<210> SEQ ID NO 173
<211> LENGTH: 10
<212> TYPE: PRT
<213> ORGANISM: Homo sapiens

<400> SEQUENCE: 173

Gly Phe Asn Met Thr Thr Tyr Gly Val His
1               5                   10

<210> SEQ ID NO 174
<211> LENGTH: 10

```
<212> TYPE: PRT
<213> ORGANISM: Homo sapiens

<400> SEQUENCE: 174

Gly Phe Asp Val Thr Thr Tyr Gly Val His
1               5                   10

<210> SEQ ID NO 175
<211> LENGTH: 10
<212> TYPE: PRT
<213> ORGANISM: Homo sapiens

<400> SEQUENCE: 175

Gly Phe Arg Leu Thr Ser Tyr Gly Val Gln
1               5                   10

<210> SEQ ID NO 176
<211> LENGTH: 10
<212> TYPE: PRT
<213> ORGANISM: Homo sapiens

<400> SEQUENCE: 176

Gly Phe Ser Leu Thr Thr Tyr Gly Ala Gln
1               5                   10

<210> SEQ ID NO 177
<211> LENGTH: 17
<212> TYPE: PRT
<213> ORGANISM: Homo sapiens

<400> SEQUENCE: 177

Gly Val Ile Trp Pro Gly Gly Gly Thr Asp Tyr Asn Ala Arg Phe Ile
1               5                   10                  15

Ser

<210> SEQ ID NO 178
<211> LENGTH: 17
<212> TYPE: PRT
<213> ORGANISM: Homo sapiens

<400> SEQUENCE: 178

Gly Val Ile Trp Pro Gly Gly Gly Thr Asp Tyr Asn Glu Ala Phe Ile
1               5                   10                  15

Ser

<210> SEQ ID NO 179
<211> LENGTH: 17
<212> TYPE: PRT
<213> ORGANISM: Homo sapiens

<400> SEQUENCE: 179

Gly Val Ile Trp Pro Gly Gly Gly Thr Asp Tyr Asn Ala Ala Phe Thr
1               5                   10                  15

Ser

<210> SEQ ID NO 180
<211> LENGTH: 17
<212> TYPE: PRT
<213> ORGANISM: Homo sapiens

<400> SEQUENCE: 180

Gly Ile Ile Trp Pro Gly Gly Gly Ile Asp Tyr Asn Glu Ala Phe Ile
1               5                   10                  15
```

<210> SEQ ID NO 181
<211> LENGTH: 17
<212> TYPE: PRT
<213> ORGANISM: Homo sapiens

<400> SEQUENCE: 181

Gly Ile Ile Trp Pro Gly Gly Gly Thr Asp Tyr Asn Ala Glu Phe Glu
1               5                   10                  15
Thr

<210> SEQ ID NO 182
<211> LENGTH: 17
<212> TYPE: PRT
<213> ORGANISM: Homo sapiens

<400> SEQUENCE: 182

Gly Ile Ile Trp Pro Gly Gly Gly Thr Asp Tyr Asn Ala Ala Phe Ile
1               5                   10                  15
Ser

<210> SEQ ID NO 183
<211> LENGTH: 17
<212> TYPE: PRT
<213> ORGANISM: Homo sapiens

<400> SEQUENCE: 183

Gly Leu Ser Trp Pro Gly Gly Gly Ile Glu Glu Asn Ala Leu Phe Asn
1               5                   10                  15
Arg

<210> SEQ ID NO 184
<211> LENGTH: 17
<212> TYPE: PRT
<213> ORGANISM: Homo sapiens

<400> SEQUENCE: 184

Gly Leu Ile Trp Pro Gly Gly Gly Ile Asp Tyr Gly Ala Glu Phe Leu
1               5                   10                  15
Asn

<210> SEQ ID NO 185
<211> LENGTH: 17
<212> TYPE: PRT
<213> ORGANISM: Homo sapiens

<400> SEQUENCE: 185

Gly Leu Ile Trp Pro Gly Gly Gly Ile Asp Tyr Asn Ala Ala Phe Ile
1               5                   10                  15
Ser

<210> SEQ ID NO 186
<211> LENGTH: 17
<212> TYPE: PRT
<213> ORGANISM: Homo sapiens

<400> SEQUENCE: 186

Gly Leu Met Trp Pro Gly Gly Gly Ile Asp Ser Asn Glu Ala Phe Ile
1               5                   10                  15
Gly

<210> SEQ ID NO 187
<211> LENGTH: 17
<212> TYPE: PRT
<213> ORGANISM: Homo sapiens

<400> SEQUENCE: 187

Gly Leu Ile Trp Pro Gly Gly Ala Ile Asp Leu Asn Lys Gly Phe Ile
1               5                   10                  15
Asn

<210> SEQ ID NO 188
<211> LENGTH: 17
<212> TYPE: PRT
<213> ORGANISM: Homo sapiens

<400> SEQUENCE: 188

Gly Leu Ile Trp Pro Gly Gly Ile Asp Tyr Asn Ser Ala Phe Ile
1               5                   10                  15
Arg

<210> SEQ ID NO 189
<211> LENGTH: 17
<212> TYPE: PRT
<213> ORGANISM: Homo sapiens

<400> SEQUENCE: 189

Gly Leu Ile Trp Pro Gly Gly Leu Asp Tyr Asn Gly Ala Phe Ile
1               5                   10                  15
Lys

<210> SEQ ID NO 190
<211> LENGTH: 17
<212> TYPE: PRT
<213> ORGANISM: Homo sapiens

<400> SEQUENCE: 190

Gly Leu Ser Trp Pro Ala Gly Ser Asp Tyr Asn Ala Phe Leu Ser
1               5                   10                  15
Ser

<210> SEQ ID NO 191
<211> LENGTH: 17
<212> TYPE: PRT
<213> ORGANISM: Homo sapiens

<400> SEQUENCE: 191

Gly Leu Val Trp Pro Gly Gly Ser Asp Phe Asn Ala Ala Phe Ser
1               5                   10                  15
Arg

<210> SEQ ID NO 192
<211> LENGTH: 17
<212> TYPE: PRT
<213> ORGANISM: Homo sapiens

<400> SEQUENCE: 192

Gly Leu Ile Trp Pro Gly Gly Thr Asp Tyr Asn Ala Ala Phe Ile
1               5                   10                  15
Ser

<210> SEQ ID NO 193

-continued

```
<211> LENGTH: 17
<212> TYPE: PRT
<213> ORGANISM: Homo sapiens

<400> SEQUENCE: 193

Gly Leu Met Trp Pro Gly Gly Gly Thr Asp Tyr Asn Ala Ala Phe Val
1               5                   10                  15

Ser

<210> SEQ ID NO 194
<211> LENGTH: 17
<212> TYPE: PRT
<213> ORGANISM: Homo sapiens

<400> SEQUENCE: 194

Gly Leu Val Trp Pro Gly Gly Gly Thr Asp Tyr Asn Ala Ala Phe Ile
1               5                   10                  15

Ser

<210> SEQ ID NO 195
<211> LENGTH: 17
<212> TYPE: PRT
<213> ORGANISM: Homo sapiens

<400> SEQUENCE: 195

Gly Leu Leu Trp Pro Gly Gly Gly Thr Asp Leu Asn Ala Ala Phe Ile
1               5                   10                  15

Gly

<210> SEQ ID NO 196
<211> LENGTH: 17
<212> TYPE: PRT
<213> ORGANISM: Homo sapiens

<400> SEQUENCE: 196

Gly Leu Ile Trp Pro Gly Gly Gly Thr Asp Ile Asn Ala Ala Phe Ile
1               5                   10                  15

Ser

<210> SEQ ID NO 197
<211> LENGTH: 17
<212> TYPE: PRT
<213> ORGANISM: Homo sapiens

<400> SEQUENCE: 197

Gly Leu Phe Trp Pro Gly Gly Gly Thr Asp Tyr Asn Glu Ala Phe Leu
1               5                   10                  15

Gly

<210> SEQ ID NO 198
<211> LENGTH: 17
<212> TYPE: PRT
<213> ORGANISM: Homo sapiens

<400> SEQUENCE: 198

Gly Leu Ile Trp Pro Gly Gly Gly Thr Asp Val Asn Lys Ala Leu Ile
1               5                   10                  15

Ser

<210> SEQ ID NO 199
<211> LENGTH: 17
<212> TYPE: PRT
```

```
<213> ORGANISM: Homo sapiens

<400> SEQUENCE: 199

Gly Leu Val Trp Pro Gly Gly Thr Asp Tyr Asn Pro Glu Phe Ile
1               5                   10                  15

Ser

<210> SEQ ID NO 200
<211> LENGTH: 17
<212> TYPE: PRT
<213> ORGANISM: Homo sapiens

<400> SEQUENCE: 200

Gly Leu Leu Trp Pro Gly Gly Thr Asp Tyr Asn Ser Asp Val Leu
1               5                   10                  15

Gly

<210> SEQ ID NO 201
<211> LENGTH: 17
<212> TYPE: PRT
<213> ORGANISM: Homo sapiens

<400> SEQUENCE: 201

Gly Leu Ile Trp Pro Gly Gly Thr Asp Leu Asn Thr Ala Phe Ile
1               5                   10                  15

Pro

<210> SEQ ID NO 202
<211> LENGTH: 17
<212> TYPE: PRT
<213> ORGANISM: Homo sapiens

<400> SEQUENCE: 202

Gly Leu Ile Trp Pro Gly Gly Thr Asp Tyr Asn Thr Thr Leu Ser
1               5                   10                  15

Ser

<210> SEQ ID NO 203
<211> LENGTH: 17
<212> TYPE: PRT
<213> ORGANISM: Homo sapiens

<400> SEQUENCE: 203

Gly Leu Val Trp Pro Gly Gly Thr Asp Tyr Asn Thr Ala Leu Asn
1               5                   10                  15

Ser

<210> SEQ ID NO 204
<211> LENGTH: 17
<212> TYPE: PRT
<213> ORGANISM: Homo sapiens

<400> SEQUENCE: 204

Gly Met Ile Trp Pro Gly Gly Gly Ile Asp Tyr Asn Ala Gly Leu Ile
1               5                   10                  15

Ser

<210> SEQ ID NO 205
<211> LENGTH: 17
<212> TYPE: PRT
<213> ORGANISM: Homo sapiens
```

```
<400> SEQUENCE: 205

Gly Met Tyr Trp Pro Gly Gly Gly Ile Glu Phe Asn Ala Ala Phe Ile
1               5                   10                  15

Ser

<210> SEQ ID NO 206
<211> LENGTH: 17
<212> TYPE: PRT
<213> ORGANISM: Homo sapiens

<400> SEQUENCE: 206

Gly Met Ile Trp Pro Gly Gly Thr Ser Glu Phe Asn Ser Glu Phe Ile
1               5                   10                  15

Ser

<210> SEQ ID NO 207
<211> LENGTH: 17
<212> TYPE: PRT
<213> ORGANISM: Homo sapiens

<400> SEQUENCE: 207

Gly Met Ile Trp Pro Gly Gly Thr Asp Leu Asn Glu Ala Phe Met
1               5                   10                  15

Arg

<210> SEQ ID NO 208
<211> LENGTH: 17
<212> TYPE: PRT
<213> ORGANISM: Homo sapiens

<400> SEQUENCE: 208

Gly Met Met Trp Pro Gly Gly Thr Glu Tyr Asn Gly Ala Ser Asn
1               5                   10                  15

Gly

<210> SEQ ID NO 209
<211> LENGTH: 17
<212> TYPE: PRT
<213> ORGANISM: Homo sapiens

<400> SEQUENCE: 209

Gly Met Ile Trp Pro Gly Gly Thr Asp Tyr Lys Thr Ser Leu Thr
1               5                   10                  15

Ser

<210> SEQ ID NO 210
<211> LENGTH: 17
<212> TYPE: PRT
<213> ORGANISM: Homo sapiens

<400> SEQUENCE: 210

Gly Met Ile Trp Pro Gly Gly Thr Asp Tyr Asn Thr Ala Phe Ile
1               5                   10                  15

Ser

<210> SEQ ID NO 211
<211> LENGTH: 17
<212> TYPE: PRT
<213> ORGANISM: Homo sapiens

<400> SEQUENCE: 211
```

```
Gly Met Leu Trp Pro Gly Gly Ser Val Asp Tyr Asn Ala Ala Phe Ile
1               5                   10                  15

Asn

<210> SEQ ID NO 212
<211> LENGTH: 17
<212> TYPE: PRT
<213> ORGANISM: Homo sapiens

<400> SEQUENCE: 212

Gly Val Ile Trp Pro Gly Gly Tyr Ile Asp Tyr Asn Ala Gly Phe Ile
1               5                   10                  15

Ser

<210> SEQ ID NO 213
<211> LENGTH: 17
<212> TYPE: PRT
<213> ORGANISM: Homo sapiens

<400> SEQUENCE: 213

Gly Val Ile Trp Pro Gly Gly Arg Ile Asp Tyr Asn Glu Gly Phe Ile
1               5                   10                  15

Ser

<210> SEQ ID NO 214
<211> LENGTH: 17
<212> TYPE: PRT
<213> ORGANISM: Homo sapiens

<400> SEQUENCE: 214

Gly Val Phe Trp Pro Gly Gly Gly Ile Asp Tyr Asn Pro Ser Phe Ile
1               5                   10                  15

Ala

<210> SEQ ID NO 215
<211> LENGTH: 17
<212> TYPE: PRT
<213> ORGANISM: Homo sapiens

<400> SEQUENCE: 215

Gly Val Ile Trp Pro Gly Gly Gly Ile Asp Tyr Asn Thr Ala Phe Ile
1               5                   10                  15

Ser

<210> SEQ ID NO 216
<211> LENGTH: 17
<212> TYPE: PRT
<213> ORGANISM: Homo sapiens

<400> SEQUENCE: 216

Gly Val Tyr Trp Pro Gly Gly Gly Ser Asp Trp Ala Glu Lys Phe Ala
1               5                   10                  15

Ser

<210> SEQ ID NO 217
<211> LENGTH: 17
<212> TYPE: PRT
<213> ORGANISM: Homo sapiens

<400> SEQUENCE: 217

Gly Val Val Trp Pro Gly Gly Ser Ser Asp Phe Lys Lys Glu Phe Thr
1               5                   10                  15
```

Ser

<210> SEQ ID NO 218
<211> LENGTH: 17
<212> TYPE: PRT
<213> ORGANISM: Homo sapiens

<400> SEQUENCE: 218

Gly Val Ile Trp Pro Gly Gly Gly Ser Asp Phe Thr Ser Arg Phe His
1               5                   10                  15

Asp

<210> SEQ ID NO 219
<211> LENGTH: 17
<212> TYPE: PRT
<213> ORGANISM: Homo sapiens

<400> SEQUENCE: 219

Gly Val Ile Trp Pro Gly Gly Gly Ser Asp Tyr Asn Thr Ala Phe Gly
1               5                   10                  15

Arg

<210> SEQ ID NO 220
<211> LENGTH: 17
<212> TYPE: PRT
<213> ORGANISM: Homo sapiens

<400> SEQUENCE: 220

Gly Val Ile Trp Pro Gly Gly Gly Ser Asp Tyr Lys Thr Glu Phe Ile
1               5                   10                  15

Gly

<210> SEQ ID NO 221
<211> LENGTH: 17
<212> TYPE: PRT
<213> ORGANISM: Homo sapiens

<400> SEQUENCE: 221

Gly Val Ile Trp Pro Gly Gly Arg Thr Asp Leu Asn Ala Ala Phe Ile
1               5                   10                  15

Ser

<210> SEQ ID NO 222
<211> LENGTH: 17
<212> TYPE: PRT
<213> ORGANISM: Homo sapiens

<400> SEQUENCE: 222

Ser Val Thr Trp Pro Gly Gly Ser Thr Asp Phe Asn Pro Ala Phe Leu
1               5                   10                  15

Gly

<210> SEQ ID NO 223
<211> LENGTH: 17
<212> TYPE: PRT
<213> ORGANISM: Homo sapiens

<400> SEQUENCE: 223

Ser Val Thr Trp Pro Gly Gly Gly Thr Asn Phe Asn Pro Ala Phe Asp
1               5                   10                  15

Arg

```
<210> SEQ ID NO 224
<211> LENGTH: 17
<212> TYPE: PRT
<213> ORGANISM: Homo sapiens

<400> SEQUENCE: 224

Gly Val Ile Trp Pro Gly Gly Ala Thr Ala Tyr Asn Ser Asp Val Ile
1               5                   10                  15

Ser

<210> SEQ ID NO 225
<211> LENGTH: 17
<212> TYPE: PRT
<213> ORGANISM: Homo sapiens

<400> SEQUENCE: 225

Gly Val Val Trp Pro Gly Gly Gly Thr Asn Phe Ser Ser Ala Leu Ser
1               5                   10                  15

Gly

<210> SEQ ID NO 226
<211> LENGTH: 17
<212> TYPE: PRT
<213> ORGANISM: Homo sapiens

<400> SEQUENCE: 226

Gly Val Ile Trp Pro Gly Gly Gly Thr Asp Ile Asn Thr Ala Leu Asn
1               5                   10                  15

Ser

<210> SEQ ID NO 227
<211> LENGTH: 17
<212> TYPE: PRT
<213> ORGANISM: Homo sapiens

<400> SEQUENCE: 227

Gly Val Val Trp Pro Gly Gly Gly Thr Asp Trp Thr Thr Ala Val Ser
1               5                   10                  15

Gly

<210> SEQ ID NO 228
<211> LENGTH: 17
<212> TYPE: PRT
<213> ORGANISM: Homo sapiens

<400> SEQUENCE: 228

Gly Val Ile Trp Pro Gly Gly Gly Thr His Tyr Asn Thr Ala Phe Phe
1               5                   10                  15

Arg

<210> SEQ ID NO 229
<211> LENGTH: 17
<212> TYPE: PRT
<213> ORGANISM: Homo sapiens

<400> SEQUENCE: 229

Gly Val Ile Trp Pro Gly Gly Ser Tyr Asp Trp Asn Gly Ala Phe Asn
1               5                   10                  15

Glu
```

```
<210> SEQ ID NO 230
<211> LENGTH: 13
<212> TYPE: PRT
<213> ORGANISM: Homo sapiens

<400> SEQUENCE: 230

Val Arg Lys Glu Tyr Ala Asn Leu Tyr Arg Met Asp Tyr
1               5                   10

<210> SEQ ID NO 231
<211> LENGTH: 13
<212> TYPE: PRT
<213> ORGANISM: Homo sapiens

<400> SEQUENCE: 231

Val Arg Lys Glu Tyr Ala Asn Leu Tyr Lys Met Asp Tyr
1               5                   10

<210> SEQ ID NO 232
<211> LENGTH: 13
<212> TYPE: PRT
<213> ORGANISM: Homo sapiens

<400> SEQUENCE: 232

Val Arg Lys Glu Tyr Ala Asn Leu Tyr Gln Met Asp Tyr
1               5                   10

<210> SEQ ID NO 233
<211> LENGTH: 13
<212> TYPE: PRT
<213> ORGANISM: Homo sapiens

<400> SEQUENCE: 233

Val Arg Lys Glu Tyr Ala Asn Leu Tyr Ala Leu Asp Tyr
1               5                   10

<210> SEQ ID NO 234
<211> LENGTH: 13
<212> TYPE: PRT
<213> ORGANISM: Homo sapiens

<400> SEQUENCE: 234

Val Arg Lys Glu Tyr Ala Asn Leu Tyr Ala Met Thr Tyr
1               5                   10

<210> SEQ ID NO 235
<211> LENGTH: 13
<212> TYPE: PRT
<213> ORGANISM: Homo sapiens

<400> SEQUENCE: 235

Val Arg Lys Glu Tyr Ala Asn Leu Tyr Ala Met Asp His
1               5                   10

<210> SEQ ID NO 236
<211> LENGTH: 13
<212> TYPE: PRT
<213> ORGANISM: Homo sapiens

<400> SEQUENCE: 236

Val Arg Lys Ala Tyr Ala Asn Leu Tyr Ala Met Asp Tyr
1               5                   10

<210> SEQ ID NO 237
<211> LENGTH: 13
<212> TYPE: PRT
```

<213> ORGANISM: Homo sapiens

<400> SEQUENCE: 237

Val Arg Lys Gly Tyr Ala Asn Leu Tyr Ala Met Asp Tyr
1               5                   10

<210> SEQ ID NO 238
<211> LENGTH: 13
<212> TYPE: PRT
<213> ORGANISM: Homo sapiens

<400> SEQUENCE: 238

Val Arg Lys Glu Tyr Ala Asn Leu Tyr Ala Phe His Phe
1               5                   10

<210> SEQ ID NO 239
<211> LENGTH: 13
<212> TYPE: PRT
<213> ORGANISM: Homo sapiens

<400> SEQUENCE: 239

Val Arg Lys Glu Tyr Ala Asn Val Tyr Ala Leu Glu Tyr
1               5                   10

<210> SEQ ID NO 240
<211> LENGTH: 13
<212> TYPE: PRT
<213> ORGANISM: Homo sapiens

<400> SEQUENCE: 240

Val Arg Lys Glu Tyr Gly Asn Leu Tyr Ala Leu Asn Tyr
1               5                   10

<210> SEQ ID NO 241
<211> LENGTH: 13
<212> TYPE: PRT
<213> ORGANISM: Homo sapiens

<400> SEQUENCE: 241

Val Arg Lys Gly Tyr Ala Ser Leu Tyr Ala Met Asp Tyr
1               5                   10

<210> SEQ ID NO 242
<211> LENGTH: 13
<212> TYPE: PRT
<213> ORGANISM: Homo sapiens

<400> SEQUENCE: 242

Val Arg Lys Glu Tyr Ala Asn Leu Tyr Ala Met Asp Tyr
1               5                   10

<210> SEQ ID NO 243
<211> LENGTH: 13
<212> TYPE: PRT
<213> ORGANISM: Homo sapiens

<400> SEQUENCE: 243

Val Arg Lys Glu Tyr Ala Asn Leu Phe Ala Met Val Tyr
1               5                   10

<210> SEQ ID NO 244
<211> LENGTH: 13
<212> TYPE: PRT
<213> ORGANISM: Homo sapiens

<400> SEQUENCE: 244

Val Arg Lys Glu Tyr Ala Asn Leu Tyr Glu Leu Asn His
1               5                   10

<210> SEQ ID NO 245
<211> LENGTH: 13
<212> TYPE: PRT
<213> ORGANISM: Homo sapiens

<400> SEQUENCE: 245

Val Arg Lys Glu Tyr Ala Lys Leu Tyr Leu Ala Asp Tyr
1               5                   10

<210> SEQ ID NO 246
<211> LENGTH: 13
<212> TYPE: PRT
<213> ORGANISM: Homo sapiens

<400> SEQUENCE: 246

Val Arg Lys Glu Tyr Ala Asn Val Tyr Met Met His Tyr
1               5                   10

<210> SEQ ID NO 247
<211> LENGTH: 13
<212> TYPE: PRT
<213> ORGANISM: Homo sapiens

<400> SEQUENCE: 247

Val Arg Lys Glu Tyr Ala Thr Leu Tyr Pro Ser Ala Tyr
1               5                   10

<210> SEQ ID NO 248
<211> LENGTH: 13
<212> TYPE: PRT
<213> ORGANISM: Homo sapiens

<400> SEQUENCE: 248

Val Arg Lys Glu Tyr Ala Asn Leu Tyr Pro Ser Asp Tyr
1               5                   10

<210> SEQ ID NO 249
<211> LENGTH: 13
<212> TYPE: PRT
<213> ORGANISM: Homo sapiens

<400> SEQUENCE: 249

Val Arg Lys Lys Tyr Ala Lys Leu Tyr Pro Ser Asp Tyr
1               5                   10

<210> SEQ ID NO 250
<211> LENGTH: 13
<212> TYPE: PRT
<213> ORGANISM: Homo sapiens

<400> SEQUENCE: 250

Val Arg Lys Glu Tyr Ala Asn Val Tyr Pro Ser Asp Tyr
1               5                   10

<210> SEQ ID NO 251
<211> LENGTH: 13
<212> TYPE: PRT
<213> ORGANISM: Homo sapiens

<400> SEQUENCE: 251

Val Arg Lys Gln Tyr Ala Asn Leu Tyr Pro Ser Asp Tyr
1               5                   10

<210> SEQ ID NO 252
<211> LENGTH: 13
<212> TYPE: PRT
<213> ORGANISM: Homo sapiens

<400> SEQUENCE: 252

Val Arg Lys Gly Tyr Ala Phe Leu Tyr Pro Ser Asp Asn
1               5                   10

<210> SEQ ID NO 253
<211> LENGTH: 13
<212> TYPE: PRT
<213> ORGANISM: Homo sapiens

<400> SEQUENCE: 253

Val Arg Lys Gly Tyr Ala Thr Leu Tyr Pro Ser Gln Phe
1               5                   10

<210> SEQ ID NO 254
<211> LENGTH: 13
<212> TYPE: PRT
<213> ORGANISM: Homo sapiens

<400> SEQUENCE: 254

Val Arg Lys Gly Tyr Ala Ser Leu Tyr Pro Ser Tyr Tyr
1               5                   10

<210> SEQ ID NO 255
<211> LENGTH: 13
<212> TYPE: PRT
<213> ORGANISM: Homo sapiens

<400> SEQUENCE: 255

Val Arg Lys Glu Tyr Ala Asn Leu Tyr Gln Met Asp Tyr
1               5                   10

<210> SEQ ID NO 256
<211> LENGTH: 13
<212> TYPE: PRT
<213> ORGANISM: Homo sapiens

<400> SEQUENCE: 256

Val Arg Lys Glu Tyr Ala Asn Leu Ser Gln Met Val Tyr
1               5                   10

<210> SEQ ID NO 257
<211> LENGTH: 13
<212> TYPE: PRT
<213> ORGANISM: Homo sapiens

<400> SEQUENCE: 257

Val Arg Lys Glu Tyr Ala Asn Leu Tyr Arg Leu Asp Phe
1               5                   10

<210> SEQ ID NO 258
<211> LENGTH: 13
<212> TYPE: PRT
<213> ORGANISM: Homo sapiens

<400> SEQUENCE: 258

Val Arg Lys Glu Tyr Ala Asn Val Tyr Arg Met Asp Tyr
1               5                   10

<210> SEQ ID NO 259

<211> LENGTH: 13
<212> TYPE: PRT
<213> ORGANISM: Homo sapiens

<400> SEQUENCE: 259

Val Arg Lys Glu Tyr Ala Asn Ile Tyr Thr Met Asp Tyr
1               5                   10

<210> SEQ ID NO 260
<211> LENGTH: 13
<212> TYPE: PRT
<213> ORGANISM: Homo sapiens

<400> SEQUENCE: 260

Val Arg Lys Glu Tyr Ala Asn Val Gly Val Met Asp Ser
1               5                   10

<210> SEQ ID NO 261
<211> LENGTH: 108
<212> TYPE: PRT
<213> ORGANISM: Homo sapiens

<400> SEQUENCE: 261

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys Arg
            100                 105

<210> SEQ ID NO 262
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Phe
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gln Gly Thr Lys Val Glu Ile Lys Arg
            100                 105

```
<210> SEQ ID NO 263
<211> LENGTH: 112
<212> TYPE: PRT
<213> ORGANISM: Homo sapiens

<400> SEQUENCE: 263

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Phe Asp Tyr Trp Gly Gln Gly Thr Leu Val Thr Val Ser Ser
            100                 105                 110

<210> SEQ ID NO 264
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Thr Tyr
            20                  25                  30

Gly Val His Trp Val Arg Gln Ala Pro Gly Lys Gly Leu Glu Trp Val
        35                  40                  45

Gly Val Ile Trp Pro Gly Gly Gly Thr Asp Tyr Asn Ala Ala Phe Ile
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Val
                85                  90                  95

Arg Lys Glu Tyr Ala Asn Leu Tyr Ala Met Asp Tyr Trp Gly Gln Gly
            100                 105                 110

Thr Leu Val Thr Val Ser Ser
        115

<210> SEQ ID NO 265
<211> LENGTH: 31
<212> TYPE: PRT
<213> ORGANISM: Homo sapiens

<400> SEQUENCE: 265

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala
            20                  25                  30
```

```
<210> SEQ ID NO 266
<211> LENGTH: 32
<212> TYPE: PRT
<213> ORGANISM: Homo sapiens

<400> SEQUENCE: 266

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 267
<211> LENGTH: 31
<212> TYPE: PRT
<213> ORGANISM: Homo sapiens

<400> SEQUENCE: 267

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser
            20                  25                  30

<210> SEQ ID NO 268
<211> LENGTH: 32
<212> TYPE: PRT
<213> ORGANISM: Homo sapiens

<400> SEQUENCE: 268

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 269
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 270
<211> LENGTH: 30
<212> TYPE: PRT
<213> ORGANISM: Homo sapiens

<400> SEQUENCE: 270
```

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30

<210> SEQ ID NO 271
<211> LENGTH: 32
<212> TYPE: PRT
<213> ORGANISM: Homo sapiens

<400> SEQUENCE: 271

Gly Val Pro Ser Arg Phe Ser Gly Ser Arg Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 272
<211> LENGTH: 15
<212> TYPE: PRT
<213> ORGANISM: Homo sapiens

<400> SEQUENCE: 272

Trp Tyr Gln Gln Lys Pro Gly Gln Ala Pro Arg Leu Leu Ile Tyr
1               5                   10                  15

<210> SEQ ID NO 273
<211> LENGTH: 32
<212> TYPE: PRT
<213> ORGANISM: Homo sapiens

<400> SEQUENCE: 273

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 274
<211> LENGTH: 23
<212> TYPE: PRT
<213> ORGANISM: Homo sapiens

<400> SEQUENCE: 274

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 275
<211> LENGTH: 15
<212> TYPE: PRT
<213> ORGANISM: Homo sapiens

<400> SEQUENCE: 275

Trp Tyr Gln Gln Lys Pro Gly Gln Pro Pro Lys Leu Leu Ile Tyr
1               5                   10                  15

<210> SEQ ID NO 276
<211> LENGTH: 32
<212> TYPE: PRT
<213> ORGANISM: Homo sapiens

```
<400> SEQUENCE: 276

Gly Val Pro Asp Arg Phe Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30
```